(12) United States Patent
Yang

(10) Patent No.: US 7,001,901 B2
(45) Date of Patent: Feb. 21, 2006

(54) TETRAZOLYLPROPIONAMIDES AS INHIBITORS OF Aβ PROTEIN PRODUCTION

(75) Inventor: Michael G. Yang, Narberth, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 341 days.

(21) Appl. No.: 10/650,358

(22) Filed: Aug. 27, 2003

(65) Prior Publication Data

US 2004/0082568 A1    Apr. 29, 2004

Related U.S. Application Data

(60) Provisional application No. 60/406,144, filed on Aug. 27, 2002.

(51) Int. Cl.
| | |
|---|---|
| A61K 31/55 | (2006.01) |
| A61K 31/41 | (2006.01) |
| C07D 267/02 | (2006.01) |
| C07D 401/12 | (2006.01) |
| C07D 257/04 | (2006.01) |

(52) U.S. Cl. ............... 514/217.09; 514/326; 514/381; 540/491; 540/603; 546/210; 548/252

(58) Field of Classification Search .......... 514/217.09, 514/326, 381; 540/491, 603; 546/210; 548/252
See application file for complete search history.

(56) References Cited

FOREIGN PATENT DOCUMENTS

| WO | WO 00/07995 | 2/2000 |
|---|---|---|
| WO | WO 00/38618 | 7/2000 |
| WO | WO 01/77086 | 10/2001 |
| WO | WO 01/92235 | 12/2001 |

OTHER PUBLICATIONS

Chapman, P. F., et al., "Impaired synaptic plasticity and learning in aged amyloid precursor protein transgenic mice", *Nature Neurosci.* (1999), 2, 271-276.

Dahlgren, K. N., et al., "Oligomeric and Fibrillar Species of Amyloid-β Peptides Differentially Affect Neuronal Viability", *J. Biol. Chem.* (2002), 277, 32046-32053.

Götz, J., et al., "Formation of Neurofibrillary Tangles in P301L Tau Transgenic Mice Induced by Aβ42 Fibrils", *Science* (2001) 293, 1491-1495.

Lewis, J., et al., "Enhanced Neurofibrillary Degeneration in Transgenic Mice Expressing Mutant Tau and APP", *Science* (2001), 293, 1487-1491.

McLean, C. A., et al., "Soluble pool of Aβ-amyloid as a determinant of severity of neurodegeneration in Alzheimer's disease", *Ann. Neurol.* (1999) 46, 860-866.

Seiffert, D.,F., et al., "Presenilin-1 and -2 Are Molecular Targets for γ-Secretase Inhibitors", *J. Biol. Chem.* (2000) 275, 34086-34091.

Selkoe, D. J., "Alzheimer's Disease: Genes, Proteins, & Therapy", *Physiol. Rev.* (2001) 81, 741-766.

Selkoe, D. J., " . . . Mechanism of Alzheimer's Disease", *Ann. Rev. Cell Biol.* (1994) 10:373-403.

Thal, D. R., et al., "Two Types of Sporadic Cerebral Amyloid Angiopathy", *J. Neuropath. Exp. Neuro.* (2002) 61: 82-293.

Walsh, D. M., et al., "Naturally secreted oligomers of amyloid β protein potently inhibit hippocampal long-term potentiation in vivo", *Nature* (2002) 416, 535-539.

Wolfe, M. S., "Secretase Targets for Alzheimer's Disease: Identification and Therapeutic Potential", *J. Med. Chem.* (2001) 44, 2039-2060.

*Primary Examiner*—Johann Richter
*Assistant Examiner*—Ebenezer Sackey
(74) *Attorney, Agent, or Firm*—Aldo A. Algieri

(57) ABSTRACT

This invention relates to novel tetrazolyl-propionamides in which the amide group comprises an aminoazepinone, and related structures, of Formula (I):

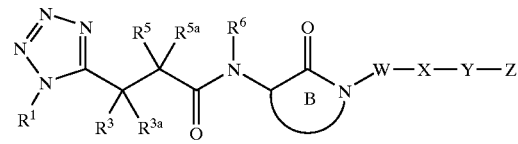

(I)

or pharmaceutically acceptable salt or prodrug forms thereof, their pharmaceutical compositions and methods of use. These novel compounds inhibit the processing of amyloid precursor protein and, more specifically, inhibit the production of Aβ-peptide, thereby resulting in prevention and treatment of the neuropathology associated with production of Aβ-peptide. More particularly, the present invention relates to the treatment of neurological disorders related to β-amyloid production such as Alzheimer's disease.

15 Claims, No Drawings

TETRAZOLYLPROPIONAMIDES AS INHIBITORS OF Aβ PROTEIN PRODUCTION

CROSS-REFERENCE TO RELATED APPLICATIONS

This is a non-provisional application which claims the benefit of U.S. Provisional Application No. 60/406,144 filed Aug. 27, 2002.

FIELD OF THE INVENTION

This invention relates to novel tetrazolyl-propionamides in which the amide group comprises an aminoazepinone, and related structures, having drug and bio-affecting properties, their pharmaceutical compositions and methods of use. These novel compounds inhibit the processing of amyloid precursor protein and, more specifically, inhibit the production of Aβ-peptide, thereby resulting in prevention and treatment of the neuropathology associated with production of Aβ-peptide. More particularly, the present invention relates to the treatment of neurological disorders related to β-amyloid production such as Alzheimer's disease.

BACKGROUND OF THE INVENTION

Alzheimer's disease (AD) is a degenerative brain disorder characterized clinically by progressive loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. The cost of AD is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Dennis J. Selkoe; Cell Biology of the amyloid (beta)-protein precursor and the mechanism of Alzheimer's disease, Annu Rev Cell Biol, 1994, 10: 373–403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Neurofibrillar tangles are nonmembrane-bound bundles of abnormal proteinaceous filaments and biochemical and immunochemical studies have shown that their principle protein subunit is an altered phosphorylated form of the tau protein (reviewed in Selkoe, 1994).

Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP). (Selkoe 2001; Wolfe 2001)). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, Bradley, et al. 2000).

Multiple lines of evidence together strongly suggest that a reduction in brain Aβ levels will prevent the onset and progression of AD. First, Aβ is a major constituent of the parenchemyal plaques observed in all AD patients and the cerebral vasculature amyloid deposits observed in 90% AD patients (reviewed in (Selkoe 2001; Wolfe 2001)). These plaques are formed from the aggregation of soluble Aβ whose brain levels are highly correlated with the severity of AD neurodegeneration (McLean, Cherny et al. 1999). Second, mutations in three genes (APP, PS-1, or PS-2) that increase Aβ cause familial AD (FAD), where AD onset is accelerated by at least a decade. Included in the mutations that increase Aβ are chromosome 21 Trisomy that causes Down's syndrome. Third, transgenic mice that express one or more of the mutant FAD genes have increased Aβ levels, form parenchymal plaques and cerebral vascular deposits containing Aβ, exhibit memory deficits (Chapman, White et al. 1999), and enhance neurofibrillary degeneration in mice that also overexpress mutant tau (Lewis, Dickson et al. 2001). Fourth, Aβ is toxic to cultured cells (Dahlgren, Manelli et al. 2002), induces neurofibrillary tangles in mice with mutant tau (Gotz, Chen et al. 2001), and interferes with long-term potentiation, a likely component of memory ((Walsh, Klyubin et al. 2002) and references therein). Taken together, these data lead one skilled in the art to conclude that excess Aβ production and/or reduced Aβ clearance cause AD. From this it follows that reducing brain Aβ levels by inhibition of γ-secretase will prevent the onset and progression of AD.

In addition to AD, excess production and/or reduced clearance of Aβ causes cerebral amyloid angiopathy (CAA) (reviewed in (Thal, Gherbremedhin et al. 2002)). In these patients, vascular amyloid deposits cause degeneration of vessel walls and aneurysms that may be responsible for 10–15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

It is hypothesized that inhibiting the production of Aβ will prevent and reduce neurological degeneration, reducing neurotoxicity and, generally, mediating the pathology associated with Aβ production. One method of treatment would therefore be based on drugs that inhibit the formation of Aβ in vivo.

Methods of treatment could target the formation of Aβ through the enzymes involved in the proteolytic processing of β-amyloid precursor protein. Compounds that inhibit β- or γ-secretase activity, either directly or indirectly, could control the production of Aβ. Advantageously, compounds that specifically target γ-secretases, could control the production of Aβ. Such inhibition of β- or γ-secretases could thereby reduce production of Aβ, which, could reduce or prevent the neurological disorders associated with Aβ protein.

As evidenced by the interest in the treatment of neurological disorders related to β-amyloid production, such as Alzheimer's disease and Down's Syndrome, a wide variety of compounds which inhibit Aβ protein production have been studied. Copending, commonly assigned PCT international patent applications WO 00/07995 (published Feb. 17, 2000) and WO 00/38618 (published Jul. 6, 2000), disclose lactams of general formula:

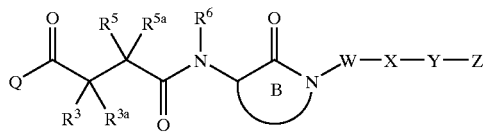

wherein the lactam ring B is substituted by a substituted succinamido group. These compounds inhibit the processing of amyloid precursor protein and, more specifically, inhibit the production of Aβ-peptide, thereby, acting to prevent or treat the neuropathology associated with production of Aβ-peptide.

Copending, commonly assigned PCT international patent application WO 01/92235, published Dec. 6, 2001, discloses lactams of general formula:

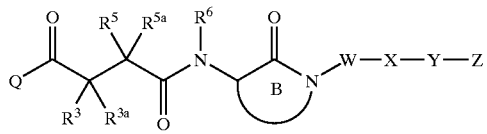

wherein the lactam ring B is substituted by cyclic succinamides. These compounds inhibit the processing of amyloid precursor protein and, more specifically, inhibit the production of Aβ-peptide, thereby, acting to prevent or treat the neuropathology associated with production of Aβ-peptide.

Copending, commonly assigned PCT international patent application WO 01/77086, published Oct. 18, 2001, discloses lactams of general formula:

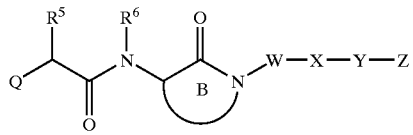

as inhibitors of β-amyloid peptide release and having utility in treating Alzheimer's disease. Though some of the present compounds of this invention appear to fall within the generic description of the above publication, they are not specifically disclosed, suggested, or claimed therein.

Thus, it is desirable to develop additional and/or improved inhibitors of Aβ protein production to treat Alzheimer's disease. The present invention discloses compounds of enhanced activity in inhibiting Aβ protein production.

None of the above references expressly teach or suggest the compounds of the present invention which are described in detail below.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

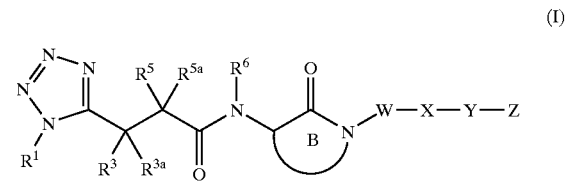

or pharmaceutically acceptable salt or prodrug forms thereof, wherein $R^1$, $R^3$, $R^{3a}$, $R^5$, $R^{5a}$, $R^6$, Ring B, W, X, Y, and Z are defined below, are effective inhibitors of the production of Aβ.

DETAILED DESCRIPTION OF PREFERRED EMBODIMENTS

[1] Thus, in a first embodiment, the present invention provides a novel compound of Formula (I):

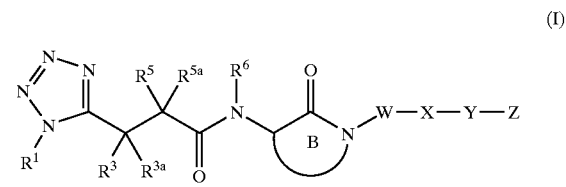

or a pharmaceutically acceptable salt or prodrug thereof, wherein:

$R^1$ is H, $C_1$–$C_6$ alkyl optionally substituted with 0–2 $R^{2a}$;

$C_2$–$C_6$ alkenyl optionally substituted with 0–2 $R^{2a}$; or $C_2$–$C_6$ alkynyl optionally substituted with 0–2 $R^{2a}$;

$R^{2a}$, at each occurrence, is independently selected from
H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_4$ alkyl, $C_1-C_4$ alkoxy, $C_1-C_4$ haloalkyl, $C_1-C_4$ haloalkoxy, $C_1-C_4$ haloalkyl-S—;
phenyl substituted with 0–3 $R^{2b}$;
$C_3-C_6$ cycloalkyl substituted with 0–3 $R^{2b}$; and
5 to 7 membered heterocycle containing 1 to 4 heteroatoms selected from nitrogen, oxygen, and sulphur, wherein said 5 to 7 membered heterocycle is substituted with 0–3 $R^{2b}$;

$R^{2b}$, at each occurrence, is independently selected from
H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_4$ alkyl, $C_1-C_4$ alkoxy, $C_1-C_4$ haloalkyl, $C_1-C_4$ haloalkoxy, and $C_1-C_4$ haloalkyl-S—;

$R^3$ is H, $NH_2$, $NR^{25}R^{26}$,
$C_1-C_6$ alkyl substituted with 0–3 $R^4$;
$C_2-C_6$ alkenyl substituted with 0–3 $R^4$; or
$C_2-C_6$ alkynyl substituted with 0–3 $R^4$;

$R^{3a}$ is H, $C_1-C_6$ alkyl, or $C_2-C_6$ alkenyl;
alternatively, $R^3$ and $R^{3a}$ are combined to form a 3–6 membered carbocyclic group selected from cyclopropyl, cyclobutyl, cyclopentyl, cyclopentenyl, cyclohexyl, and cyclohexenyl;
wherein said 3–6 membered carbocyclic group is substituted with 0–2 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3-C_6$ carbocyclic group substituted with 0–3 $R^{23}$;

$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $C_1-C_4$ alkyl, $C_2-C_4$ alkenyl, $C_2-C_4$ alkynyl, $C_1-C_4$ alkoxy, $C_1-C_4$ haloalkyl, $C_1-C_4$ haloalkoxy, and $C_1-C_4$ haloalkyl-S—, $C_3-C_6$ carbocycle, aryl, and a
5 to 6 membered heterocycle containing 1 to 4 heteroatoms selected from nitrogen, oxygen, and sulphur;

$R^5$ is H;
$C_1-C_6$ alkyl substituted with 0–2 $R^{5b}$;
$C_2-C_6$ alkenyl substituted with 0–2 $R^{5b}$;
$C_2-C_6$ alkynyl substituted with 0–2 $R^{5b}$;
$C_3-C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5a}$ is H, $C_1-C_4$ alkyl, or $C_2-C_4$ alkenyl;
alternatively, $R^5$ and $R^{5a}$ may be combined to form a 3–6 membered carbocyclic moiety selected from cyclopropyl, cyclobutyl, cyclopentyl, cyclopentenyl, cyclohexyl, and cyclohexenyl;

$R^{5b}$, at each occurrence, is independently selected from:
H, $C_1-C_6$ alkyl, $CF_3$, $OR^{14}$, Cl, F, Br, I, =O, CN, $NO_2$, $NR^{15}R^{16}$;
$C_3-C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from
H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_4$ alkyl, $C_1-C_3$ alkoxy, $C_1-C_3$ haloalkyl, $C_1-C_3$ haloalkoxy, and $C_1-C_3$ haloalkyl-S—;

$R^6$ is H or $C_1-C_6$ alkyl;
Ring B is a 7 membered lactam,
wherein the lactam is saturated, partially saturated or unsaturated;
wherein each additional lactam carbon is substituted with 0–2 $R^{11}$; and,
optionally, the lactam contains an additional heteroatom selected from —O—, —S—, —S(=O)—, —S(=O)_2—, —N=, —NH—, and —N($R^{10}$)—;
additionally, two $R^{11}$ substituents on adjacent atoms may be combined to form a benzo fused radical; wherein said benzo fused radical is substituted with 0–4 $R^{13}$;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;
additionally, two $R^{11}$ substituents on the same or adjacent carbon atoms may be combined to form a $C_3-C_6$ carbocyclic radical substituted with 0–3 $R^{13}$;

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
$C_1-C_6$ alkyl optionally substituted with 0–3 $R^{10a}$;
$C_6-C_{10}$ aryl substituted with 0–4 $R^{10b}$;
$C_3-C_{10}$ carbocycle substituted with 0–3 $R^{10b}$; or
5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from
H, $C_1-C_6$ alkyl, $OR^{14}$, Cl, F, Br, I, =O, CN, $NO_2$, $NR^{15}R^{16}$, $CF_3$,
phenyl substituted with 0–3 $R^{10b}$;
$C_3-C_7$ cycloalkyl substituted with 0–3 $R^{10b}$; and
5 to 7 membered heterocycle containing 1 to 4 heteroatoms selected from nitrogen, oxygen, and sulphur, wherein said 5 to 7 membered heterocycle is substituted with 0–3 $R^{10b}$;

$R^{10b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, $C_1-C_4$ haloalkoxy, and $C_1-C_4$ haloalkyl-S—;

$R^{11}$, at each occurrence, is independently selected from
H, $C_1-C_4$ alkoxy, Cl, F, Br, I, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1-C_6$ alkyl optionally substituted with 0–3 $R^{11a}$;
$C_6-C_{10}$ aryl substituted with 0–3 $R^{11b}$;
$C_3-C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from
H, $C_1-C_6$ alkyl, $OR^{14}$, Cl, F, Br, I, =O, CN, $NO_2$, $NR^{15}R^{16}$, $CF_3$;

phenyl substituted with 0–3 $R^{11b}$;

$C_3$–$C_7$ cycloalkyl substituted with 0–3 $R^{11b}$; and 5 to 7 membered heterocycle containing 1 to 4 heteroatoms selected from nitrogen, oxygen, and sulphur, wherein said 5 to 7 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond, —$CH_2$—, —$CH_2CH_2$—;

X is a bond, -phenyl-, -pyridyl-, -cyclohexyl-, or -piperidinyl-;

Y is a bond, —C(=O)—, —O—, —S—, —S(=O)—, —S(=O)_2—, —NH—, —N(CH_3)—, or —N(CH_2CH_3)—;

Z is H;

$C_1$–$C_8$ alkyl substituted with 0–3 $R^{12a}$;

$C_2$–$C_6$ alkenyl substituted with 0–3 $R^{12a}$;

$C_2$–$C_6$ alkynyl substituted with 0–3 $R^{12a}$;

$C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_3$–$C_6$ cycloalkyl, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S, and aryl substituted with 0–3 $R^{12c}$;

$R^{12c}$, at each occurrence, is independently selected from H, methyl, ethyl, propyl, methoxy, ethoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, C(=O)$CH_3$, $CO_2H$, $CO_2CH_3$, and $C_1$–$C_3$ haloalkyl;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{15}$, at each occurrence, is independently selected from H, and $C_1$–$C_6$ alkyl;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)_2—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)_2—;

$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)_2—;

additionally, $R^{18}$ and $R^{19}$, when substituents on the same atom, may be combined to form a 5 to 7 membered nitrogen containing heterocyclic ring;

$R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{25}$, at each occurrence, is independently selected from H, and $C_1$–$C_6$ alkyl; and $R^{26}$, at each occurrence, is independently selected from H, $C_1$–$C_6$ alkyl, $C_3$–$C_4$ alkenyl, $C_3$–$C_4$ alkynyl, ($C_1$–$C_6$ alkyl)-C(=O)—, ($C_1$–$C_6$ alkyl)-S(=O)_2—, aryl ($C_1$–$C_4$ alkyl)-, $C_3$–$C_6$ cycloalkyl, and $C_3$–$C_6$ cycloalkyl($C_1$–$C_4$ alkyl)-.

[2] In a preferred embodiment the present invention provides for a compound of Formula (Ib):

(Ib)

or a pharmaceutically acceptable salt or prodrug thereof, wherein:

$R^1$ is H, $C_1$–$C_6$ alkyl optionally substituted with 0–1 $R^{2a}$;

$C_2$–$C_6$ alkenyl optionally substituted with 0–1 $R^{2a}$; or $C_2$–$C_6$ alkynyl optionally substituted with 0–1 $R^{2a}$;

$R^{2a}$, at each occurrence, is independently selected from H, OH, Cl, F, Br, CN, $NO_2$, $CF_3$, acetyl, $SCH_3$, $S(=O)CH_3$, $S(=O)_2CH_3$, methyl, ethyl, methoxy, ethoxy, —$OCF_3$, —$SCF_3$;

phenyl substituted with 0–3 $R^{2b}$;

$C_3$–$C_6$ cycloalkyl substituted with 0–3 $R^{2b}$; and 5 to 7 membered heterocycle containing 1 to 4 heteroatoms selected from nitrogen, oxygen, and sulphur, wherein said 5 to 7 membered heterocycle is substituted with 0–3 $R^{2b}$;

$R^{2b}$, at each occurrence, is independently selected from H, OH, Cl, F, Br, CN, $NO_2$, $CF_3$, acetyl, $SCH_3$, $S(=O)CH_3$, $S(=O)_2CH_3$, methyl, ethyl, methoxy, ethoxy, —$OCF_3$, and —$SCF_3$;

$R^3$ is H, $NH_2$, $C_1$–$C_5$ alkyl, $C_2$–$C_5$ alkenyl, $C_2$–$C_5$ alkynyl, (aryl)$C_1$–$C_4$ alkyl-, or ($C_3$–$C_6$ cycloalkyl)$C_1$–$C_4$ alkyl-;

$R^5$ is H;

$C_1$–$C_4$ alkyl substituted with 0–1 $R^{5b}$;

$C_2$–$C_4$ alkenyl substituted with 0–1 $R^{5b}$; or $C_2$–$C_4$ alkynyl substituted with 0–1 $R^{5b}$;

$R^{5b}$, at each occurrence, is independently selected from:

H, methyl, ethyl, propyl, butyl, methoxy, ethoxy, propoxy, butoxy, $CF_3$, Cl, F, Br, I, =O;

$C_3$–$C_6$ carbocycle substituted with 0–3 $R^{5c}$;

phenyl substituted with 0–3 $R^{5c}$; or 5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, methyl, ethyl, propyl, methoxy, ethoxy, and —$OCF_3$;

Ring B is selected from:

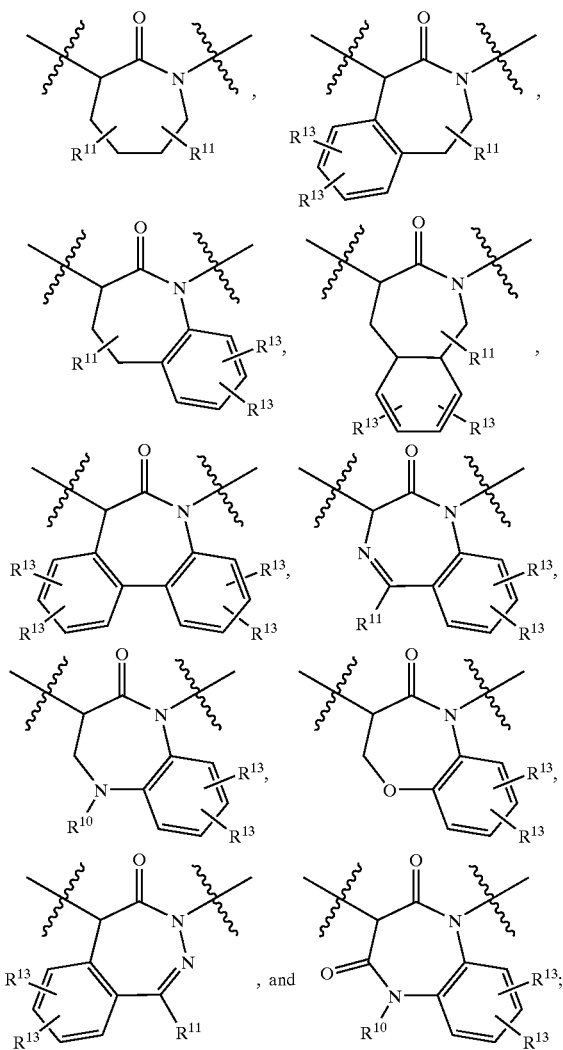

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;

$C_1$–$C_4$ alkyl optionally substituted with 0–1 $R^{10a}$;
phenyl substituted with 0–3 $R^{10b}$;
$C_3$–$C_7$ carbocycle substituted with 0–3 $R^{10b}$; and
5 to 7 membered heterocycle containing 1 to 4 heteroatoms selected from nitrogen, oxygen, and sulphur, wherein said 5 to 7 membered heterocycle is substituted with 0–3 $R^{10b}$;

$R^{10a}$, at each occurrence, is independently selected from H, $C_1$–$C_4$ alkyl, $OR^{14}$, Cl, F, Br, I, =O, CN, $NO_2$, $NR^{15}R^{16}$, $CF_3$,
phenyl substituted with 0–3 $R^{10b}$;
$C_3$–$C_7$ cycloalkyl substituted with 0–3 $R^{10b}$; and 5 to 7 membered heterocycle containing 1 to 4 heteroatoms selected from nitrogen, oxygen, and sulphur, wherein said 5 to 7 membered heterocycle is substituted with 0–3 $R^{10b}$;

$R^{10b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

$R^{11}$, at each occurrence, is independently selected from H, =O, $NR^{18}R^{19}$, $CF_3$;
$C_1$–$C_4$ alkyl optionally substituted with 0–1 $R^{11a}$;
phenyl substituted with 0–3 $R^{11b}$;
$C_3$–$C_7$ carbocycle substituted with 0–3 $R^{11b}$; and
5 to 7 membered heterocycle containing 1 to 4 heteroatoms selected from nitrogen, oxygen, and sulphur, wherein said 5 to 7 membered heterocycle is substituted with 0–3 $R^{11b}$;

$R^{11a}$, at each occurrence, is independently selected from H, $C_1$–$C_4$ alkyl, $OR^{14}$, F, Cl, =O, $NR^{15}R^{16}$, $CF_3$,
phenyl substituted with 0–3 $R^{11b}$;
$C_3$–$C_7$ cycloalkyl substituted with 0–3 $R^{11b}$; and
5 to 7 membered heterocycle containing 1 to 4 heteroatoms selected from nitrogen, oxygen, and sulphur, wherein said 5 to 7 membered heterocycle is substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
$C_1$–$C_6$ alkyl substituted with 0–1 $R^{12a}$;
$C_2$–$C_6$ alkenyl substituted with 0–1 $R^{12a}$; or
$C_2$–$C_6$ alkynyl substituted with 0–1 $R^{12a}$;

$R^{12a}$, at each occurrence, is independently selected from H, OH, Cl, F, Br, CN, $NO_2$, $CF_3$, methoxy, ethoxy, —$OCF_3$;
phenyl substituted with 0–4 $R^{12b}$;
$C_3$–$C_6$ carbocycle substituted with 0–4 $R^{12b}$; or
5 to 6 membered heterocycle containing 1 to 4 heteroatoms selected from nitrogen, oxygen, and sulphur, wherein said 5 to 6 membered heterocycle is substituted with 0–3 $R^{12b}$;

$R^{12b}$, at each occurrence, is independently selected from H, OH, Cl, F, Br, CN, $NO_2$, $CF_3$, acetyl, $SCH_3$, $S(=O)CH_3$, $S(=O)_2CH_3$, $C_1$–$C_4$ alkyl, $C_1$–$C_3$ alkoxy, $C_2$–$C_4$ alkenyl, —$OCF_3$, and —$SCF_3$;

$R^{13}$, at each occurrence, is independently selected from H, OH, methyl, ethyl, propyl, methoxy, ethoxy, Cl, F, Br, CN, $NO_2$, $NR^{15}R^{16}$, and $CF_3$;

$R^{14}$ is H, phenyl, benzyl, methyl, ethyl, propyl, or butyl;

$R^{15}$, at each occurrence, is independently selected from H, and $C_1$–$C_4$ alkyl;

$R^{16}$, at each occurrence, is independently selected from H, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from
H, OH, methyl, ethyl, propyl, butyl, phenyl, benzyl, phenethyl; and additionally, $R^{18}$ and $R^{19}$, when substituents on the same atom, may be combined to form a 5 to 7 membered nitrogen containing heterocyclic ring.

[3] In a preferred embodiment the present invention provides for a compound of Formula (Ib) wherein:

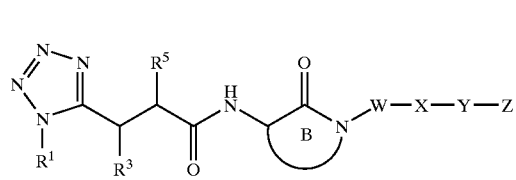
(Ib)

or a pharmaceutically acceptable salt or prodrug thereof, wherein:

$R^1$ is $C_1$–$C_6$ alkyl, $C_2$–$C_6$ alkenyl, or $C_2$–$C_6$ alkynyl;
$R^3$ is H, $NH_2$, $C_1$–$C_5$ alkyl, or $C_2$–$C_5$ alkenyl;
$R^5$ is H;
  $C_1$–$C_4$ alkyl substituted with 0–1 $R^{5b}$;
  $C_2$–$C_4$ alkenyl substituted with 0–1 $R^{5b}$; or
  $C_2$–$C_4$ alkynyl substituted with 0–1 $R^{5b}$;
$R^{5b}$, at each occurrence, is independently selected from:
  H, methyl, ethyl, propyl, methoxy, ethoxy, cyclopropyl, cyclobutyl, cyclopentyl, cyclopentenyl, cyclohexyl, cyclohexenyl, and phenyl;

Ring B is selected from:

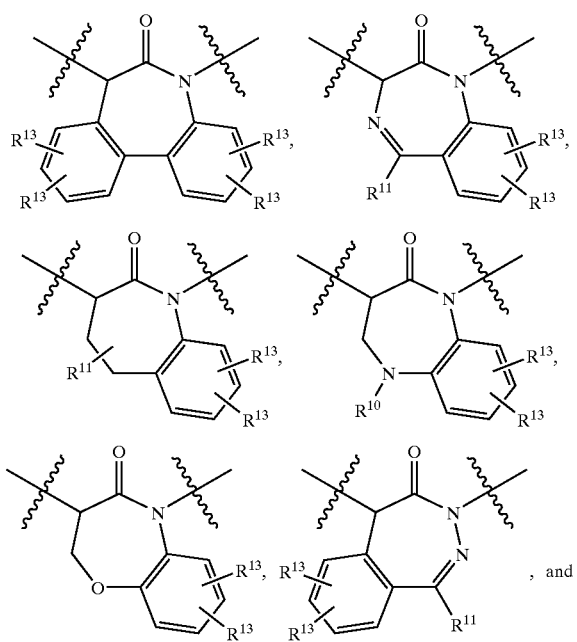

-continued

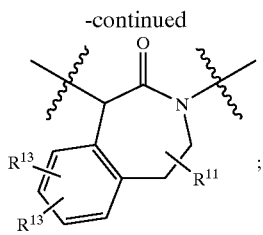
;

$R^{10}$ is H;
  $C_1$–$C_4$ alkyl optionally substituted with 0–1 $R^{10a}$;
  phenyl substituted with 0–3 $R^{10b}$;
  $C_3$–$C_7$ carbocycle substituted with 0–3 $R^{10b}$; and
  5 to 7 membered heterocycle containing 1 to 4 heteroatoms selected from nitrogen, oxygen, and sulphur, wherein said 5 to 7 membered heterocycle is substituted with 0–3 $R^{10b}$; wherein said 5 to 7 membered heterocycle is selected from pyridinyl, pyrimidinyl, triazinyl, furanyl, thienyl, thiazolyl, pyrrolyl, pyrrolidinyl, piperazinyl, piperidinyl, homopiperidinyl, pyrazolyl, imidazolyl, imidazolidinyl, oxazolyl, isoxazolyl, morpholinyl, and tetrazolyl;
$R^{10a}$, at each occurrence, is independently selected from
  H, methyl, ethyl, methoxy, phenoxy, F, Cl, $NR^{15}R^{16}$, $CF_3$;
  phenyl substituted with 0–3 $R^{10b}$;
  $C_3$–$C_7$ cycloalkyl substituted with 0–3 $R^{10b}$; and
  5 to 7 membered heterocycle containing 1 to 4 heteroatoms selected from nitrogen, oxygen, and sulphur, wherein said 5 to 7 membered heterocycle is substituted with 0–3 $R^{10b}$; wherein said 5 to 7 membered heterocycle is selected from pyridinyl, pyrimidinyl, triazinyl, furanyl, thienyl, thiazolyl, pyrrolyl, pyrrolidinyl, piperazinyl, piperidinyl, homopiperidinyl, pyrazolyl, imidazolyl, imidazolidinyl, oxazolyl, isoxazolyl, morpholinyl, and tetrazolyl;
$R^{10b}$, at each occurrence, is independently selected from
  H, OH, Cl, F, $CF_3$, methyl, ethyl, methoxy, and —$OCF_3$;
$R^{11}$, at each occurrence, is independently selected from H, $NR^{18}R^{19}$, $CF_3$;
  $C_1$–$C_4$ alkyl optionally substituted with 0–1 $R^{11a}$;
  phenyl substituted with 0–3 $R^{11b}$;
  $C_3$–$C_7$ carbocycle substituted with 0–3 $R^{11b}$; and
  5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, pyrrolidinyl, piperazinyl, piperidinyl, homopiperidinyl, pyrazolyl, imidazolyl, imidazolidinyl, oxazolyl, isoxazolyl, morpholinyl, and tetrazolyl;
$R^{11a}$, at each occurrence, is independently selected from
  H, methyl, ethyl, methoxy, phenoxy, F, Cl, $CF_3$;
  phenyl substituted with 0–3 $R^{11b}$;
  $C_3$–$C_7$ cycloalkyl substituted with 0–3 $R^{11b}$; and
  5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, pyrrolidinyl, piperazinyl, piperidinyl, homopiperidinyl, pyrazolyl, imidazolyl, imidazolidinyl, oxazolyl, isoxazolyl, morpholinyl, and tetrazolyl;

$R^{11b}$, at each occurrence, is independently selected from
H, OH, Cl, F, $CF_3$, methyl, ethyl, methoxy, and —$OCF_3$;

W is a bond;

X is a bond;

Y is a bond;

Z is H;
  $C_1$–$C_6$ alkyl substituted with 0–1 $R^{12a}$;
  $C_2$–$C_6$ alkenyl substituted with 0–1 $R^{12a}$; or
  $C_2$–$C_6$ alkynyl substituted with 0–1 $R^{12a}$;

$R^{12a}$, at each occurrence, is independently selected from
  H, OH, Cl, F, $CF_3$,
  phenyl substituted with 0–2 $R^{12b}$;
  $C_3$–$C_6$ carbocycle substituted with 0–2 $R^{12b}$; and
  5 to 6 membered heterocycle containing 1 to 4 heteroatoms selected from nitrogen, oxygen, and sulphur, wherein said 5 to 6 membered heterocycle is substituted with 0–2 $R^{12b}$;

$R^{12b}$, at each occurrence, is independently selected from
  H, OH, Cl, F, Br, CN, $NO_2$, $CF_3$, acetyl, $SCH_3$, $S(=O)CH_3$, $S(=O)_2CH_3$, methyl, ethyl, methoxy, ethoxy, allyl, —$OCF_3$, and —$SCF_3$;

$R^{13}$, at each occurrence, is independently selected from
  H, OH, methyl, ethyl, methoxy, ethoxy, Cl, F, Br, CN, $NO_2$, $NR^{15}R^{16}$, and $CF_3$;

$R^{15}$, at each occurrence, is independently selected from H, methyl, ethyl, propyl, and butyl;

$R^{16}$, at each occurrence, is independently selected from
  H, methyl, ethyl, propyl, butyl, benzyl, and phenethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

[4] In a preferred embodiment the present invention provides for a compound of Formula (Ib):

(Ib)

or a pharmaceutically acceptable salt or prodrug thereof, wherein:

$R^1$ is $C_1$–$C_5$ alkyl, $C_2$–$C_5$ alkenyl, or $C_2$–$C_5$ alkynyl;

$R^3$ is H, methyl, ethyl, propyl, butyl, pentyl, ethenyl, propenyl, or butenyl;

$R^5$ is H, $C_1$–$C_5$ alkyl; $C_2$–$C_5$ alkenyl; $C_2$–$C_5$ alkynyl; or ($C_3$–$C_6$ cycloalkyl)$C_1$–$C_4$ alkyl-;

Ring B is selected from:

, and

;

$R^{10}$ is H,
  $C_1$–$C_4$ alkyl optionally substituted with 0–1 $R^{10a}$;
  phenyl substituted with 0–1 $R^{10b}$; or
  $C_3$–$C_7$ carbocycle substituted with 0–1 $R^{10b}$, wherein said $C_3$–$C_7$ carbocycle is selected from cyclopropyl, cyclobutyl, cyclopentyl, cyclopentenyl, cyclohexyl, cyclohexenyl, and cycloheptyl;

$R^{10a}$, at each occurrence, is independently selected from
  H, methyl, methoxy, F, Cl, $CF_3$,
  phenyl substituted with 0–1 $R^{10b}$; and
  $C_3$–$C_7$ cycloalkyl substituted with 0–1 $R^{10b}$, wherein said $C_3$–$C_7$ carbocycle is selected from cyclopropyl, cyclobutyl, cyclopentyl, cyclopentenyl, cyclohexyl, cyclohexenyl, and cycloheptyl;

$R^{10b}$, at each occurrence, is independently selected from
  H, OH, Cl, F, $CF_3$, methyl, and methoxy;

$R^{11}$, at each occurrence, is independently selected from H, $NR^{18}R^{19}$, $CF_3$;
  $C_1$–$C_4$ alkyl optionally substituted with 0–1 $R^{11a}$;
  phenyl substituted with 0–1 $R^{11b}$; and
  $C_3$–$C_7$ carbocycle substituted with 0–1 $R^{11b}$, wherein said $C_3$–$C_7$ carbocycle is selected from cyclopropyl, cyclobutyl, cyclopentyl, cyclopentenyl, cyclohexyl, cyclohexenyl, and cycloheptyl;

$R^{11a}$, at each occurrence, is independently selected from
  H, methyl, methoxy, F, Cl, $CF_3$,
  phenyl substituted with 0–1 $R^{11b}$; and
  $C_3$–$C_7$ cycloalkyl substituted with 0–1 $R^{11b}$, wherein said $C_3$–$C_7$ carbocycle is selected from cyclopropyl, cyclobutyl, cyclopentyl, cyclopentenyl, cyclohexyl, cyclohexenyl, and cycloheptyl;

$R^{11b}$, at each occurrence, is independently selected from H, OH, Cl, F, $CF_3$, methyl, and methoxy;

W is a bond;

X is a bond;

Y is a bond;

Z is H;
- $C_1$–$C_4$ alkyl substituted with 0–1 $R^{12a}$;
- $C_2$–$C_4$ alkenyl substituted with 0–1 $R^{12a}$; or
- $C_2$–$C_4$ alkynyl substituted with 0–1 $R^{12a}$;

$R^{12a}$, at each occurrence, is independently selected from phenyl, cyclopropyl, cyclobutyl, cyclopentyl, cyclopentenyl, cyclohexyl, cyclohexenyl, pyridinyl, pyrimidinyl, triazinyl, furanyl, thienyl, thiazolyl, pyrrolyl, pyrrolidinyl, piperazinyl, piperidinyl, pyrazolyl, imidazolyl, imidazolidinyl, oxazolyl, isoxazolyl, and tetrazolyl;

$R^{13}$, at each occurrence, is independently selected from H, OH, methyl, ethyl, methoxy, ethoxy, Cl, F, Br, CN, $NR^{15}R^{16}$, and $CF_3$;

$R^{15}$ is H, methyl, or ethyl;

$R^{16}$ is H, methyl, or ethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

[5] In another preferred embodiment the present invention provides for a compound of Formula (Ib):

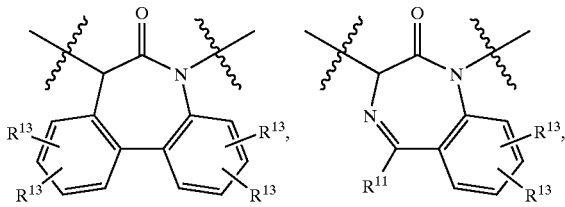

(Ib)

$R^1$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, or —$CH_2C(CH_3)_3$;

$R^3$ is H, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH=CH_2$, cis-$CH_2CH=CH(CH_3)$, trans-$CH_2CH=CH(CH_3)$, or —$CH_2CH_2CH=CH_2$;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, cyclopropyl-$CH_2$—, or cyclobutyl-$CH_2$—;

Ring B is selected from:

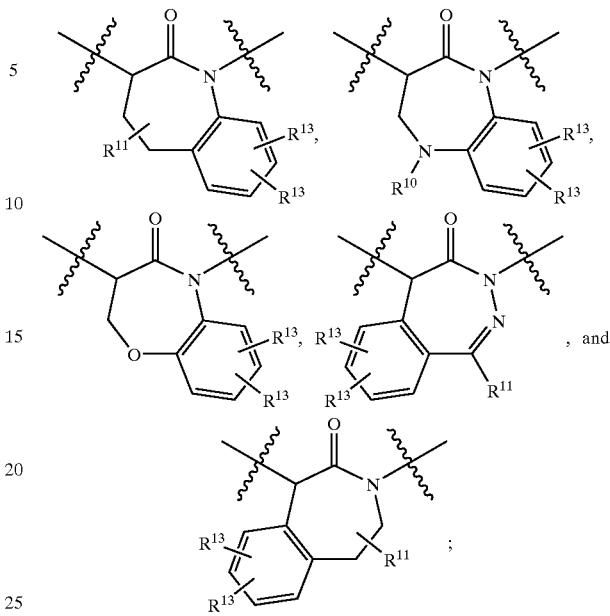

W is a bond;

X is a bond;

Y is a bond;

Z is methyl, ethyl, i-propyl, n-propyl, n-butyl, i-butyl, s-butyl, t-butyl, allyl, cyclopropyl-, cyclobutyl-, cyclopentyl-, cyclopropyl-$CH_2$—, cyclobutyl-$CH_2$—, or cyclopentyl-$CH_2$—;

$R^{10}$, at each occurrence, is independently selected from H, methyl, ethyl, i-propyl, n-propyl, n-butyl, i-butyl, s-butyl, t-butyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)$CH_2$—, (3-Cl-phenyl)$CH_2CH_2$—, 4-$CH_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3-$CH_3$-phenyl)$CH_2CH_2$—, 4-$CF_3$-phenyl, (4-$CF_3$-phenyl)$CH_2$—, (4-$CF_3$-phenyl)$CH_2CH_2$—, cyclopropyl, (cyclopropyl)$CH_2$—, (cyclopropyl)$CH_2CH_2$-cyclobutyl, (cyclobutyl)$CH_2$—, (cyclobutyl)$CH_2CH_2$—, cyclopentyl, (cyclopentyl)$CH_2$—, (cyclopentyl)$CH_2CH_2$-cyclohexyl, (cyclohexyl)$CH_2$—, (cyclohexyl)$CH_2CH_2$—, $R^{11}$, at each occurrence, is independently selected from H, methyl, ethyl, i-propyl, n-propyl, n-butyl, i-butyl, s-butyl, t-butyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)$CH_2$—, (3-Cl-phenyl)$CH_2CH_2$—, 4-$CH_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3-$CH_3$-phenyl)$CH_2CH_2$—, 4-$CF_3$-phenyl, (4-$CF_3$-phenyl)$CH_2$—, (4-$CF_3$-phenyl)$CH_2CH_2$—, cyclopropyl, (cyclopropyl)$CH_2$—, (cyclopropyl)$CH_2CH_2$—, cyclobutyl, (cyclobutyl)$CH_2$—, (cyclobutyl)$CH_2CH_2$—, cyclopentyl, (cyclopentyl)$CH_2$—, (cyclopentyl)$CH_2CH_2$—, cyclohexyl, (cyclohexyl)$CH_2$—, (cyclohexyl)CH$_2$CH$_2$—, pyrid-2-yl, pyrid-3-yl, pyrid-4-yl, piperidinyl, or homopiperidinyl; and
R$^{13}$, at each occurrence, is independently selected from H, F, Cl, OH, —CH$_3$, —CH$_2$CH$_3$, —OCH$_3$, or —CF$_3$.

[6] In another preferred embodiment the present invention provides for a compound of Formula (Ic):

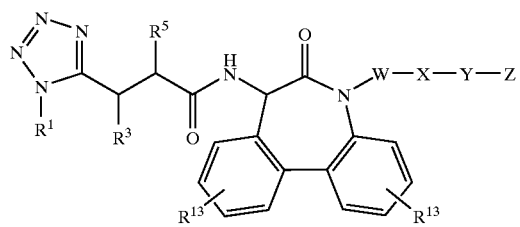

(Ic)

or a pharmaceutically acceptable salt or prodrug thereof.

[7] In another preferred embodiment the present invention provides for a compound of Formula (Id):

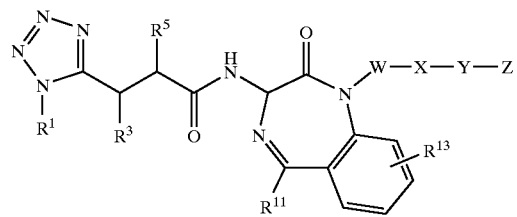

(Id)

or a pharmaceutically acceptable salt or prodrug thereof.

[8] In another preferred embodiment the present invention provides for a compound of Formula (Ie):

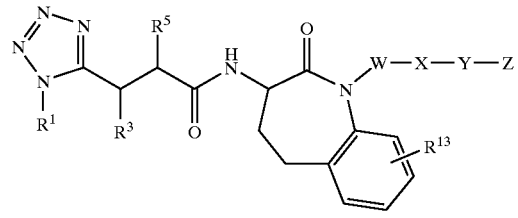

(Ie)

or a pharmaceutically acceptable salt or prodrug thereof.

[9] In another preferred embodiment the present invention provides for a compound of Formula (If):

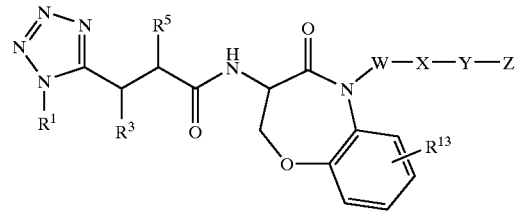

(If)

or a pharmaceutically acceptable salt or prodrug thereof.

[10] In another preferred embodiment the present invention provides for a compound of Formula (Ig):

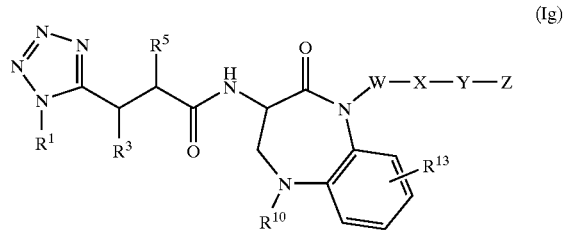

(Ig)

or a pharmaceutically acceptable salt or prodrug thereof.

[11] In another preferred embodiment the present invention provides for a compound of Formula (Ih):

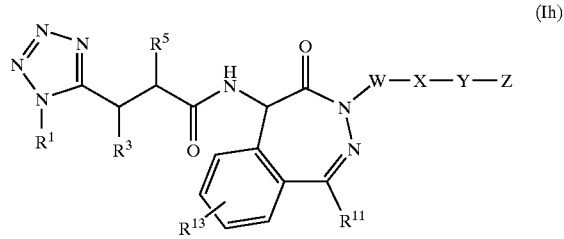

(Ih)

or a pharmaceutically acceptable salt or prodrug thereof.

[12] In another preferred embodiment the present invention provides for a compound selected from:

4-Methyl-2-(1-propyl-1H-tetrazol-5-ylmethyl)-pentanoic acid [1-methyl-2-oxo-5-(4-trifluoromethyl-phenyl)-2,3-dihydro-1H-benzo[e][1,4]diazepin-3-yl]-amide;

4-Methyl-2-[1-(1-propyl-1H-tetrazol-5-yl)-ethyl]-pentanoic acid (5-methyl-6-oxo-6,7-dihydro-5H-dibenzo[b,d]azepin-7-yl)-amide;

4-Methyl-2-[1-(1-propyl-1H-tetrazol-5-yl)-ethyl]-pentanoic acid [1-methyl-2-oxo-5-(4-trifluoromethyl-phenyl)-2,3-dihydro-1H-benzo[e][1,4]diazepin-3-yl]-amide;

4-Methyl-2-(1-propyl-1H-tetrazol-5-ylmethyl)-pentanoic acid (1,5-bis-cyclopropylmethyl-2-oxo-2,3,4,5-tetrahydro-1H-benzo[b][1,5]diazepin-3-yl)-amide;

4-Methyl-2-(1-propyl-1H-tetrazol-5-ylmethyl)-pentanoic acid (1-cyclopropylmethyl-2-oxo-2,3,4,5-tetrahydro-1H-benzo[b][1,5]diazepin-3-yl)-amide;

4-Methyl-2-(1-propyl-1H-tetrazol-5-ylmethyl)-pentanoic acid (1-cyclopropylmethyl-5-methyl-2-oxo-2,3,4,5-tetrahydro-1H-benzo[b][1,5]diazepin-3-yl)-amide;

4-Methyl-2-[1-(1-propyl-1H-tetrazol-5-yl)-ethyl]-pentanoic acid (1,5-bis-cyclopropylmethyl-2-oxo-2,3,4,5-tetrahydro-1H-benzo[b][1,4]diazepin-3-yl)-amide;

2-[Amino-(1-propyl-1H-tetrazol-5-yl)-methyl]-4-methyl-pentanoic acid [1-methyl-2-oxo-5-(4-trifluoromethyl-phenyl)-2,3-dihydro-1H-benzo[e][1,4]diazepin-3-yl]-amide;

2-Isobutyl-3-(1-methyl-1H-tetrazol-5-yl)-hex-5-enoic acid (5-cyclopropylmethyl-1-methyl-2-oxo-2,3,4,5-tetrahydro-1H-benzo[b][1,4]diazepin-3-yl)-amide;

2-Isobutyl-4-methyl-3-(1-methyl-1H-tetrazol-5-yl)-pentanoic acid (5-cyclopropylmethyl-1-methyl-2-oxo-2,3,4,5-tetrahydro-1H-benzo[b][1,4]diazepin-3-yl)-amide;

or a pharmaceutically acceptable salt or prodrug thereof.

It is appreciated that certain features of the invention, which are, for clarity, described herein in the context of separate embodiments, may also be provided in combination in a single embodiment. As such, it is understood that any and all embodiments of the present invention may be taken in conjunction with any other embodiment to describe additional embodiments of the present invention. Conversely, various features of the invention which are for brevity, described herein in the context of a single embodiment, may also be provided separately or in any subcombination. As such, it is understood that any elements of an embodiment are meant to be combined with any and all other elements from any of the embodiments to describe additional embodiments.

In a preferred embodiment Ring B is independently:

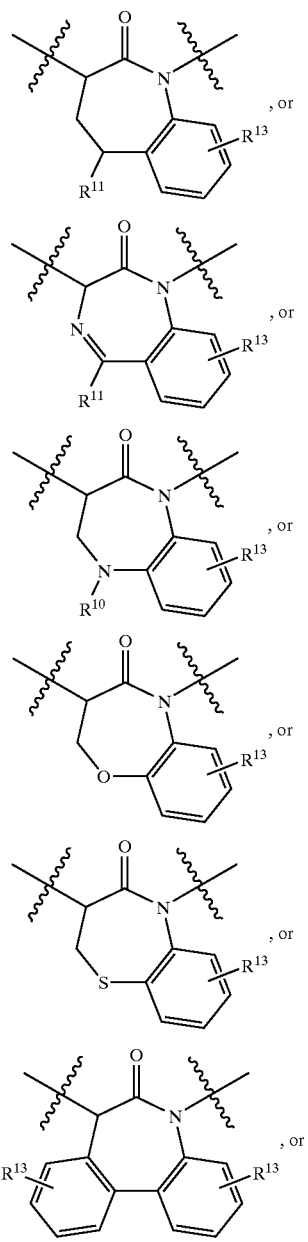

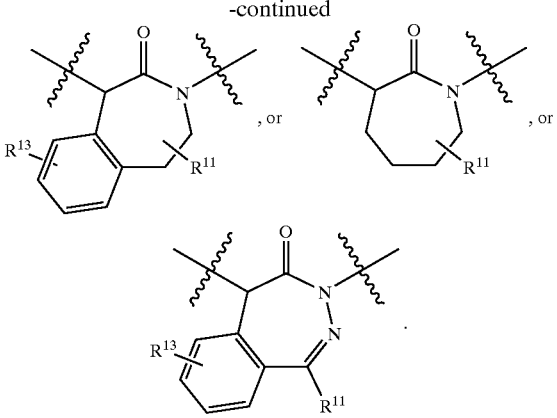

Also included in the present invention are compounds as set forth in the embodiments above wherein $R^5$ is $C_1$–$C_6$ alkyl, $C_2$–$C_6$ alkenyl, or ($C_3$–$C_6$ cycloalkyl)$C_1$–$C_3$ alkyl-.

In a preferred embodiment $R^5$ is $C_2$–$C_6$ alkyl. In another preferred embodiment $R^5$ is ($C_3$–$C_6$ cycloalkyl)methyl.

In another preferred embodiment $R^5$ is —$CH_3$, —$CH_2CH_3$, —$CH_2CH_2CH_3$, —$CH(CH_3)$ 2, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH_2CH$=$CH_2$, —$CH$=$C(CH_3)_2$, —$CH_2C$(=$CH_2$)$CH_3$, or cyclopropylmethyl-.

In preferred embodiment $R^5$ is —$CH_3$, —$CH_2CH_3$, —$CH_2CH_2CH_3$, —$CH_2CH(CH_3)_2$, —$CH_2CH_2CH_2CH_3$, —$CH_2CH_2CH_2CH_2CH_3$, or —$CH_2CH_2CH(CH_3)_2$.

In another preferred embodiment $R^5$ is —$CH_2CH(CH_3)_2$.

In another preferred embodiment $R^5$ is cyclopropylmethyl-.

Also included in the present invention are compounds as set forth in the embodiments above wherein $R^{11}$ is H, $NR^{18}R^{19}$; $C_1$–$C_4$ alkyl optionally substituted with 0–1 $R^{11a}$; phenyl substituted with 0–3 $R^{11b}$; $C_3$–$C_7$ cycloalkyl substituted with 0–3 $R^{11b}$; or pyridinyl substituted with 0–3 $R^{11b}$; wherein $R^{11a}$ is phenyl substituted with 0–3 $R^{11b}$;

wherein $R^{11b}$, at each occurrence, is independently selected from H, OH, Cl, F, $CF_3$, methyl, ethyl, propyl, butyl, methoxy, ethoxy, and propoxy.

In another preferred embodiment $R^{11}$ is phenyl substituted by 0–3 $R^{11b}$, wherein $R^{11b}$, at each occurrence, is independently selected from OH, Cl, F, CN, $CF_3$, methyl, methoxy, and $OCF_3$. In a preferred embodiment $R^{11}$ is phenyl, 4-F-phenyl, 3-F-phenyl, 2-F-phenyl, 4-Cl-phenyl, 3-Cl-phenyl, 4-$CH_3$-phenyl, 3-$CH_3$-phenyl, or 4-$CF_3$-phenyl.

Also included in the present invention are compounds as set forth in the embodiments above wherein W may be selected from a bond or —$CH_2$—. In preferred embodiment W is a bond.

Also included in the present invention are compounds as set forth in the embodiments above wherein X is a bond or phen-1,3-diyl. In a preferred embodiment X is a bond.

Also included in the present invention are compounds as set forth in the embodiments above wherein Y is a bond, —C(=O)—, —O—, or —N($R^{19}$)—. In independently preferred embodiments Y is a bond; Y is —C(=O)—; Y is —O—; or Y is —NH—, —N($CH_3$)—, or —N($CH_2CH_3$)—.

Also included in the present invention are compounds as set forth in the embodiments above wherein Z is H, $C_1$–$C_4$ alkyl substituted with 0–1 $R^{12a}$; $C_2$–$C_4$ alkenyl substituted with 0–1 $R^{12a}$; or $C_2$–$C_4$ alkynyl substituted with 0–1 $R^{12a}$; wherein, $R^{12a}$ is selected from H, OH, Cl, F, $CF_3$; phenyl substituted with 0–1 $R^{12b}$; $C_3$–$C_7$ carbocycle substituted with 0–1 $R^{12b}$; and 5 to 6 membered heterocycle containing 1 to 4 heteroatoms selected from nitrogen, oxygen, and sulphur, wherein said 5 to 6 membered heterocycle is substituted with 0–3 $R^{12b}$; wherein, $R^{12b}$, at each occurrence, is independently selected from H, OH, Cl, F, Br, CN, $NO_2$, $CF_3$, acetyl, $SCH_3$, methyl, ethyl, methoxy, ethoxy, allyl, —$OCF_3$, and $SCF_3$.

In preferred embodiment Z is H, $C_1$–$C_4$ alkyl substituted with 0–1 $R^{12a}$; $C_2$–$C_4$ alkenyl substituted with 0–1 $R^{12a}$; or $C_2$–$C_4$ alkynyl substituted with 0–1 $R^{12a}$; wherein, $R^{12a}$ is selected from H, OH, Cl, F, $CF_3$; phenyl substituted with 0–1 $R^{12b}$; and $C_3$–$C_6$ carbocycle substituted with 0–1 $R^{12b}$; wherein, $R^{12b}$ is selected from H, OH, Cl, F, Br, CN, $NO_2$, $CF_3$, acetyl, $SCH_3$, methyl, ethyl, methoxy, ethoxy, allyl, —$OCF_3$, and $SCF_3$.

In another preferred embodiment Z is $C_1$–$C_4$ alkyl, $C_2$–$C_4$ alkenyl, $C_2$–$C_4$ alkynyl, or cyclopropyl($C_1$–$C_3$ alkyl)-.

In another preferred embodiment Z is methyl, ethyl, i-propyl, n-propyl, n-butyl, i-butyl, s-butyl, t-butyl, allyl, cyclopropylmethyl-, or cyclopropylethyl-. In a more preferred embodiment Z is methyl, ethyl, i-propyl, n-propyl, allyl, or cyclopropylmethyl-. In another more preferred embodiment Z is methyl.

Also included in the present invention are compounds as set forth in the embodiments above wherein $R^{13}$ and $R^{13a}$, at each occurrence, are independently selected from H, OH, methyl, methoxy, F, Cl, Br, CN, and —$CF_3$. In a preferred embodiment $R^{13}$ and $R^{13a}$, at each occurrence, are independently selected from H, F, and Cl.

Also included in the present invention are compounds as set forth in the embodiments above wherein $R^{14}$ is H, phenyl, benzyl, methyl, ethyl, propyl, or butyl;

Also included in the present invention are compounds as set forth in the embodiments above wherein $R^{15}$, at each occurrence, is independently selected from H, methyl, ethyl, propyl, and butyl.

Also included in the present invention are compounds as set forth in the embodiments above wherein $R^{16}$, at each occurrence, is independently selected from H, OH, methyl, ethyl, propyl, butyl, benzyl, and phenethyl.

Also included in the present invention are compounds as set forth in the embodiments above wherein $R^{18}$, at each occurrence, is independently selected from H, methyl, ethyl, propyl, butyl, phenyl, benzyl, and phenethyl.

Also included in the present invention are compounds as set forth in the embodiments above wherein $R^{19}$, at each occurrence, is independently selected from H, methyl, ethyl, propyl, and butyl.

In a second embodiment, the present invention provides a pharmaceutical composition comprising a compound of Formula (I) and a pharmaceutically acceptable carrier.

In a third embodiment, the present invention provides a method for the treatment of neurological disorders associated with β-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for inhibiting γ-secretase activity for the treatment of a physiological disorder associated with inhibiting γ-secretase activity comprising administering to a host in need of such inhibition a therapeutically effective amount of a compound of Formula (I) that inhibits γ-secretase activity.

Thus, the present invention provides a method for inhibiting γ-secretase activity comprising administering to a host in need of such inhibition a therapeutically effective amount of a compound of Formula (I) that inhibits γ-secretase activity.

In a preferred embodiment the physiological disorder associated with inhibiting γ-secretase activity is Alzheimer's Disease.

In a fifth embodiment, the present invention provides a compound of Formula (I) for use in therapy.

In a preferred embodiment the present invention provides a compound of Formula (I) for use in therapy of Alzheimer's Disease.

In a sixth embodiment, the present invention provides for the use of a compound of Formula (I) for the manufacture of a medicament for the treatment of Alzheimer's Disease.

Definitions

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Colin Dingwall, "Spotlight on BACE: The secretases as targets for treatment in Alzheimer's disease" Journal of Clinical Investigation, November 2001, vol. 108, No. 9, page 1243–1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e. =O), then 2 hydrogens on the atom are replaced.

When any variable (e.g. $R^4$, $R^{5c}$, $R^{10b}$, $R^{11b}$ etc.) occurs more than one time in any constituent or formula for a compound, its definition at each occurrence is independent of its definition at every other occurrence. Thus, for example, if a group is shown to be substituted with 0–2 $R^4$, then said group may optionally be substituted with up to two $R^4$ groups and $R^4$ at each occurrence is selected independently from the definition of $R^4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl". Additionally, unless otherwise specified, "propyl" denotes n-propyl or i-propyl; "butyl" denotes n-butyl, i-butyl, sec-butyl, or t-butyl.

As used herein, "alkenyl" or "alkenylene" is intended to include hydrocarbon chains of either a straight or branched configuration and one or more unsaturated carbon-carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_7$ cycloalkyl" denotes such as cyclopropyl, cyclobutyl, cyclopentyl, cyclohexyl or cycloheptyl; "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated or partially unsaturated. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, indanyl, adamantyl, or tetrahydronaphthyl (tetralin). Preferred "carbocycle" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated, partially unsaturated or unsaturated, and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl or naphthyl. Preferred "aryl" is phenyl. Unless otherwise specified, "aryl" may be unsubstituted or substituted with 0, 1, 2, or 3 groups selected from H, methyl, ethyl, propyl, butyl, methoxy, ethoxy, propoxy, butoxy, amino, hydroxy, Cl, F, Br, I, $CF_3$, $SCH_3$, $S(O)CH_3$, $SO_2CH_3$, $SCF_3$, —$N(CH_3)_2$, $N(CH_3)H$, CN, $NO_2$, $OCF_3$, $C(=O)CH_3$, $CO_2H$, $CO_2CH_3$, $CHF_2$, or $OCHF_2$.

The phrase "additional lactam carbon", as used herein, is intended to denote the number of optional carbon atoms in the lactam ring B of Formula (I). Formula (I''):

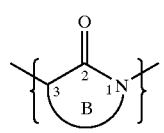

(I'')

represents the lactam ring B of Formula (I). Additional lactam carbons are carbons in lactam ring B other than the carbons numbered 2 and 3 in the backbone of the formula. Lactam ring B contains four additional lactam carbons, wherein one additional lactam carbon may optionally be replaced by a heteroatom selected from oxygen, nitrogen, and sulfur, such that the total number of atoms of lactam ring B, including atoms numbered 1, 2 and 3 in the backbone, is seven. It is further understood that lactam ring B may optionally be partially unsaturated (i.e. two adjacent atoms in the ring a connected by a double bond) wherein the backbone of lactam ring B may contain one or two double bonds. Examples of lactam ring B include:

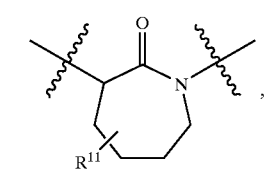
B1

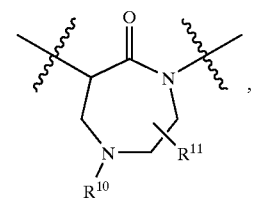
B2

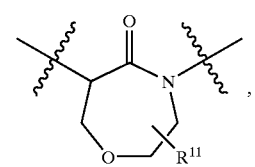
B3

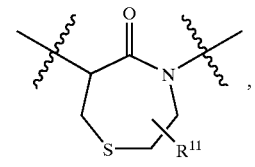
B4

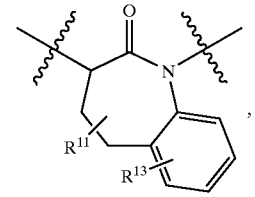
B5

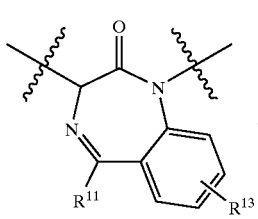
B6

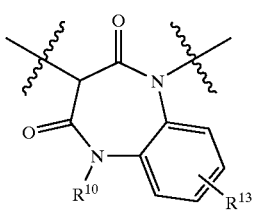
B8

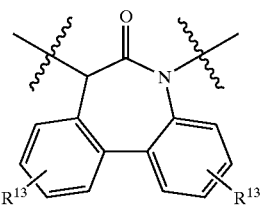
B9

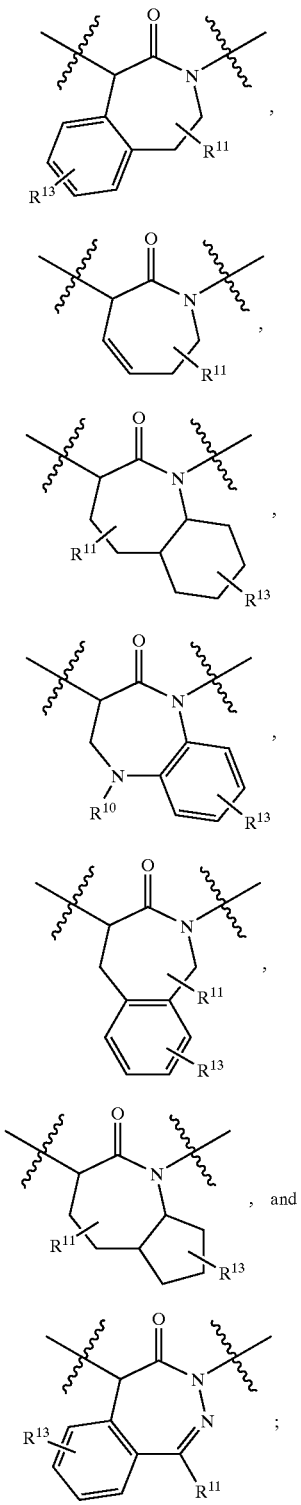

but are not intended to limit the invention.

The compounds of the invention herein described may have asymmetric centers. For example carbon 3 of lactam ring B Formula (I″) may exist in either an S or R configuration. Thus, an R or S configuration at carbon 3 in Formula (I″) is considered part of the invention. An example of such configuration includes, the S isomers:

and the R isomers:

but is not intended to be limited to these examples of lactam ring B. In a preferred embodiment lactam Ring B is the S isomer.

Additionally, the carbon atoms to which $R^3$ and $R^5$ are attached may describe chiral carbons, when $R^5$ is not the same as $R^{5a}$; and when $R^3$ is not the same as $R^{3a}$. All configurations are considered part of the invention.

When required, separation of the racemic material can be achieved by methods known in the art. All isomeric configurations are considered part of the invention.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Neurological disorder associated with Aβ production" is intended to mean neurodegenerative diseases characterized by memory impairment and cognitive dysfunction that are caused by Aβ. Such diseases are characterized by the accumulation of senile (neuritic) plaques, neurofibrillary tangles, and/or amyloid deposition in neural tissues and/or vessels, synaptic loss, and neuronal death. Such diseases are also characterized by elevated levels of soluble Aβ. Examples of these diseases include Alzheimer's disease and cerebral amyloid angiopathy.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work-up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In a preferred method of synthesis, the compounds of Formula (I) of the present invention can be prepared from carboxylic acid 1 and amine 2 using amide bond syntheses known in the art, including reagents commonly used in peptide syntheses, such as HATU, TBTU, BOP, EDC, CDI, and DCC-mediated couplings, as illustrated in Scheme 1.

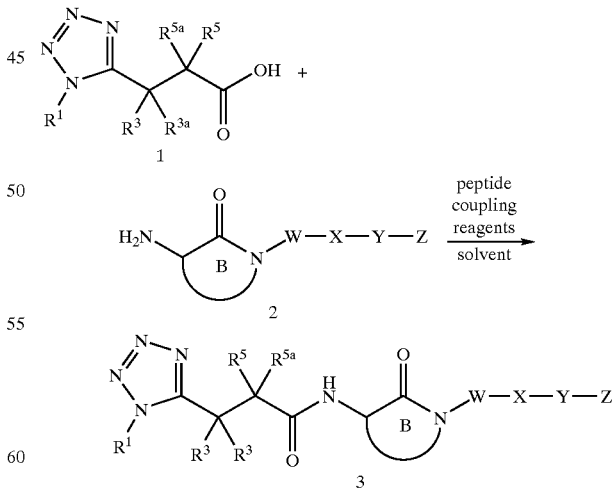

Depending on the structure of the final product, it is appreciated by those skilled in the art that protecting groups or precursor functionality convertible to the desired substituents may be used. Protecting groups and their use in synthesis are described in Green and Wuts, *Protective Groups in Organic Synthesis*, (Wiley 1991).

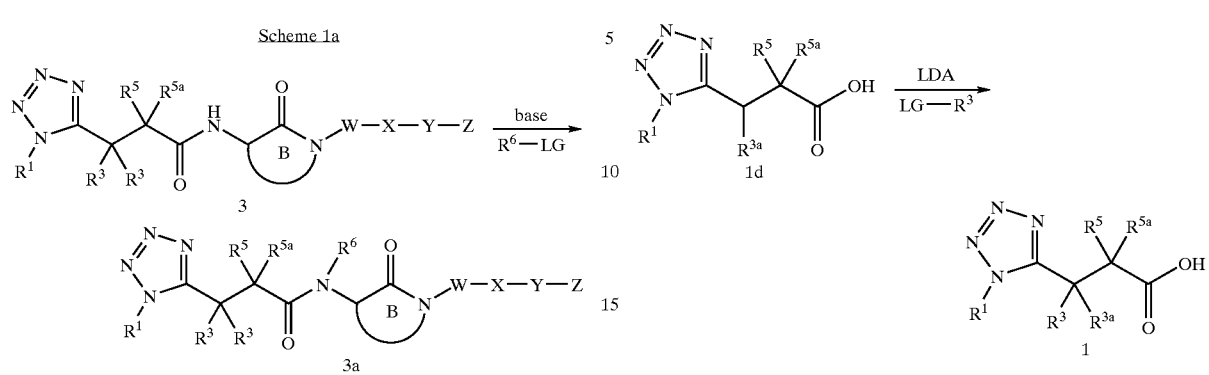

Furthermore, compound 3 can be converted to analog 3a (as shown in Scheme 1a) using standard bases, for example LDA, NaH, or NaHMDS, followed by addition of an alkylating agent $R^6$-LG wherein LG is an appropriate leaving group, for example halide, mesylate, or triflate, in an appropriate solvent.

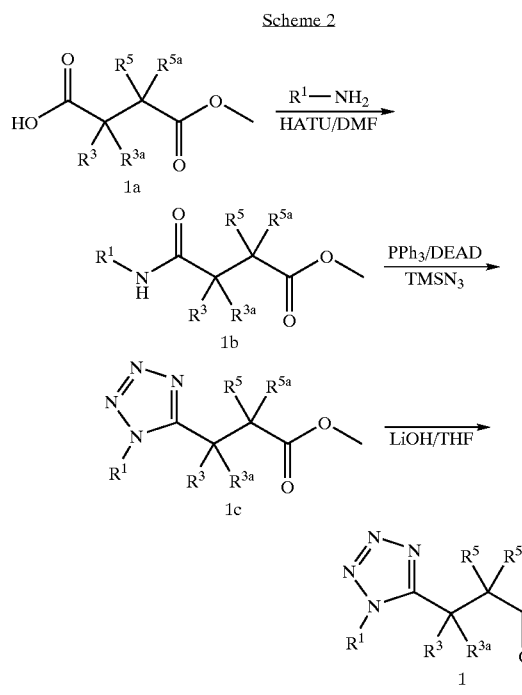

Intermediate 1 is useful for the synthesis of the compounds Formula (I). There are number of methods known to one skilled in the art to prepare 1. For example, as illustrated in Scheme 2, hydrolysis of tetrazolylpropionate ester 1c may give compound 1. Tetrazole 1c may be synthesized from amide 1b under reaction conditions known in the art, for example, through the use of $PPh_3$, DEAD, and $TMSN_3$ in THF. Additional literature references for tetrazole synthesis, relevant to the preparation of 1c, are described in *J. Org. Chem.* 1995, 60, 3112; *Recl. Trav. Chim. Pays-Bas.* 1963, 81, 286; *Chem. Rev.* 1970, 70, 163; *Tetrahedron Lett.* 1986, 27, 4749; and *J. Org. Chem.* 1950, 15, 662.

Various analogs of 1 can be prepared from intermediate 1d under reaction conditions using standard bases, for example LDA, NaH, or NaHMDS, followed by addition of an alkylating agent $R^3$-LG wherein LG is an appropriate leaving group, for example halide, mesylate, or triflate, as shown in Scheme 3. Literature references for alkylating tetrazoles and related alkylation reactions are described in *J. Org. Chem.* 1993, 58, 1623; *Synlett.* 1993, 137; and *Tetrahedron Lett.* 1991, 32, 6857.

As shown in Scheme 2, succinate 1a serve as an important precursor for making tetrazole 1. Therefore, succinate 1a is useful for the current invention, and may be synthesized by a number of methods well known in the art. For example, one representative synthetic scheme for the preparation of succinate 4 is illustrated in Scheme 4. Literature references describing the preparation of 1a and its analogs can be found in a) *Synlett*, 1993, 137; b) *Bioorg. Med. Chem. Lett.* 1998, 8, 1443; c) *Bioorg. Med. Chem. Lett.* 1998, 8, 1359; d) *Synlett*, 1998, 531; and e) PCT publications WO 01/60826 and WO 00/07995.

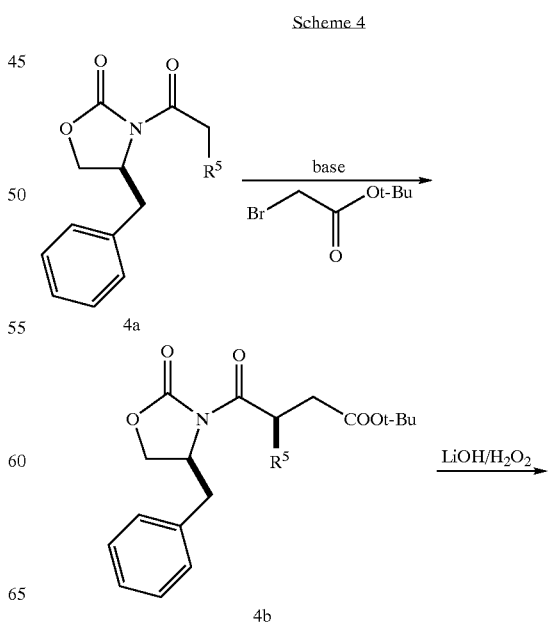

-continued

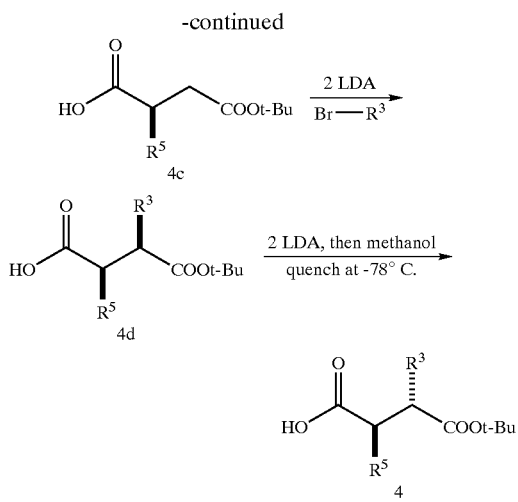

An alternative method for the epimerization procedure in Scheme 4 is shown in Scheme 5 for the preparation of succinate 4 and described in PCT publications WO 97/18207 and WO 98/51665.

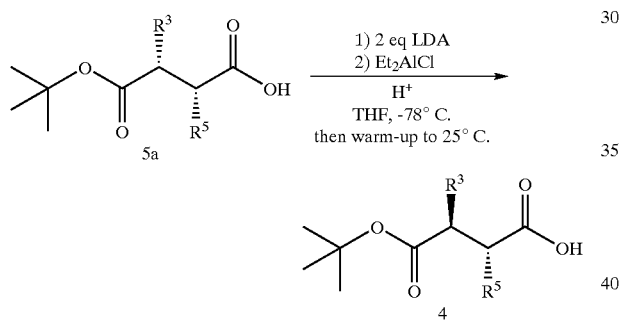

It is understood that one skilled in the art may extend the synthetic method of Scheme 4 to include substituents $R^{3a}$ and $R^{5a}$, as shown in intermediate 1a (Scheme 2). An example is illustrated in Scheme 6. A related literature procedure is described in *Bioorg. Med. Chem. Lett.* 1996, 6, 1719–1724.

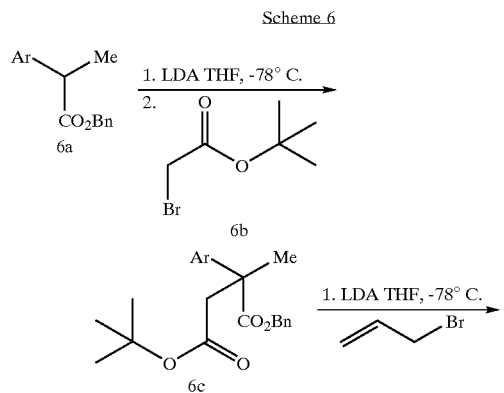

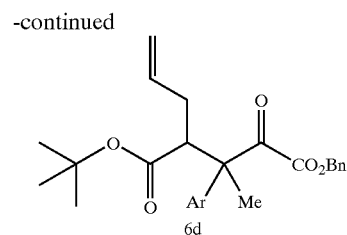

Asymmetric synthesis of 2,3-disubstituted succinates via chiral oxazolidinone controlled displacement of α-trifluoromethanesulfonate substituted esters is described in *J. Org. Chem.* 1995, 60, 4782–4785 is illustrated in Scheme 7.

Scheme 7

The synthesis of trisubstituted succinates, such as 8, is illustrated in Scheme 8. The detailed experimental procedures for making compound 8 and its analogs can be found in *Bioorg. Med. Chem. Lett.* 1998, 8, 1443.

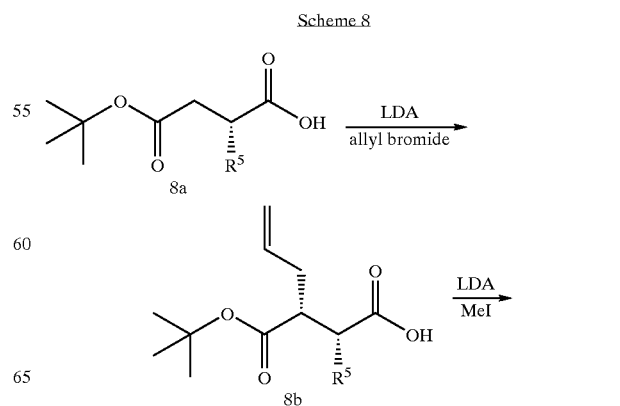

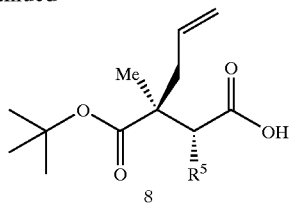

In structure 1a, substituents $R^3$ and $R^{3a}$ may comprise a cyclic group as shown in structure 9 (Scheme 9). There are a number of methods known to one skilled in the art to prepare cyclic succinate 9.

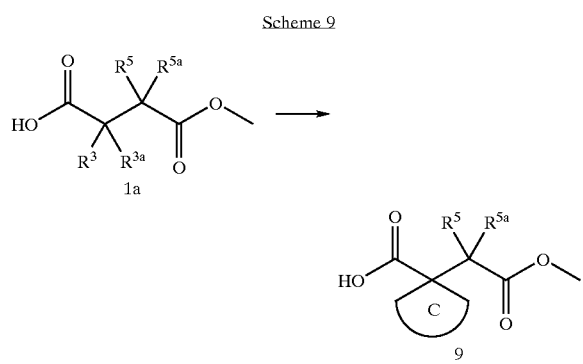

Examples of succinates wherein ring C is a carbocyclic or heterocyclic system are well known in the literature. For example, a dimethyl succinate having a 3-membered cyclopropyl ring C can be formed by a thermal or photolytic decomposition of a methyl 3-(carbomethoxy-methyl)-1-pyrazoline-3-carboxylate, as described in Bull. Soc. Chim. Fr. (1971), (6), 2290–5. A succinic acid derivative wherein ring C is a 4-membered cyclobutyl group can be formed by the method published in U.S. Pat. No. 3,828,025. A succinic acid derivative wherein ring C is a 5-membered cyclopentyl group can be formed using the methods described in Le Moal, H. et al., Bull. Soc. Chim. Fr., 1964, 579–584; Borenstein, M. R., et al., Heterocycles, 22, 1984, 2433–2438. Other examples of derivatives of succinate X wherein ring C is a five-membered cyclopentyl group or a 6-membered cyclohexyl group have been employed as matrix matalloproteinase inhibitors. See Bioorg. Med. Chem. Lett. (1998), 8(12), 1443–1448; Robinson, R. P., et al., Bioorg. Med. Chem. Lett. (1996), 6(14), 1719–1724. For the preparation of a succinic acid wherein ring C is an oxygen containing 3-membered oxirane see Kirshenbaum, K. S., Sharpless, K. B., J. Org. Chem. (1985), 50(11), 1979–82. For examples of succinate derivatives wherein ring C is a 5- or 6-membered heterocycle ring see Olivero, S., Dunach, E., Eur. J. Org. Chem. (1999), (8), 1885–1891; Eckardt et al. Helv. Chim. Acta, 55, 1972, 2432, 2433, 2434, 2438; Sandoz Ltd., NL 6409801 1963, Chem. Abstract., 63, 1965, 8324d; and Rice, L. M., et al., J. Med. Chem., 6, 1963, 388–402. It is understood that these references are only illustrative of the availability of some carbocyclic and heterocyclic succinates, however numerous references are known in literature which provide preparations of other substituted carbocyclic and heterocyclic succinates and their derivatives.

Scheme 10 illustrates one method for the introduction of a substituent on a carbon adjacent to the cyclic group in succinate 10a via deprotonation followed by standard alkylation procedures known to one skilled in the art. Treatment of 10a with an appropriate base followed by addition of an $R^5$-LG reagent, wherein LG is a leaving group such as a halide, mesylate, triflate or a tosylate, and subsequent deprotection of the benzyl group by hydrogenation employing, for example, $H_2$ and Pd/C, provides the desired succinate 10.

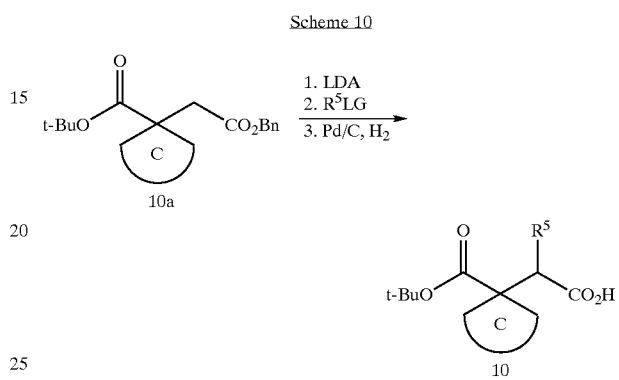

An example of a general method whereby diesters of structure 10a can be obtained from cyclic esters 11a is shown in Scheme 11. Deprotonation of such esters with, for example LDA or lithium hexamethyldisilazide, followed by reaction of the resulting ester enolate with allyl bromide provides allyl esters 11b, which may be oxidized using ruthenium peroxide in the presence of sodium periodate to give free acids 11c. If desired, esterification may be carried out using e.g. benzyl bromide in the presence of potassium carbonate.

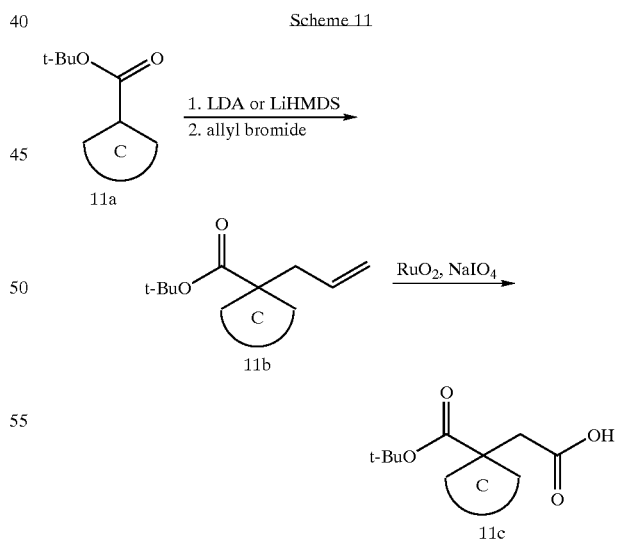

Succinate acids such as 12 with defined stereochemistry may be prepared from cyclic mono-acids 12a by use of a chiral auxiliary such as an oxazolidinone, as shown in Scheme 12. Thus, acid 12a may be converted to the oxazolidinone 12b and subjected to the Evans stereospecific alkylation sequence to provide, after removal of the auxiliary, acid esters 12. Suitable alkylating agents include alkyl, allyl, propenyl or benzyl iodides or triflates, as is known to those skilled in the art. Use of the appropriate stereochemistry in the chiral auxiliary can provide substituted cyclic succinates of either absolute configuration.

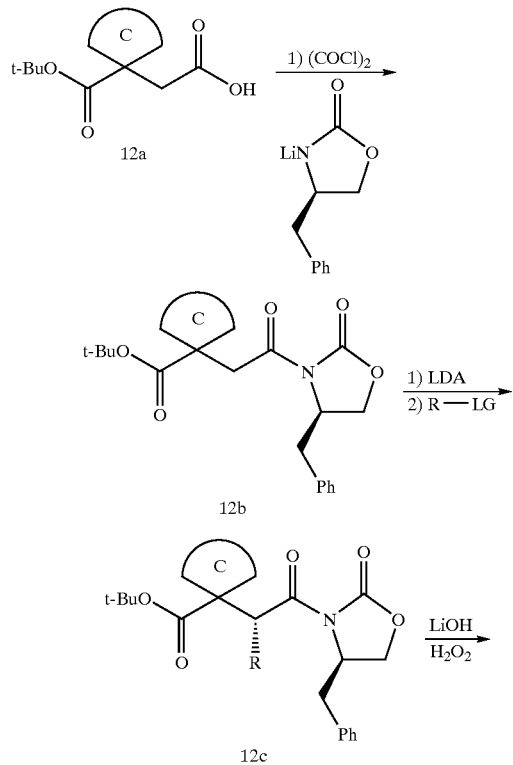

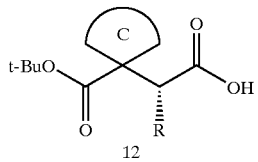

Cyclic succinate 9 and analogs of 9 can also be prepared by undergoing a ring-closing-metathesis reaction in the presence of Ruthenium complexes using the method described by Grubbs and coworkers, J. Am. Chem. Soc., 114, 7324 (1992). Scheme 13 illustrates one of such examples.

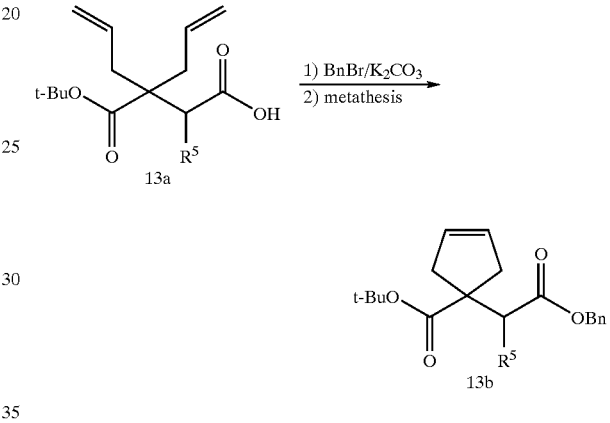

Methods illustrated above (Schemes 10–13) may be modified to prepare cyclic succinate 14 where $R^5$ and $R^{5a}$ comprise a cyclic group as shown below. One such transformation is illustrated in Scheme 14.

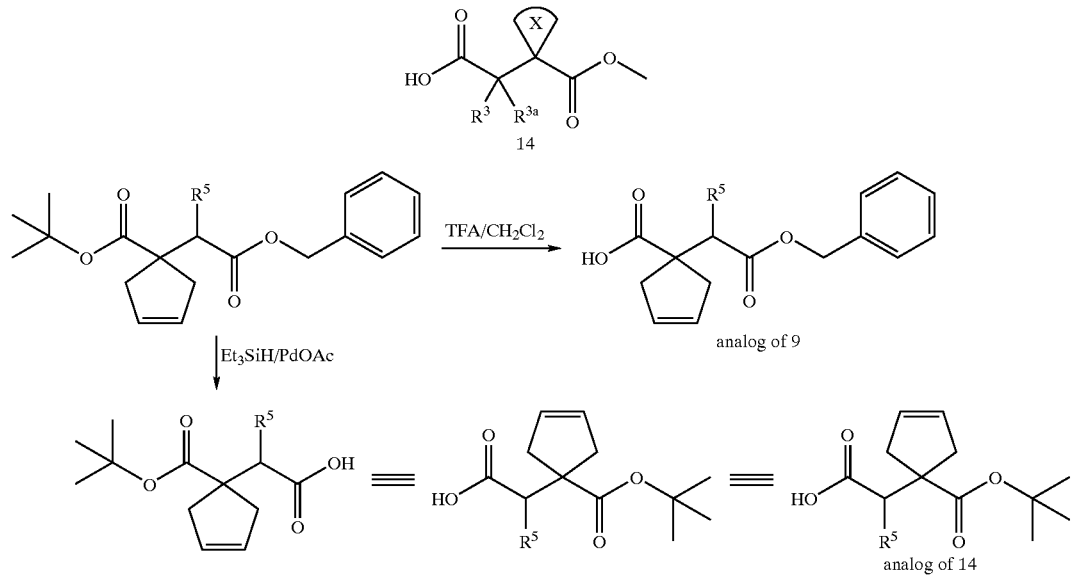

Methods for the synthesis of aminolactam 2 useful for the syntheses of compounds of formula (I) as contemplated by the present invention, including amino benzodiazepinones, amino dibenzazepinones, amino benzazepinones, amino benzothiazepinones, amino benzoxazepinones, and other related azepinones, are known in the art and are disclosed in a number of references including PCT publication number WO 02/40508, WO 02/40451, WO 98/28268, WO 99/66934, and WO 00/07995, which are hereby incorporated by reference. Additional references include Bock, et al, J. Org. Chem., 1987, 52, 3232–3239; Sherrill et al, J. Org. Chem., 1995, 60, 730–734; Walsh, D. A., Synthesis, September 1980, p. 677; and Brown, et al., Tetrahedron Letters, 1971, 8, 667–670.

For example, methods for the synthesis of amino-1,4-benzodiazepiones, 15, Scheme 15, and its related analogs, are known in the art and are disclosed in a number of references including PCT publication number WO 98/28268, WO 99/66934, and WO 00/07995, which are hereby incorporated by reference. Additional references include a) *J. Org. Chem.*, 1987, 52, 3232–3239; b) *J. Org. Chem.*, 1995, 60, 730–734; c) *Synthesis*, 1980, 677; d) *Tetrahedron Lett.* 1971, 8, 667–670; e) *J. Org. Chem.* 1998, 63, 7875; f) *J. Comb. Chem.* 2000, 513; g) *J. Med. Chem.* 1994, 37, 897; and PCT publications WO 94/01421, WO 01/74783, and WO 01/74784.

Scheme 15

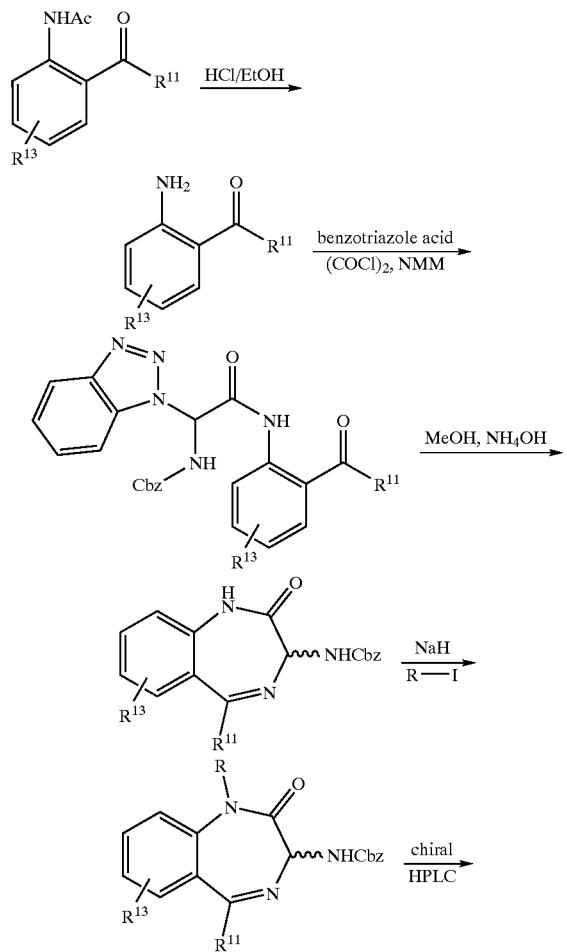

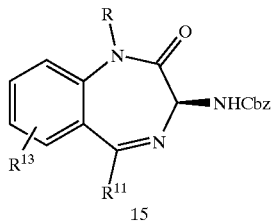

A general synthesis of amino-1,5-benzodiazepiones 16 is illustrated in Scheme 16, and detailed experimental procedures are provided below and described in *Tetrahedron*, 1998, 54, 4413.

Scheme 16

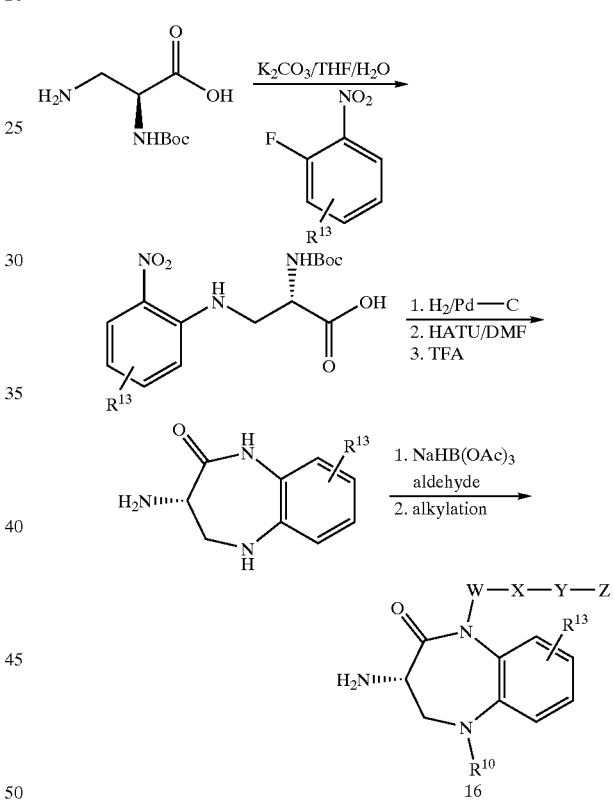

A general synthesis of amino benzodiazepine 17 is shown in Scheme 17 and described in US patent 2002/0022621.

Scheme 17

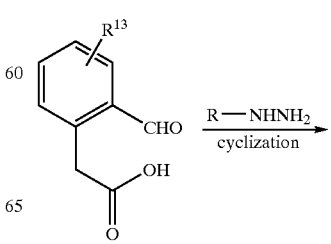

-continued

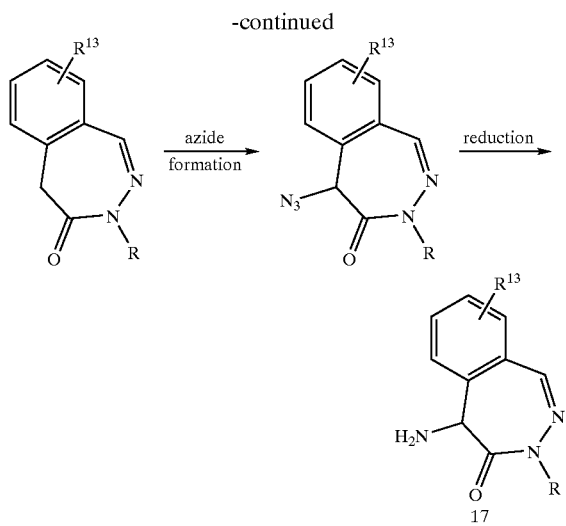

17

EXAMPLES

Chemical abbreviations used in the specification and Examples are defined as follows:
"Ac" for acetate,
"Boc" or "BOC" for N-tert-butoxycarbonyl,
"BOP" for benzotriazol-1-yloxytris-(dimethylamino)-phosphonium hexafluorophosphate,
"CDI" for carbonyl diimidazole,
"$CD_3OD$" for deuteromethanol,
"$CDCl_3$" for deuterochloroform,
"DCC" for 1,3-dicyclohexylcarbodiimide,
"DIEA" for diethyl amine,
"DMF" for N,N-dimethylformamide,
"DMAP" for 4-dimethylaminopyridine,
"DMPU" for 1,3-dimethyl-3,4,5,6-tetrahydro-2(1H)-pyrimidone,
"EDC" for 1-(3-dimethylaminopropyl)-3-ethylcarbodiimide hydrochloride,
"Et" for ethyl,
"EtOAC" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"NMM" for N-methylmorpholine,
"rt" for room temperature,
"TBTU" for O-(1H-benzotriazol-1-yl)-N,N,N',N'-tetramethyluronium tetrafluoroborate,
"TEA" for triethyl amine,
"TFA" for trifluoroacetic acid,
"THF" for tetrahydrofuran, and
"PyBoP" for benzotriazole-1-yl-oxy-tris-pyrrolidino-phosphonium hexafluorophosphate.

Typical protecting groups (Pg) used in this specification include the following:
"Bn" for benzyl,
"BOC" for t-butoxycarbonyl,
"Cbz" for benzyloxycrbonyl,
"MEM" for 2-methoxyethoxymethyl,
"Fmoc" for 9-fluorenylmethoxycarbonyl,
"PMB" for p-methoxybenzyl,
"TBS" for t-butyldimethylsilyl.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). If necessary, organic layers can be dried over sodium sulfate unless otherwise indicated. However, unless otherwise indicated, the following conditions are generally applicable.

Melting points were determined on a Mel-Temp II apparatus and are uncorrected. IR spectra were obtained on a single-beam Nicolet Nexus FT-IR spectrometer using 16 accumulations at a resolution of 4.00 $cm^{-1}$ on samples prepared in a pressed disc of KBr or as a film on KBr plates. Proton NMR spectra (300 MHz, referenced to tetramethylsilane) were obtained on a Varian INOVA 300 spectrometer. Data were referred to the lock solvent. Electrospray Ionization (ESI) experiments were performed on a Micromass II Platform single-quadrupole mass spectrometer. Exact mass determination by ESI high resolution mass spectrometry was conducted using a Finnigan MAT95S reverse-geometry sector instrument equipped with an ESI sprayer and controlled by Finnigan ICIS data system and software. HPLC analyses were obtained using a Rainin Dynamax $C_{18}$ column with UV detection at 223 nm using a standard solvent gradient program as follows:

Typical HPLC solvent conditions: Samples were dissolved in methanol (1 mg/mL) and run using the following gradient program with a solvent flow rate of 1.0 mL/min.

| Time (min) | Acetonitrile (0.05% TFA) | $H_2O$ (0.05% TFA) |
|---|---|---|
| Initial | 10 | 90 |
| 20.0 | 90 | 10 |
| 20–30 | 90 | 10 |

Elemental analyses were performed by Quantitative Technologies, Inc. (Whitehouse, N.J.).

The examples provided are intended to assist in a further understanding of the invention. Particular materials employed, species and conditions are intended to be further illustrate of the invention and not limit the reasonable scope thereof.

Example A

5-Amino-3-methyl-4,5-dihydro-3H-benzo[d][2,3]diazepin-4-one

The preparation of benzodiazepine 113 is described in Scheme A, and is also disclosed in US 2002/0022621.

Scheme A

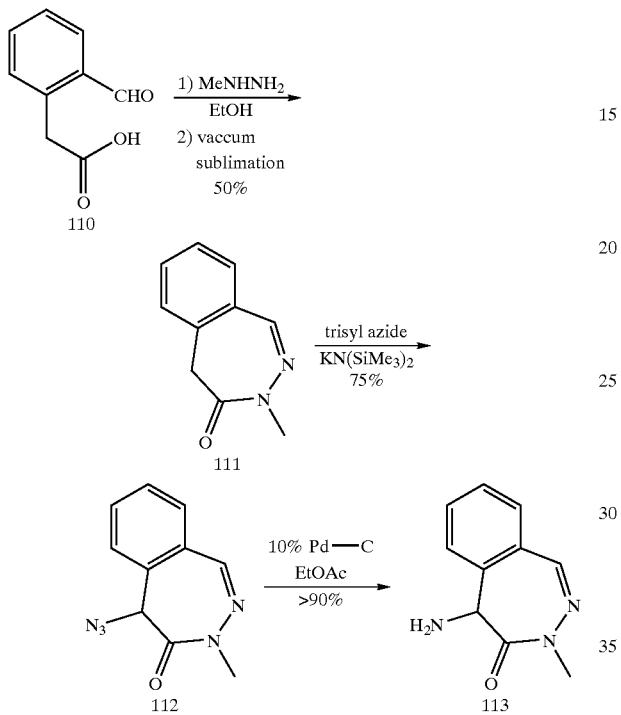

Step A: Preparation of 4,5-dihydro-3-methyl-3H-2,3-benzodiazepin-4-one, 111 (Scheme A).

To a solution of o-formylphenylacetic acid (10 g, 61 mmol) (Bleasdale et al., *J. Chem. Soc. Perkin Trans. I* 1991, 1683) in 60 mL of EtOH was added N-methylhydrazine (4.2 g, 91 mmol) and refluxed for 1 h. The reaction mixture cooled, solvent removed and transferred the crude reaction mixture to a vaccum sublimation apparatus. The imine was heated at 140° C. under high vaccum for 1 h and collected the cyclized product by extracting with hot 20% ethyl acetate in hexane (Nagarajan et al., *J. Med. Chem.*, 1972, 15(10), 1091). The product was crystallized from 20% ethyl acetate in hexane. 4,5-dihydro-3-methyl-3H-2,3-benzodiazepin-4-one was obtained in 50% yield.

$^1$H NMR (300 MHz, CDCl$_3$): in δ 8.24 (s, 1 H), 7.48–7.25 (m, 4 H), 3.48 (s, 2 H), 3.37 (s, 3 H); MS (ESI+), 175 (M+H).

Step B: Preparation of 5(R,S)-azido-4,5-dihydro-3-methyl-3H-2,3-benzodiazepin-4-one, 112 (Scheme A).

To a well stirred solution of 4,5-dihydro-3-methyl-3H-2,3-benzodiazepin-4-one (3.0 g, 17.2 mmol) in anhydrous tetrahydrofuran (100 mL) at −78° C. was added a solution of 0.5 M potassium bis(trimethylsilyl)amide in toluene (45 mL, 22.4 mmol). The reaction mixture was stirred for another 15 min followed by addition of a pre-cooled solution of 2,4,6-triisopropylbenzenesulfonyl azide (trisyl azide) (5.8 g, 19 mmol) in THF (0.4M) via a cannula over a period of 2 min (Evans et al., *J. Amer. Chem. Soc.* 1990, 112, 4011–4030; Butcher et al., *Tetrahedron Lett.*, 1996, 37(37), 6685–6688). After 5 min, acetic acid (4.9 mL, 86 mmol) was added and stirring continued for another 6 h. The reaction mixture was diluted with EtOAc (300 mL), washed with water (300 mL), aqueous NaHCO$_3$ (2×150 mL), 0.5 N HCl (200 mL) and brine (150 mL). The solvent was removed and the 5(R,S)-azido-4,5-dihydro-3-methyl-3H-2,3-benzodiazepin-4-one was purified by flash chromatography (silica) using 10% EtOAc in hexane. The azide was obtained in 75% yield.

$^1$H NMR (300 MHz, CDCl$_3$): in δ 8.36 (s, 1 H), 7.6 (m, 2 H). 7.44 (m, 2 H), 4.84 (s, 1 H), 3.46 (s, 3 H); MS (ESI+), 216 (M+H).

Step C: Preparation of 113 (Scheme A)

To a solution of 5(R,S)-azido-4,5-dihydro-3-methyl-3H-2,3-benzodiazepin-4-one (1.5 g, 7 mmol) in EtOAc (150 mL) was added 10% Pd on carbon (50 mg) and stirred under an atmosphere of hydrogen. The reaction was closely monitored by TLC using EtOAc as eluent. The reaction was complete after 1 h (TLC) and then filtered the catalyst over a pad of celite. The solvent was removed and the 5(R,S)-amino-4,5-dihydro-3-methyl-3H-2,3-benzodiazepin-4-one, 113, was dried under high vaccum. The amine may be used without further purification in coupling reactions disclosed herein with various amino acids. MS (ESI+), 190 (M+H).

Example B

Synthesis of [(3S)-1-Methyl-2-oxo-5-(4-trifluoromethyl-phenyl)-2,3-dihydro-1H-benzo[e][1,4]diazepin-3-yl]-carbamic acid benzyl ester (120)

Scheme B

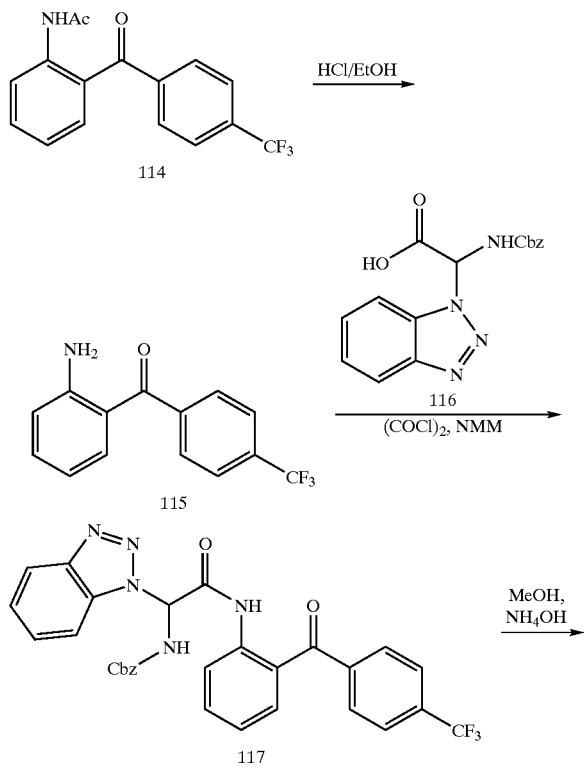

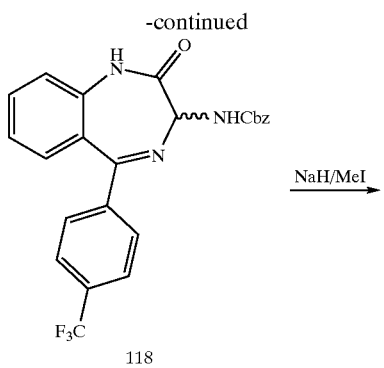

118

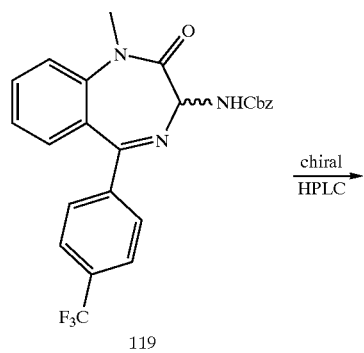

119

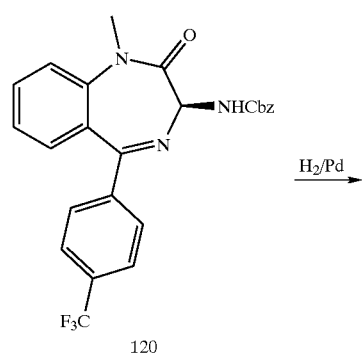

120

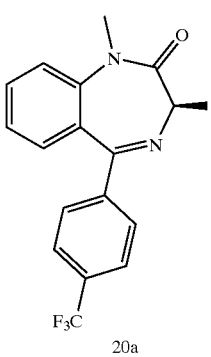

20a

Step A: Preparation of (2-Amino-phenyl)-(4-trifluoromethyl-phenyl)-methanone, 115 (Scheme B).

The synthesis of compound 114 has been described in the literature (*Chem. Pharm. Bull.*, 1989, 37(1), 110–115). To a solution of 114 (108 g, 351 mmol) in EtOH (1 L) was added 6N HCl (400 mL) at 0° C. The solution was stirred at rt for 16 hours. Upon removing EtOH, water was added followed by 6N NaOH to bring the pH level to 9. The resulting yellow precipitate was collected by vacuum filtration, washed with water, and dried in vacuo at 40° C. to give 115 (37.5 g, 41%) as a solid: $^1$H NMR (300 MHz, CDCl$_3$) δ 7.2 (m, 4H), 6.8 (d, 2H), 6.6 (m, 2H). MS [M+H]$^+$ 266.

Step B: Preparation of {Benzotriazol-1-yl-[2-(4-trifluoromethyl-benzoyl)-phenylcarbamoyl]-methyl}-carbamic acid benzyl ester, 117 (Scheme B).

The synthesis of benzotriazole acid 116 has been described in the literature (*J. Org. Chem.*, 1990, 55, 2206). To a solution of 116 (53.7 g, 164 mmol) in THF (400 mL) was added DMF (2 mL) followed by oxalyl chloride (15 mL) dropwise over 1 hour at 0° C. The reaction mixture was stirred for an additional 2.5 hours at room temperature before NMM (36 mL) was added. To this reaction mixture, a solution of 115 (37.5 g, 142 mmol) in THF (150 mL) was added slowly. After completion of the reaction was confirmed by TLC, the reaction mixture was diluted with water and extracted with methylene chloride. The combined organic layers were washed with saturated sodium bicarbonate, dried over magnesium sulfate and concentrated in vacuo to provide the crude product 117 as a light brown solid. MS [M–H]$^+$ 572.

Step C: Preparation of [2-Oxo-5-(4-trifluoromethyl-phenyl)-2,3-dihydro-1H-benzo[e][1,4]diazepin-3-yl]-carbamic acid benzyl ester, 118 (Scheme B).

The crude product 117 was re-dissolved in methanol (50 mL) and ammonia gas was bubbled through the reaction mixture. After completion of the reaction was confirmed by TLC, the solvent was removed in vacuo and 1N NaOH solution was added. This mixture was extracted with EtOAc and the organic layer was collected and concentrated in vacuo to give a thick oil. This crude oil was dissolved in HOAc (500 mL) and was treated with NH$_4$OAc (25 g) with stirring at room temperature for 20 hours before the HOAc was removed in vacuo. The residue was neutralized by 1N NaOH, extracted with ethyl acetate, and concentrated in vacuo to give 118 (35 g, 54% in two steps) as a solid: $^1$H NMR (300 MHz, DMSO) δ 8.5 (d, 1H), 7.9 (m, 2H), 7.7 (m, 2H), 7.4 (m, 6H), 5.0 (s, 2H). MS [M+H]$^+$ 454.

Step D: Preparation of [1-methyl-2-oxo-5-(4-trifluoromethyl-phenyl)-2,3-dihydro-1H-benzo[e][1,4]diazepin-3-yl]-carbamic acid benzyl ester, 120 (Scheme B).

To a solution of 118 (10 g, 22 mmol) in DMF (100 mL) under nitrogen was added K$_2$CO$_3$ (7 g, 50.7 mmol) followed by methyl iodide (8 mL). The reaction was stirred at room temperature for 16 hours before water and EtOAc were added. The organic layers were separated, dried over sodium sulfate and concentrated in vacuo. The crude product was passed through a pad of silica gel (1:1 ethyl acetate/methylene chloride) and concentrated in vacuo to give 119 (8.5 g, 83%) as a solid: $^1$H NMR (300 MHz, CDCl$_3$) δ 7.7 (m, 6H), 7.4 (m, 7H), 6.8 (d, 1H), 5.4 (d, 1H), 5.2 (m, 2H), 3.4 (s, 3H). MS [M+H]$^+$ 468.

The desired isomer 120 was the first eluting peak as the epimeric mixture of 119 was separated on a CHIRALCEL AD column with 100% acetonitrile.

Example C

Synthesis of (3S)-3-Amino-5-cyclopropylmethyl-1-methyl-1,3,4,5-tetrahydro-benzo[b][1,5]diazepin-2-one; compound 128

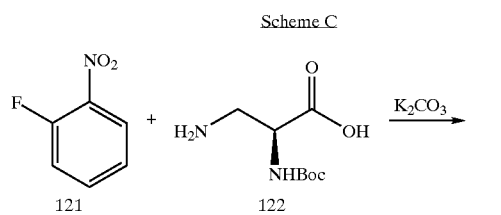

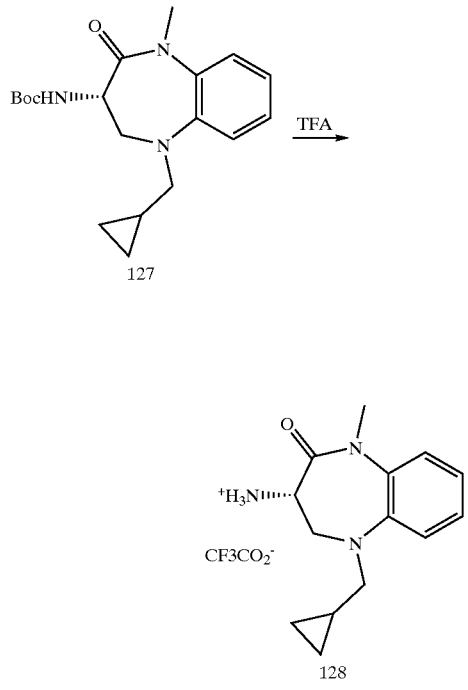

Step A: Synthesis of 2-tert-Butoxycarbonylamino-3-(2-nitro-ph

1-Fluoro-2-nitrobenzene 121 (441 mmol, 46.5 mL) was taken up in 1 L of anhydrous ethanol and treated with L-2,3-diaminopropanoic acid 122 (245 mmol, 50 g) followed by K$_2$CO$_3$ (588 mmol, 81.3 g) and H$_2$O (300 mL). The reaction mixture was warmed to reflux and stirred for 24 hours under a nitrogen atmosphere. The ethanol was evaporated in vacuo. The reaction mixture was diluted with ethyl acetate and washed with aqueous NaHCO$_3$. The organic layer was separated, concentrated in vacuo and the resulting orange oil was purified by flash chromatography to give the desired compound 123 (98%, 79.1 g). $^1$H NMR (300 MHz, CD$_3$OD) δ 8.1 (m, 1H), 7.3 (m, 1H), 7.1 (m, 1H), 6.6 (m, 1H), 4.4 (m, 1H), 3.8 (m, 1H), 3.6 (m, 1H), 1.4 (s, 9H). MS [M+H]$^+$ 326.

Step B: Synthesis of 3-(2-Amino-phenylamino)-2-tert-butoxycarbonylamino-propionic acid, 124 (Scheme C).

Nitroaniline 123 (243 mmol, 79.1 g) was taken up in 800 mL of anhydrous ethanol and treated with 10% Pd/C (2 g). The reaction mixture was stirred under 55 psi of H$_2$ for 4.5 hr, then filtered through a celite bed. The solvent was evaporated in vacuo to give the desired compound 124 (98%, 70.6 g) as a solid. $^1$H NMR (300 MHz, CD$_3$OD) δ 7.6–7.8 (m, 4H), 4.4 (m, 1H), 3.6 (m, 1H), 3.4 (m, 1H), 1.4 (s, 9H). MS [M+H]$^+$ 296.

;2qStep C: Synthesis of (2-Oxo-2,3,4,5-tetrahydro-1H-benzo[b][1,5]diazepin-3-yl)-carbamic acid tert-butyl ester, 125 (Scheme C).

The aniline 124 (239 mmol, 70.6 g) was taken up in anhydrous CH$_2$Cl$_2$ (1.4 L) and DMF (500 mL), and treated with HOBt (286 mmol, 38.8 g), EDC (286 mmol, 55 g) and DIPEA (478 mmol, 83.3 mL). The reaction mixture was stirred at room temperature under a nitrogen atmosphere for 16 h. The solvent was evaporated in vacuo, and the residue was diluted with ethyl acetate and washed with water. The organic layer was separated, concentrated in vacuo and purified by flash chromatography using 30% EtOAc/hexane to give the desired lactam 125 (73%, 48 g) as an oil.

$^1$H NMR (300 MHz, CDCL$_3$) δ 7.6–7.8 (m, 4H), 5.7 (m, 1H), 4.5 (m, 1H), 3.8 (m, 1H), 3.5 (m, 1H), 1.4 (s, 9H). MS [M+H]$^+$ 278.

Step D: Synthesis of (5-Cyclopropylmethyl-4-oxo-2,3,4,5-tetrahydro-1H-benzo[b][1,5]diazepin-3-yl)-carbamic acid tert-butyl ester, 126 (Scheme C).

To a solution of 125 (21.5 g, 77.5 mmol) and cyclopropylcarboxaldehyde (10.9 g, 155 mmol) in methylene chloride (310 mL) under nitrogen atmosphere was added sodium triacetoxyborohydride (50.1 g, 388 mmol). After stirring for 16 h, the reaction mixture was quenched with water. The organic layer was washed with saturated NaCl, collected, and dried over MgSO$_4$. Filtration and concentration provided the crude material as a light pink solid. Trituration with diethyl ether yielded 126 as an off-white solid (20.8 g, 80%): $^1$H NMR (300 MHz, CDCl$_3$) δ•7.69 (br s, 1H), 7.10–7.18 (m, 1H), 6.97–7.07 (m, 3H), 5.55 (br d, 1H), 4.43–4.54 (m, 1H), 3.65–3.71 (m, 1H), 3.49–3.51 (m, 1H), 3.17–3.23 (dd, 1H), 2.60–2.68 (dd, 1H), 1.41 (s, 9H), 0.88–0.97 (m, 1H), 0.49–0.62 (m, 2H), 0.10–0.26 (m, 2H).

Step E: Synthesis of (5-Cyclopropylmethyl-1-methyl-2-oxo-2,3,4,5-tetrahydro-1H-benzo[b][1,5]diazepin-3-yl)-carbamic acid tert-butyl ester, 127 (Scheme C).

2qTo a solution of 126 (18.7 g, 56.4 mmol) and potassium carbonate (93.6 g, 677 mmol) in N,N-dimethylformamide (35 mL) was added iodomethane (35 mL, 564 mmol). After stirring for 16 h at room temperature, the reaction was concentrated under reduced pressure. The crude residue was diluted with ethyl acetate, washed with water, 5% LiCl and saturated NaCl. The organic layer was collected, dried over MgSO$_4$ and concentrated to provided 127 (19.1 g, 98%) as a light yellow solid: mp 226–257° C.; $^1$H NMR (300 MHz, CDCl$_3$) δ•7.11–7.20 (m, 2H), 6.99–7.07 (m, 2H), 5.55–5.63 (br d, 1H), 4.34–4.42 (m, 1H), 3.50–3.58 (dd, 1H), 3.37 (s, 3H), 3.30–3.37 (m, 1H), 3.15–3.22 (dd, 1H), 2.49–2.55 (dd, 1H), 1.40 (s, 9H), 0.81–0.95 (m, 1H), 0.40–0.58 (m, 2H), 0.07–0.20 (m, 2H); IR (ATR) 2976, 1712, 1660, 1498, 1160 cm$^{-1}$; ESI MS m/z 346 [C$_{19}$H$_{27}$N$_3$O$_3$+H]$^+$; [α]$^{25}_D$+42.8° (c 0.10, Methanol); HPLC 99% (area percent), t$_R$=22.59 min.

Step F: Synthesis of 128 (Scheme C).

A solution of 127 (0.057 g, 0.17 mmol) in 1:1 trifluoroacetic acid/methylene chloride (5.8 mL) was stirred at room temperature overnight. The solvent was removed under reduced pressure at 60° C. to afford 128 (0.060 g, >95%) as a pink semisolid: $^1$H NMR (300 MHz, CD$_3$OD) δ 7.41–7.10 (m, 4H), 3.94–3.84 (m, 2H), 3.35 (s [obscured by methanol signal], 3 H), 3.26–3.21 (m, 2 H), 2.60 (m, 1 H), 0.90–0.20 (m, 5 H); APCI MS m/z=246 [C$_{14}$H$_{19}$N$_3$O+H]$^+$.

Example D

Synthesis of (2S, 3R)-2-allyl-3-isobutyl-succinic acid 1-tert-butyl ester; Compound 133

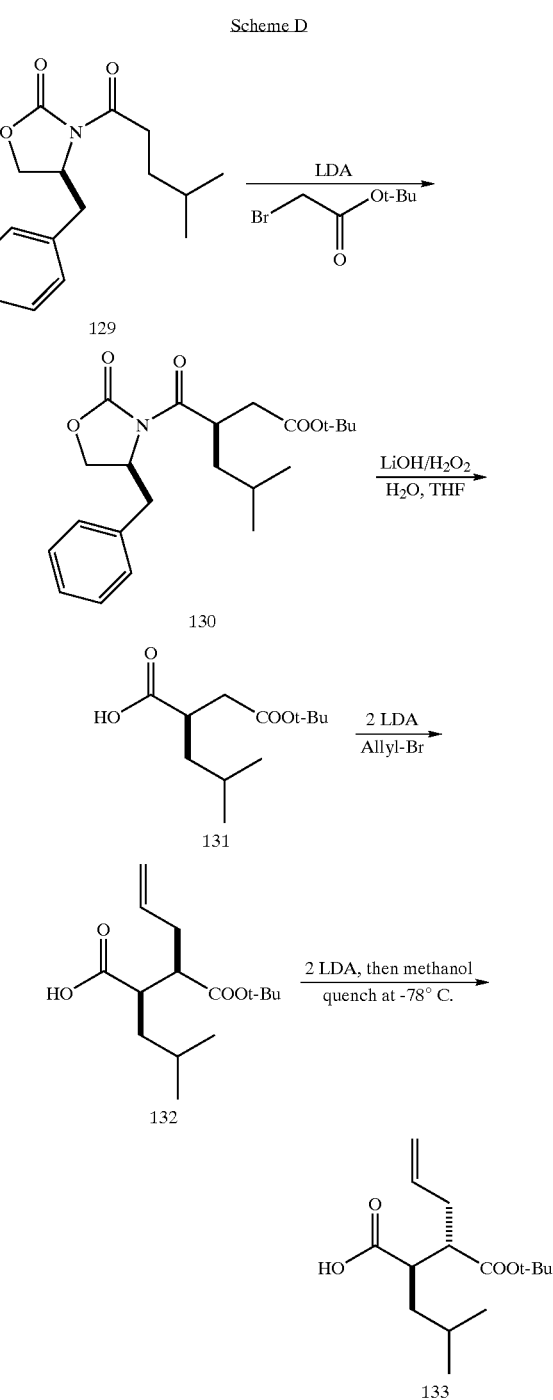

Diastereomerically pure succinate derivatives can be accessed using the chemistry outlined in Scheme D, adapted from P. Becket, M. J. Crimmin, M. H. Davis, Z. Spavold, Synlett, (1993), 137–138 incorporated herein by reference. This reference provides the synthesis of compound 133.

Example 1

4-Methyl-2-(1-propyl-1H-tetrazol-5-ylmethyl)-pentanoic acid[1-methyl-2-oxo-5-(4-trifluoromethylphenyl)-2,3-dihydro-1H-benzo[e][1,4]diazepin-3-yl]-amide, 38

Synthesis of Compound 38:

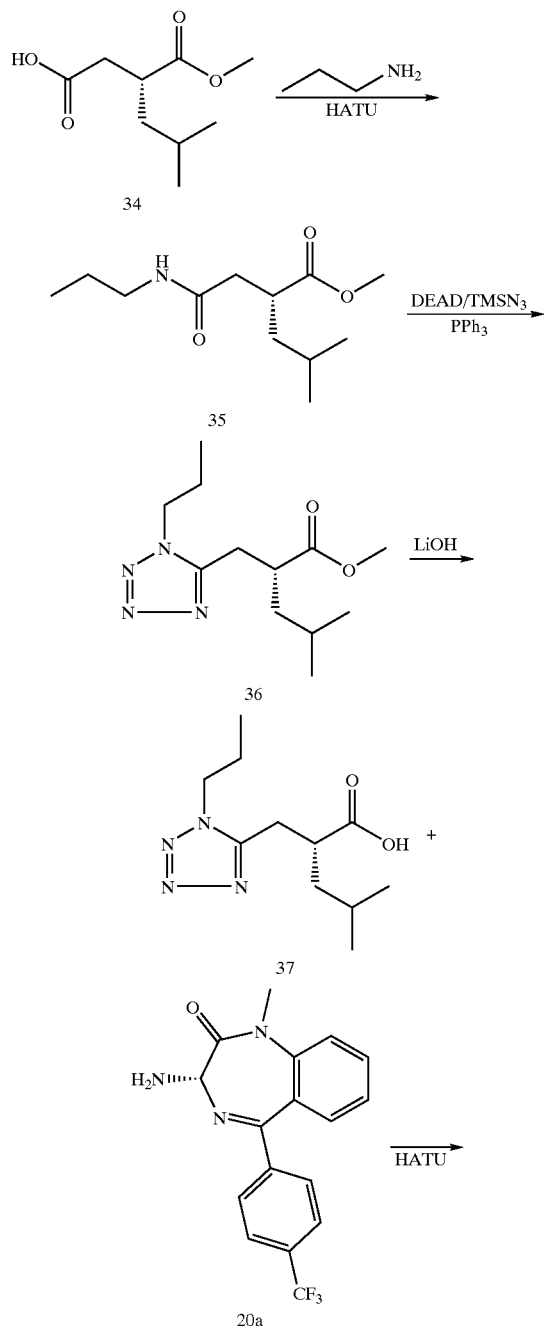

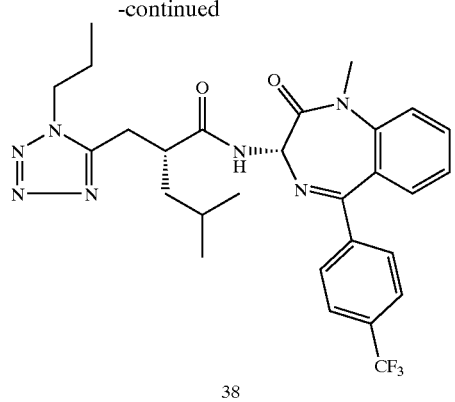

Preferably, the epimerization conditions described in WO 97/18207 and WO 98/51665 are employed.

Step A: Synthesis of (2R)-4-methyl-2-propylcarbamoylmethyl-pentanoic acid methyl ester, 35, (Scheme 20).

Succinate 34, commercially available from Lancaster, (5.3 mmol, 1 g) was taken up in 20 mL anhydrous DMF and treated with HATU (5.8 mmol, 2.2 g) and stirred at room temperature under nitrogen for 15 minutes. The n-propylamine was then added (5.8 mmol, 0.5 mL) followed by Hunig's base (5.8 mmol, 1 mL) and the reaction mixture was stirred at room temperature overnight. The reaction mixture was diluted with ethyl acetate and washed with 5% NaHSO$_4$ followed by saturated NaHCO$_3$ and brine. The organic layer was evaporated in vacuo and the resulting oil purified by flash chromatography using 50% ethyl acetate in hexane to give the desired compound 35 (83%, 1 g). 1H NMR (300 MHz, CDCl$_3$) δ 5.6 (m, 1H), 3.7 (s, 3H), 3.2 (m, 2H), 3.0 (m, 1H), 2.5 (m, 1H), 2.3 (m, 1H), 1.2–1.6 (m, 7H) 0.95 (m, 9H).

Step B: Synthesis of (2R)-4-methyl-2-((1-propyl-1H-tetrazol-5-yl)methyl)-pentanoic acid methyl ester, 36 (Scheme 20)

Amide 35 (0.65 mmol, 150 mg) was taken up in 10 mL of anhydrous THF and treated with triphenyl phosphine (1.64 mmol, 428 mg) followed by trimethylsilyl azide (1.64 mmol, 0.23 mL) and DEAD (1.64 mmol, 0.26 mL). The reaction mixture was stirred 24 hr. at room temperature under a nitrogen atmosphere, then diluted with ethyl acetate and extracted with NaHCO$_3$. The organic layer was separated, concentrated in vacuo and purified by flash chromatography using 50% ethyl acetate in hexane to give the desired compound 36 (58%, 80 mg). The product was obtained as an oil. 1H NMR (300 MHz, CDCl$_3$) δ 4.3 (m, 3H), 3.7 (S, 3H), 3.3 (m, 1H), 3.1 (m, 1H), 2.9 (m, 1H), 2.0 (m, 2H), 1.3–1.8 (m, 4H) 0.95 (m, 9H). MS [M+H]$^+$ 255.

Step C: Synthesis of (2R)-4-methyl-2-((1-propyl-1H-tetrazol-5-yl)methyl)-pentanoic acid, 37 (Scheme 20)

To a solution of tetrazole ester 36 (1.1 g, 4.8 mmol) in 20 mL of THF cooled to 0° C. was added dropwise a solution of lithium hydroxide monohydrate (242 mg, 5.7 mmol) in 5.0 mL of water. The reaction mixture was stirred at room temperature for 16 h. THF was removed under reduced pressure to give a yellow oil which was diluted with 10 mL of 1 N HCl. The aqueous phase was extracted with CH$_2$Cl$_2$ (2×35 mL), and the extracts were combined, dried over Na$_2$SO$_4$, and concentrated to afford 850 mg (98%) of the desired carboxylic acid 37. 1H NMR (300 MHz, CDCl$_3$) δ 4.3 (m, 3H), 3.3 (m, 1H), 3.1 (m, 1H), 2.9 (m, 1H), 1.9 (m, 2H), 1.3–1.8 (m, 4H) 0.95 (m, 9H). MS [M+H]$^+$ 241.

Step D: Synthesis of Title Compound 38 (Scheme 20).

To a solution of the acid 37 (25 mg, 0.1 mmol) in DMF (10 mL) at 0° C. was added HATU (38 mg, 0.1 mmol). The mixture was stirred for 10 min and then amine 20a (43 mg, 0.1 mmol) was added followed by iPrNEt₂ (0.04 mL, 0.2 mmol and stirring was continued for 16 h. The solution was poured into water and the layers separated. The aqueous layer was extracted with EtOAc and the combined extracts were washed with water, 1 N HCl, and sat'd NaHCO₃. The organic layer was dried over magnesium sulfate, concentrated, and purified by flash chromatography to give the title compound 38 as an oil (35 mg, 63%). 1H NMR (300 MHz, CDCl₃) δ 7.6 (m, 4H), 7.2 (m, 4H), 5.4 (d, 1H), 4.2 (m, 2H), 3.4 (s, 3H), 3.32 (m, 1H), 3.1 (m, 1H), 2.9 (m, 1H), 1.9 (m, 2H), 1.7 (m, 2H), 1.2–1.4 (m, 4H) 0.95 (m, 9H). MS [M+H]⁺ 556.

Example 2

4-Methyl-2-[1-(1-propyl-1H-tetrazol-5-yl)-ethyl]-pentanoic acid (5-methyl-6-oxo-6,7-dihydro-5H-dibenzo[b,d]azepin-7-yl)-amide, 44

Synthesis of Compound 44:

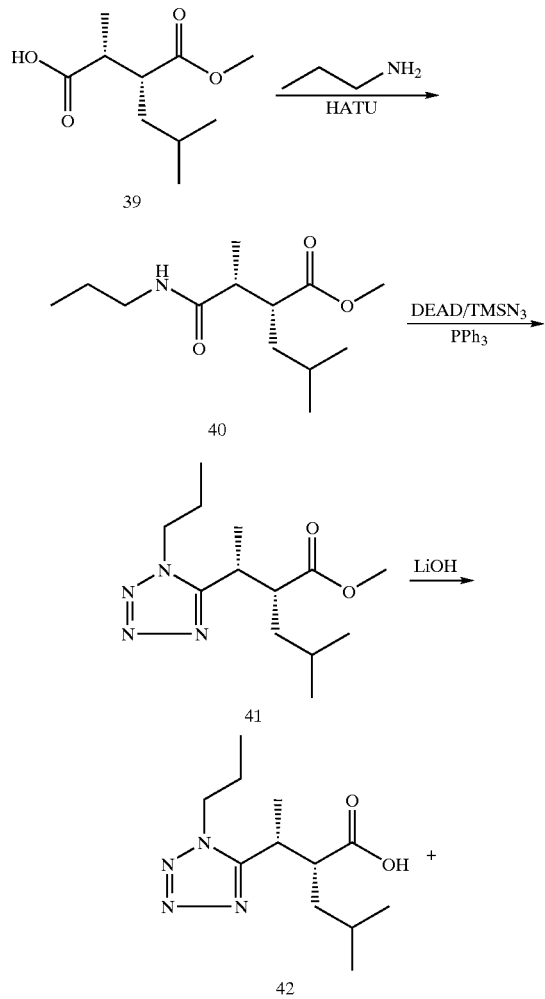

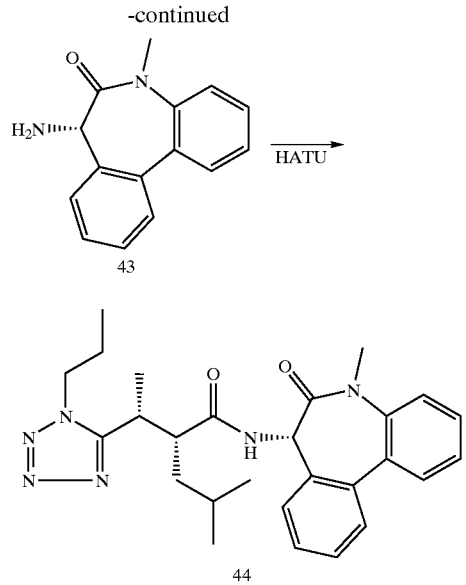

As illustrated in Scheme 21, compound 44 was prepared using the method similar to that described for Example 1. The starting acid, (2R, 3R)-2-isobutyl-3-methyl-succinic acid 1-methyl ester, 39 was made following the procedures described in *Synlett*. 1993, 137, and converted to the corresponding tetrazole 36 using the procedure of Step B, Example 1. The racemic mixture of amino lactam 43 was made following procedures described in PCT publication number WO 99/66934. The desired enantiomer 43 was the first eluting peak as the racemic mixture was separated on CHIRALCEL OD column with 20% iPrOH/Hexane with diethylamine. The product was obtained as an oil. ¹HNMR (300 MHz, CDCl₃) δ 7.6 (d, 1H), 7.25–7.5 (m, 7H), 6.05 (d, 1H), 5.08 (d, 1H), 4.1 (m, 2H), 4.23 (t, 3H), 3,3 (s, 3H), 3.35 (m, 1H), 3.1 (m, 1H), 1.5–1.8 (m, 6H), 1.4 (d, 2H), 1.3 (m, 1H), 1.1 (d, 2H), 0.9 (d, 2H), 0.83 (t, 3H); MS [M+H]⁺ 475.5.

Example 3

4-Methyl-2-[1-(1-propyl-1H-tetrazol-5-yl)-ethyl]-pentanoic acid [1-methyl-2-oxo-5-(4-trifluoromethyl-phenyl)-2,3-dihydro-1H-benzo[e][1,4]diazepin-3-yl]-amide, 45

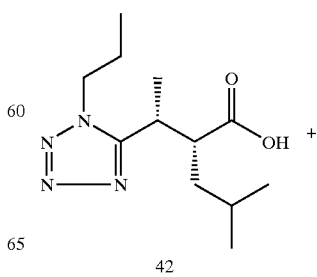

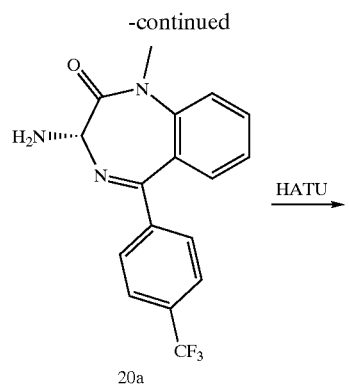

20a

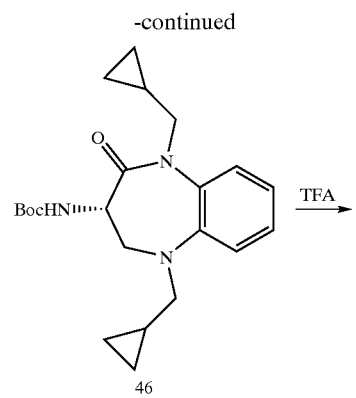

46

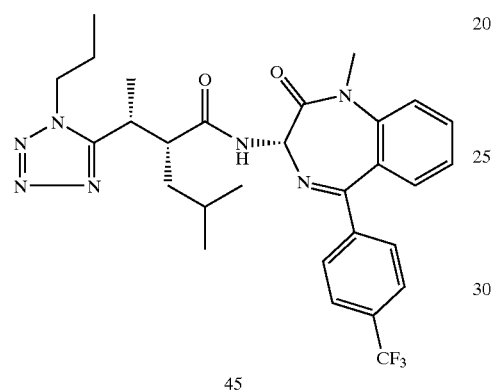

45

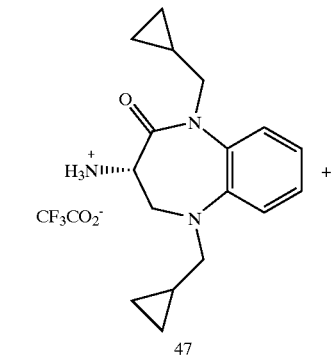

47

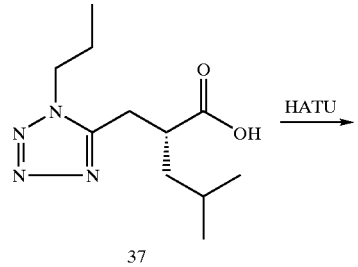

37

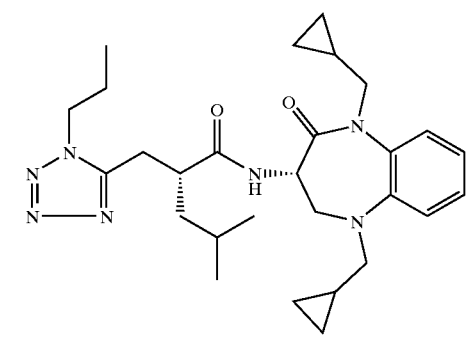

48

As illustrated in Scheme 22, compound 45 was prepared using the method similar to that described for Example 1 starting from (2R)-4-methyl-2-[(1R)-1-(1-propyl-1H-tetrazol-5-yl)-ethyl]-pentanoic acid, 42. $^1$HNMR (300 MHz, CDCl$_3$) δ 7.7 (m, 4H) 7.6 (d, 1H), 7.35 (d, 1H), 7.2–7.3 (m, 4H), 5.25 (d, 1H), 4.23 (t, 2H), 3.4 (s, 3H), 3.25 (m, 1H), 2.9 (m, 1H), 1.9 (m, 2H), 1.5–1.8 (m, 6H), 1.4 (d, 2H), 1.3 (m, 1H), 0.9 (d, 2H), 0.83 (t, 3H); MS[M+H]$^+$ 570.6.

Example 4

4-Methyl-2-(1-propyl-1H-tetrazol-5-ylmethyl)-pentanoic acid (1,5-bis-cyclopropylmethyl-2-oxo-2,3,4,5-tetrahydro-1H-benzo[b][1,5]diazepin-3-yl)-amide, 48

Synthesis of Compound 48:

Scheme 23

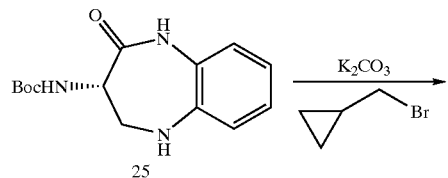

25

Step A: Synthesis of (3S)-(5-cyclopropylmethyl-1-methyl-2-oxo-2,3,4,5-tetrahydro-1H-benzo[b][1,5]diazepin-3-yl)-carbamic acid tert-butyl ester, 46 (Scheme 23)

To a solution of 25 (0.41 g, 1.5 mmol) in DMF (9 mL) was added potassium carbonate (0.82 g, 6.0 mmol). The nonhomogenous mixture was stirred at room temperature under nitrogen for one hour and a solution of bromomethylcyclopropane (0.43 ml, 4.5 mmol) in DMF (0.5 mL) was added. The reaction mixture was stirred at room temperature for 19 hours, then heated to 55° C. for 7 hours. The reaction mixture was cooled to room temperature, and stirring was continued for an additional 22 hours. The reaction mixture was poured into water, and the aqueous layer was extracted with EtOAc. The combined organic extracts were dried over sodium sulfate, filtered, concentrated, and purified using a Biotage Flash 40 chromatography system to give the desired product 46 (0.125 g, 22%) as a white solid. ¹HNMR (300 MHz, CDCl₃) δ 7.20 (m, 2H), 7.17 (m, 2H), 5.60 (d, 1H), 4.36 (m, 1H), 4.19 (dd, 1H), 3.54 (t, 1H), 3.3 (m, 2H), 3.2 (dd, 1H), 2.57 (dd, 1H), 1.4 (s, 9H), 0.85–1.0 (m, 2H), 0.0–0.6 (m, 8H); MS [M+H]⁺386.5.

Step B: Synthesis of (3S)-5-cyclopropylmethyl-1-methyl-2-oxo-2,3,4,5-tetrahydro-1H-benzo[b][1,4]-diazepin-3-yl-ammonium trifluoroacetate, 47 (Scheme 23)

To a solution of 46 (0.46 g, 1.2 mmol) in DCM (8 mL) was added trifluoroacetic acid (2 mL). The reaction mixture was stirred at room temperature under nitrogen for two hours, then concentrated on the rotavapor. The residue was re-dissolved in EtOAc and poured into sat'd NaHCO₃. The aqueous layer was extracted with EtOAc. The combined extracts were dried with sodium sulfate, filtered, and concentrated on the rotavapor, giving the desired product 47 (0.33 g, 98%) as a yellow solid. ¹HNMR (300 MHz, CDCl₃) δ 7.0 (m, 2H), 6.85 (m, 2H), 4.00 (dd, 1H), 3.28 (m, 2H), 3.10 (dd, 1H), 2.9 (m, 2H), 2.35 (dd, 1H), 0.70–0.85 (m, 2H), 0.0–0.6 (m, 8H); MS [M+H]⁺ 286.4.

Step C: Synthesis of Title Compound, 48 (Scheme 23)

To a solution of acid 37 (0.16 g, 0.67 mmol) in DMF (15 mL) at room temperature was added HATU (0.28 g, 0.74 mmol). The mixture was stirred for 15 min and then amine 47 (0.19 g, 0.67 mmol) was added followed by iPrNEt₂ (0.12 mL, 0.67 mmol). Stirring was continued for 24 hours. The solution was poured into sat'd NaHCO₃ and the aqueous layer was extracted with EtOAc. The combined extracts were dried with sodium sulfate, filtered, concentrated, and purified using a Biotage Flash 40 chromatography system to give the desired product 48, Example 4 (0.2 g, 59%) as a white solid. ¹HNMR (300 MHz, CDCl₃) δ 7.20 (m, 2H), 7.15 (m, 2H), 6.40 (d, 1H), 4.5 (m, 1H), 4.19 (dd, 3H), 3.54 (m, 2H), 3.0–3.1 (m, 3H), 2.85 (m, 1H), 2.5 (dd, 1H), 1.9 (q, 2H), 1.6–1.7 (m, 3H), 1.3 (m, 1H), 0.85–1.0 (m, 1H), 0.0–0.6 (m, 8H); MS [M+H]⁺ 508.6.

Example 5

4-Methyl-2-(1-propyl-1H-tetrazol-5-ylmethyl)-pentanoic acid (1-cyclopropylmethyl-2-oxo-2,3,4,5-tetrahydro-1H-benzo[b][1,5]diazepin-3-yl)-amide, 51

Synthesis of Compound 51:

Scheme 24

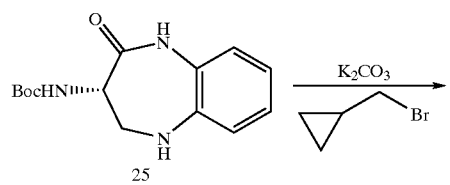

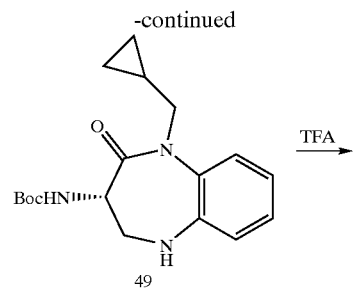

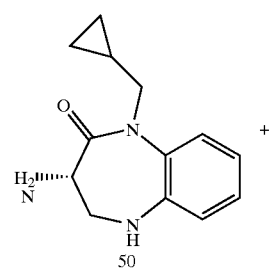

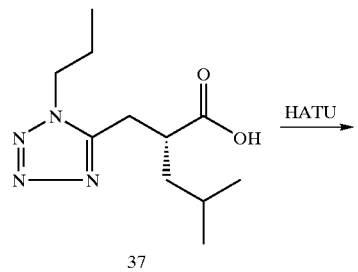

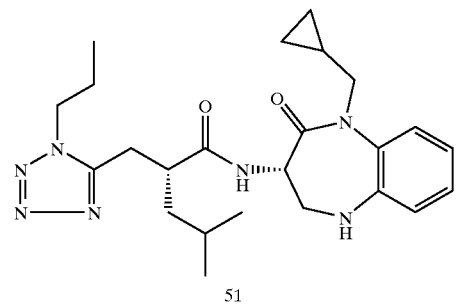

Step A: Synthesis of 49 (Scheme 24)

To a solution of 25 (0.41 g, 1.5 mmol) in DMF (9 mL) was added potassium carbonate (0.82 g, 6.0 mmol). The nonhomogenous mixture stirred at room temperature under nitrogen for one hour and a solution of bromomethyl-cyclopropane (0.43 ml, 4.5 mmol) in DMF (0.5 mL) was added. The reaction mixture was stirred at room temperature for 19 hours, then heated to 55° C. for 7 hours. The reaction mixture was cooled to room temperature, and stirring was continued for an additional 22 hours. The reaction mixture was poured into water, and aqueous layer was extracted with EtOAc. The combined organic extracts were dried over sodium sulfate, filtered, concentrated, and purified using a Biotage Flash 40 chromatography system to give the desired product 49 (0.3 g, 61%) as an oil. $^1$HNMR (300 MHz, CDCl$_3$) δ 7.17 (m, 1H), 7.05 (m, 1H), 6.95 (m, 1H), 6.80 (m, 1H), 5.60 (d, 1H), 4.50 (m, 1H), 4.00 (m, 1H), 3.90 (m, 1H), 3.40 (m, 3H), 1.40 (s, 9H), 1.00 (m, 1H), 0.40 (m, 2H), 0.20 (m, 1H), 0.05 (m, 1H); MS [M+H]$^+$ 332.

Step B: Synthesis of 50 (Scheme 24)

To a solution of 49 (0.28 g, 0.84 mmol) in DCM (8 mL) was added trifluoroacetic acid (2 mL). The reaction mixture was stirred at room temperature under nitrogen for two hours, then concentrated on the rotavapor. The residue was re-dissolved in EtOAc and poured into sat'd NaHCO$_3$. The aqueous layer was extracted with EtOAc. The combined extracts were dried with sodium sulfate, filtered, and concentrated on the rotavapor, giving the desired product 50 (0.15 g, 77%) as a yellow solid. $^1$HNMR (300 MHz, CDCl$_3$) δ 7.17 (m, 1H), 7.05 (m, 2H), 4.00 (m, 1H), 3.80 (m, 1H), 3.65 (m, 1H), 3.50 (m, 1H), 3.25 (m, 1H), 1.02 (m, 1H), 0.40 (m, 2H), 0.20 (m, 1H), 0.05 (m, 1H); MS [M+H]$^+$ 232.

The title compound 51, Example 5, was prepared using the procedure of Step C, Example 4. The product was obtained as an oil. $^1$HNMR (300 MHz, CDCl$_3$) δ 7.16 (d, 1H), 7.08 (t, 1H), 7.0 (t, 1H), 6.84 (d, 1H), 6.50 (d, 1H), 4.65 (m, 1H), 4.23 (t, 3H), 4.08 (q, 1H), 3.54 (dd, 1H), 3.43 (dd, 1H), 3.0–3.2 (m, 3H), 2.85 (m, 1H), 1.9 (q, 1H), 1.55–1.73 (m, 3H), 1.6–1.7 (m, 2H), 1.38 (m, 1H), 0.85–1.0 (m, 10H), 0.0–0.48 (m, 4H); MS [M+H]$^+$ 454.5.

Example 6

4-Methyl-2-(1-propyl-1H-tetrazol-5-ylmethyl)-pentanoic acid (1-cyclopropylmethyl-5-methyl-2-oxo-2,3,4,5-tetrahydro-1H-benzo[b][1,5]diazepin-3-yl)-amide, 52

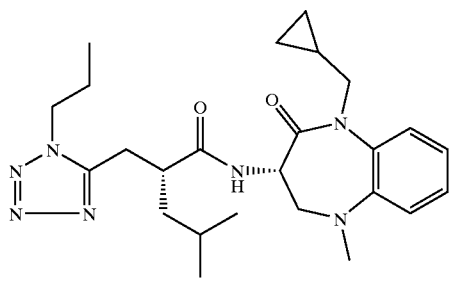

52

To a solution of 51 (20 mg) in DMF under nitrogen was added K$_2$CO$_3$ (5 equivalents) followed by methyl iodide (4 equivalents). The reaction mixture was stirred at room temperature for 16 hours before water and EtOAc were added. The organic layer was separated, dried over sodium sulfate and concentrated in vacuo. The crude product was passed through a pad of silica gel (1:1 ethyl acetate/methylene chloride) to give, after removal of solvent, 52 as an oil. $^1$HNMR (300 MHz, CDCl$_3$) δ 7.19 (m, 2H), 7.08 (m, 2H), 6.65 (d, 1H), 4.45 (m, 1H), 4.23 (t, 2H), 4.08 (q, 1H), 2.9–3.1 (m, 3H), 2.8 (m, 1H), 2.7 (s, 3H), 1.9 (q, 2H), 1.6 (m, 2H), 0.9–1.0 (m, 9H), 0.3 (m, 2H) 0.2 (m, 1H), 0.0 (m, 1H); MS [M+H]$^+$ 468.5.

Example 7

4-Methyl-2-[1-(1-propyl-1H-tetrazol-5-yl)-ethyl]-pentanoic acid (1,5-bis-cyclopropylmethyl-2-oxo-2,3,4,5-tetrahydro-1H-benzo[b][1,4]diazepin-3-yl)-amide, 53

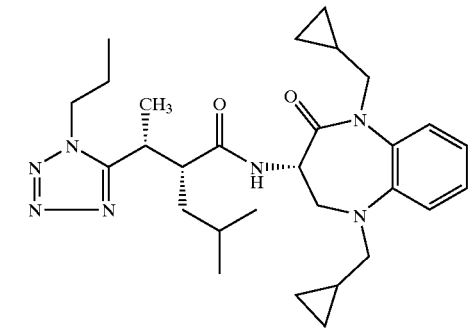

53

The title compound 53 was prepared using the procedure of Step C, Example 4, except that acid 42 and amine 47, prepared as described in Schemes 21 and 23, respectively, were used as starting materials. The product was obtained as an oil. $^1$HNMR (300 MHz, CDCl$_3$) δ 7.1 (m, 2H), 7.00 (t, 2H), 6.50 (d, 1H), 4.06–4.3 (m, 4H), 2.82–3.25 (m, 4H), 2.35–2.7 (m, 3H) 1.82 (q, 2H), 1.3–1.65 (m, 5H), 0.75–1.0 (m, 11H), 0.0–0.57 (m, 8H); MS [M+H]$^+$ 522.6.

Example 8

2-[Amino-(1-propyl-1H-tetrazol-5-yl)-methyl]-4-methyl-pentanoic acid [1-methyl-2-oxo-5-(4-trifluoromethyl-phenyl)-2,3-dihydro-1H-benzo[e][1,4]diazepin-3-yl]-amide, 56

Synthesis of Compound 56:

Scheme 25

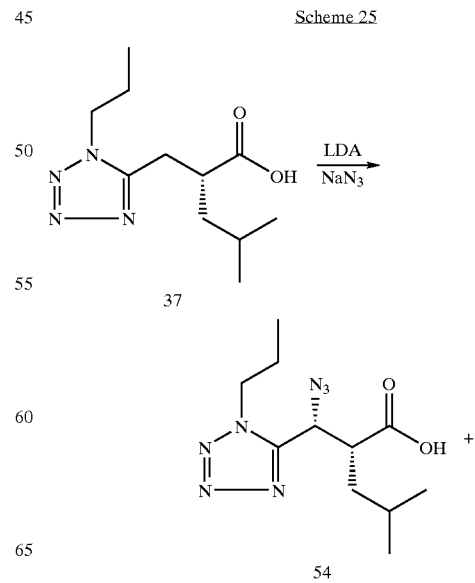

-continued

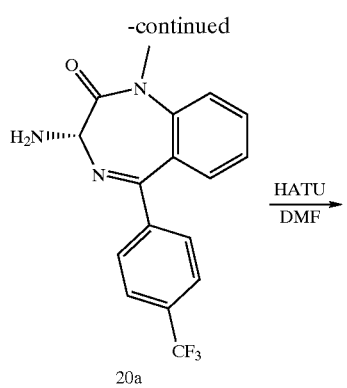

Step B: Synthesis of Title Compound, 56 (Scheme 25)

A typical peptide coupling reaction condition was used to couple acid 54 and amine 20a and provided compound 55 which was subsequently converted to title compound 56 under reaction conditions of $H_2$/Pd. The product was obtained as an oil. $^1$HNMR (300 MHz, CDCl$_3$) δ 7.9 (m, 1H) 7.68 (m, 3H), 7.6 (m, 1H), 7.4 (d, 1H), 7.2–7.3 (m, 3H), 5.36 (d, 1H), 4.39 (m, 1H), 4.3 (m, 2H), 3.42 (s, 3H), 3.07 (m, 1H), 2.95 (m, 1H), 1.6–2.1 (m, 6H), 0.95 (m, 9H); MS[M+H]$^+$ 571.4.

Example 9

2-Isobutyl-3-(1-methyl-1H-tetrazol-5-yl)-hex-5-enoic acid (5-cyclopropylmethyl-1-methyl-2-oxo-2,3,4,5-tetrahydro-1H-benzo[b][1,4]diazepin-3-yl)-amide, 61

Synthesis of Compound 61:

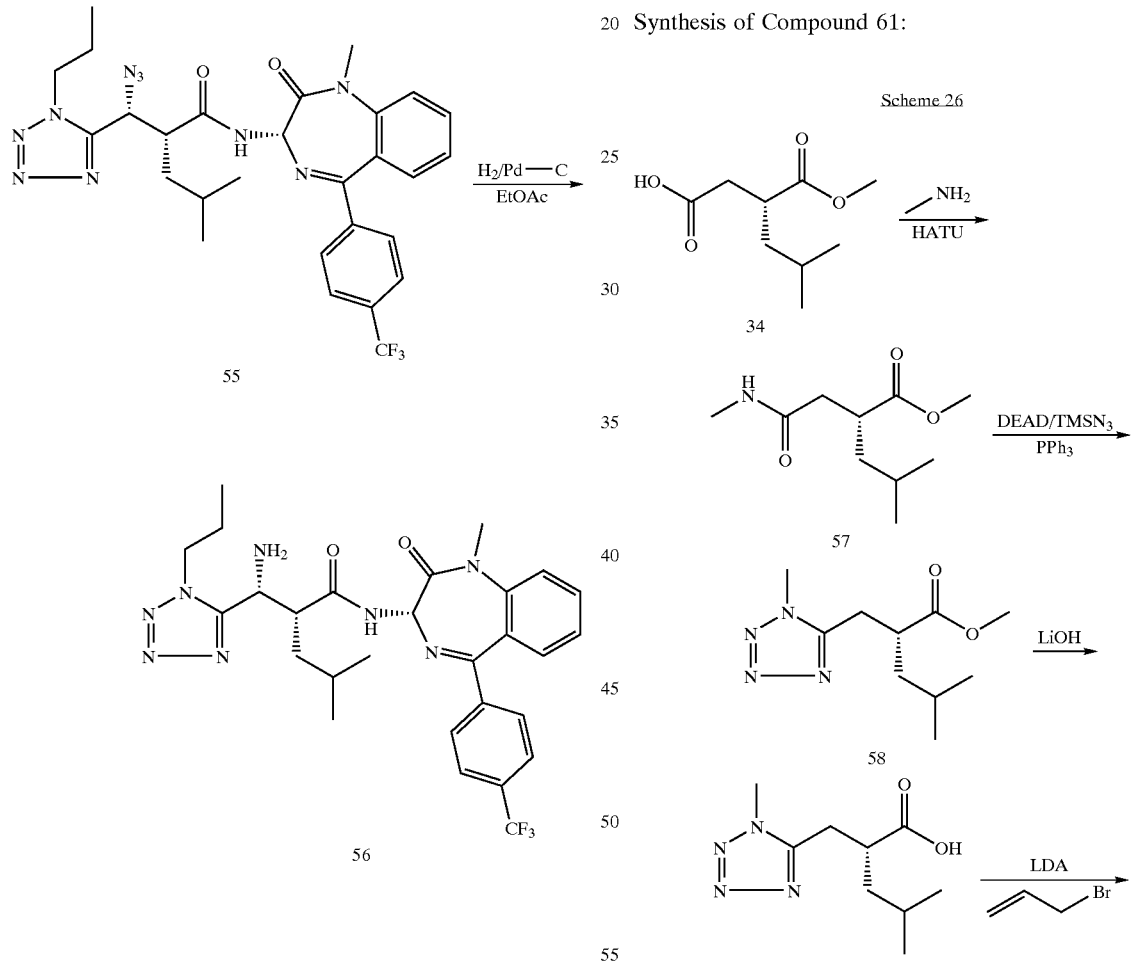

Step A: Synthesis of (2R)-2-[(R)-azido-(1-propyl-1H-tetrazol-5-yl)-methyl]-4-methyl-pentanoic acid, 54 (Scheme 25)

To a solution of acid 37 (100 mg, 0.42 mmol) in THF (5 mL) at −78° C. was added LDA (0.52 mL, 1.04 mmol), 30 minutes later, followed by sodium azide (0.5 mmol). The reaction mixture was allowed to warm to room temperature over 20 hours, then diluted with Et$_2$O and H$_2$O. The aqueous layer was collected, acidified to pH=3 with 1N HCl, and extracted with ethyl acetate. The combined organic layers were dried over Na$_2$SO$_4$, filtered, and concentrated in vacuo to give 54 in 52% yield.

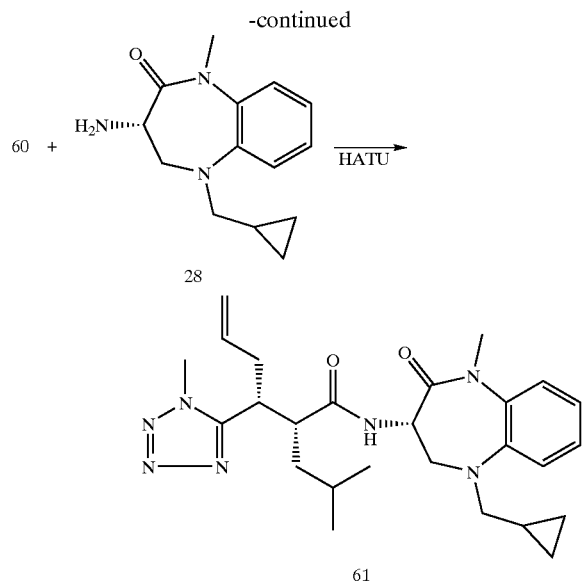

Step A: Synthesis of (2R)-4-Methyl-2-(methylcarbamoyl-methyl)-pentanoic Acid Methyl Ester, 57 (Scheme 26).

The acid 34, commercially available from Lancaster, (5.3 mmol, 1 g) was taken up in 20 mL anhydrous DMF and treated with HATU (5.8 mmol, 2.2 g) and stirred at room temperature under nitrogen for 15 minutes. Methylamine, as a solid, was added (5.8 mmol) followed by Hunig's base (5.8 mmol, 1 mL) and the reaction mixture was stirred at room temperature overnight, diluted with ethyl acetate, and washed with 5% NaHSO$_4$, saturated NaHCO$_3$ and brine. The organic layer was evaporated in vacuo and the resulting oil purified by flash chromatography using 50% ethyl acetate in hexane to give the desired compound 57 (83%, 1 g).

Step B: Synthesis of (2R)-4-methyl-2-((1-methyl-1H-tetrazol-5-yl)methyl)-pentanoic Acid, 59 (Scheme 26).

The starting material 57 (0.65 mmol, 150 mg) was taken up in 10 mL of anhydrous THF and treated with triphenyl phosphine (1.64 mmol, 428 mg) followed by trimethylsilyl azide (1.64 mmol, 0.23 mL) and DEAD (1.64 mmol, 0.26 mL). The reaction mixture was stirred 24 hr. at room temperature under a nitrogen atmosphere, then diluted with ethyl acetate and extracted with NaHCO$_3$. The organic layer was separated, dried in vacuo and the resulting orange oil was purified by flash chromatography using 50% ethyl acetate in hexane to give the (2R)-4-methyl-2-((1-methyl-1H-tetrazol-5-yl)methyl)-pentanoic acid methyl ester, 58. Conversion to the title compound 59 was accomplished using lithium hydroxide monohydrate in THF following the procedures of Example 1, Step C.

Step C: Synthesis of Title Compound, 61 (Scheme 26).

To a solution of acid 59 (100 mg, 0.42 mmol) in THF (5 mL) at −78° C. was added LDA (0.52 mL, 1.04 mmol) followed in 30 minutes by allyl bromide (0.5 mmol). The reaction mixture was stirred for 20 h and allowed to warm to rt then diluted with by Et$_2$O and H$_2$O. The aqueous layer was collected, acidified to pH=3 with 1N HCl, and extracted with ethyl acetate. The combined organic layers were dried over Na$_2$SO$_4$, filtered, and concentrated in vacuo to give (2R, 3R)-2-isobutyl-3-(1-methyl-1H-tetrazol-5-yl)-hex-5-enoic acid, 60, in 40% yield. The intermediate 60 was coupled to amine 28 using HATU to give the title compound 61. The product was obtained as an oil.

$^1$HNMR (300 MHz, CDCl$_3$) δ 6.9–7.11 (m, 2H), 6.9–7.0 (m, 2H), 6.5 (d, 1H), 5.41 (m, 1H), 4.90 (m, 2H), 4.25 (m, 1H), 3.85 (s, 3H), 3.25 (s, 3H), 2.83–3.1 (m, 3H), 2.7 (m, 1H), 2.4–2.6 (m, 4H), 1.6 (t, 1H), 1.2 (m, 2H), 0.9 (d, 3H), 0.83 (t, 3H), 0.8 (m, 1H), 0.53 (m, 1H), 0.42 (m, 1H), 0.1 (m, 2H); MS[M+H]$^+$ 480.4.

Example 10

2-Isobutyl-4-methyl-3-(1-methyl-1H-tetrazol-5-yl)-pentanoic Acid (5-cyclopropylmethyl-1-methyl-2-oxo-2,3,4,5-tetrahydro-1H-benzo[b][1,4]diazepin-3-yl)-amide, 63

Synthesis of Compound 63:

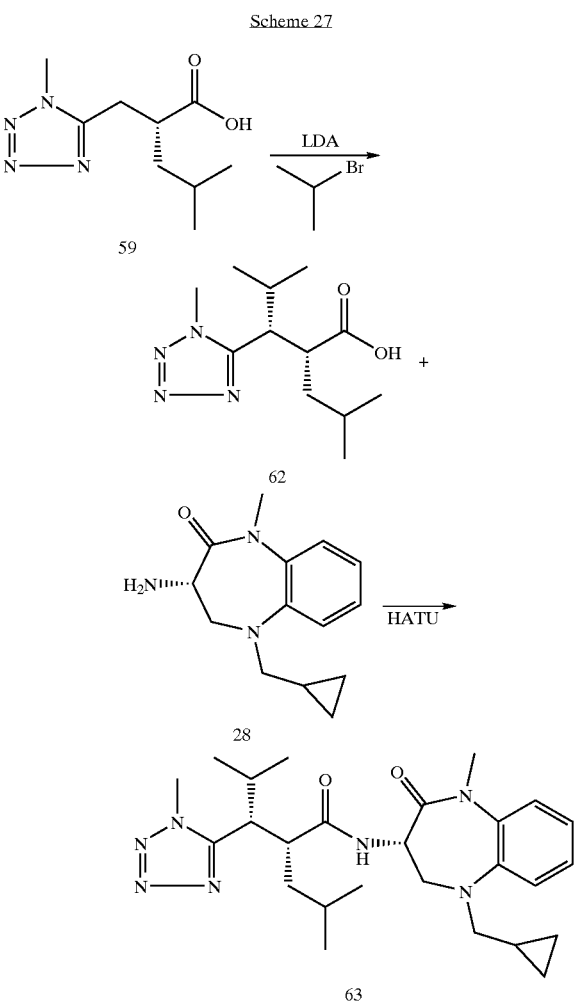

Scheme 27

The title compound 63 was prepared using the procedures of Example 9, step C, except isopropyl bromide was used as the starting material instead of allyl bromide in the synthesis of (2R, 3R)-2-isobutyl-4-methyl-3-(1-methyl-1H-tetrazol-5-yl)-pentanoic acid, 62. The product 63 was obtained as an oil. $^1$HNMR (300 MHz, CDCl$_3$) δ 6.98–7.11 (m, 2H), 6.9–7.0 (m, 2H), 6.5 (d, 1H), 4.25 (m, 1H), 3.88 (s, 3H), 3.25 (s, 3H), 2.96 (dd, 1H), 2.8–2.9 (m, 2H), 2.4–2.51 (m, 2H), 2.25 (m, 1H), 1.3–1.6 (m, 2H), 1.03 (d, 3H), 0.92 (d, 3H), 0.81 (d, 3H), 0.80 (m, 1H), 0.68 (d, 3H), 0.58 (m, 1H), 0.23 (m, 1H), 0.1 (m, 2H); MS[M+H]$^+$ 482.4

Utility

Aβ production has been implicated in the pathology of Alzheimer's Disease (AD). The compounds of the present invention as well as compounds determined from the present invention have utility for the prevention and treatment of AD by inhibiting the proteolytic activity leading to Aβ production. Methods of treatment target formation of Aβ production through the enzymes involved in the proteolytic processing of β amyloid precursor protein. Compounds that inhibit γ secretase activity, either directly or indirectly, control the production of Aβ. Such inhibition of γ secretases reduces production of Aβ, and is expected to reduce or prevent the neurological disorders associated with Aβ peptide, such as Alzheimer's Disease.

Multiple lines of evidence together strongly suggest that a reduction in brain Aβ levels will prevent the onset and progression of Alzheimer's disease (AD). First, Aβ is a major constituent of the parenchemyal plaques observed in all AD patients and the cerebral vasculature amyloid deposits observed in 90% AD patients (reviewed in (Selkoe 2001; Wolfe 2001)). These plaques are formed from the aggregation of soluble Aβ whose brain levels are highly correlated with the severity of AD neurodegeneration (McLean, Cherny et al. 1999). Second, mutations in three genes (APP, PS-1, or PS-2) that increase Aβ cause familial AD (FAD), where AD onset is accelerated by at least a decade. Included in the mutations that increase Aβ are chromosome 21 trisomy that causes Down's syndrome. Third, transgenic mice that express one or more of the mutant FAD genes have increased Aβ levels, form parenchymal plaques and cerebral vascular deposits containing Aβ, exhibit memory deficits reminiscent of AD patients (Chapman, White et al. 1999), and enhance neurofibrillary degeneration in mice that also overexpress mutant tau (Lewis, Dickson et al. 2001). Fourth, Aβ is toxic to cultured cells (Dahlgren, Manelli et al. 2002), induces neurofibrillary tangles in mice with mutant tau (Gotz, Chen et al. 2001), and interferes with long-term potentiation, a likely component of memory ((Walsh, Klyubin et al. 2002) and references therein). Taken together, these data lead one skilled in the art to conclude that excess Aβ production and/or reduced Aβ clearance cause AD. From this it follows that reducing brain Aβ levels by inhibition of γ-secretase will prevent the onset and progression of Alzheimer's disease.

Cellular screening methods for inhibitors of Aβ production, testing methods for the in vivo suppression of Aβ production, and assays for the detection of secretase activity are known in the art and have been disclosed in numerous publications, including PCT publication number WO 98/22493, EPO publication number 0652009, U.S. Pat. No. 5,703,129 and U.S. Pat. No. 5,593,846; all hereby incorporated by reference.

The compounds of the present invention as well as compounds determined from the present invention have utility for the prevention and treatment of disorders involving Aβ production, such as cerebrovascular disorders.

Compounds of Formula (I) are expected to possess γ-secretase inhibitory activity. The γ-secretase inhibitory activity of the compounds of the present invention is demonstrated using assays for such activity, for example, using the assay described below. Compounds within the scope of the present invention have been shown to inhibit the activity of γ-secretase, as determined using assays for such activity.

Compounds provided by this invention should also be useful as standards and reagents in determining the ability of a potential pharmaceutical to inhibit Aβ production. These would be provided in commercial kits comprising a compound of this invention.

As used herein "μg" or "ug" denotes microgram, "mg" denotes milligram, "g" denotes gram, "μL" denotes microliter, "mL" denotes milliliter, "L" denotes liter, "nM" denotes nanomolar, "μM" or "uM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetate.

In Vitro Binding Assay to Identify γ-Secretase Inhibitors.

Competitive binding assays can be used to identify molecules that inhibit the binding of a radiolabeled γ-secretase inhibitor and therefore inhibit γ-secretase activity. For example, [$^3$H]-Compound A can be used for binding assays with membranes from THP-1 cells (Seiffert, Bradley et al. 2000). Compound A is (2R, 3S) N1-[(3S)-hexahydro-1-(3-phenoxybenzyl)-2-oxo-1H-azepin-3-yl]-2-(2-methylpropyl)-3-(propyl)-butanediamide:

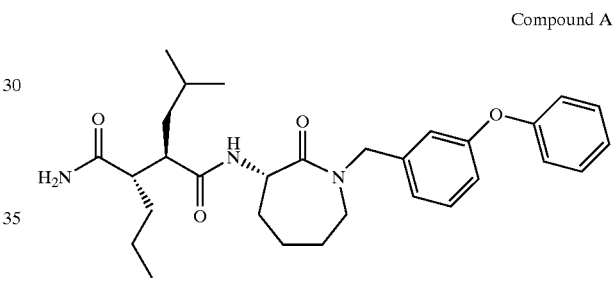

Compound A the synthesis of which is described in U.S. Pat. No. 6,331,408 (Dec. 18, 2001); PCT Publication WO 00/28331; PCT Publication WO 00/07995; and Seiffert, Bradley et al. 2000.

For these assays, THP-1 cells were grown in spinner cultures in RPMI 1640 containing L-glutamine and 10 μM β-mercaptoethanol to a density of 5×10$^5$ cells/ml. Cells were harvested by centrifugation and cell pellets were quick frozen in dry ice/ethanol and stored at −70° C. prior to use. The pellets of approximately 2×10$^4$ THP-1 cells were homogenized using a Brinkman Polytron at setting 6 for 10 sec. The homogenate was centrifuged at 48,000×g for 12 min, and the resulting pellet was washed by repeating the homogenization and centrifugation. The final cell pellet was resuspended in buffer to yield a protein concentration of approximately 0.5 mg/ml. Assays were initiated by the addition of 150 μl of membrane suspension to 150 μl of assay buffer containing 0.064 μCi of radioligand and various concentrations of unlabeled compounds. Binding assays were performed in duplicate in polypropylene 96-well plates in a final volume of 0.3 ml containing 50 mM Hepes, pH 7.0, and 5% dimethyl sulfoxide. Nonspecific binding was defined using incubations with 300 nM compound E (Seiffert, Bradley et al. 2000). After incubating at 23° C. for 1.3 hr, bound ligand was separated from free radioligand by filtration over GFF glass fiber filters presoaked in 0.3% ethyleneimine polymer solution. Filters were washed three times with 0.3 ml of ice cold phosphate-buffered saline, pH 7.0, containing 0.1% Triton X-100. Filter-bound radioactivity was measured by scintillation counting. $IC_{50}$ values were then determined and used to calculate $K_i$ values using the Cheng-Prusoft correction for $IC_{50}$ values.

Compounds were scored as active γ-secretase inhibitors if $K_i$ values were less than 10 μM. Compounds of the present invention have been demonstrated to have an $IC_{50}$ value less than 10 μM in the above assay.

In Vitro Assay to Identify γ-Secretase Inhibitor Based on the Inhibition of Aβ Formation from Membrane Preparations.

In this method, an isolated membrane fraction is used to generate APP cleavage products, including Aβ, that are dependent upon γ-secretase. Inhibition of formation of these cleavage products therefore provides a sensitive assay for γ-secretase inhibitors. Membranes are typically prepared at 4° C. from human derived cell lines, such as HeLa and H4, which normally express APP and γ-secretase or have been transfected with wild-type APP, mutant forms of APP, or an APP fusion protein. When these membranes are incubated at 37° C., APP substrates are cleaved (Shearman, D et al. 2000; Zhang, Song et al. 2001). For instance, H4 neuroglioma cells were engineered to express a fusion protein that contained residues 1–495 of human placental alkaline phosphatase (HPLAP) fused to the C-terminal 164 residues of APP (Felsenstein, Hunihan et al. 1994). To express this fusion protein, a genomic clone that encoded 1–495 amino acids of HPLAP was joined in frame to a cDNA fragment that encoded the C-terminal 164 residues of APP in the mammalian expression vector pRcCMV (Invitrogen). The resulting plasmid was transfected into H4 cells by the calcium phosphate method and stable clones expressing the fusion protein were isolated. The resulting cells were grown in Dulbecco's Modified Eagle Medium supplemented with 10% fetal bovine serum and 1% glutamine in tissue culture flasks, detached, and collected by centrifugation at 1000×g for 10 min at 4° C. Cells were first washed with PBS (50× pellet volume) and then with ice-cold lysis buffer (0.25 M sucrose, 20 mM Hepes, pH 7.2). Cells were then broken by dounce homogenization (95% cells disrupted) in lysis buffer using 50× lysis buffer per pellet volume. Nuclei were removed by centrifugation for 1000×g for 10 min at 4° C. The resulting post nuclear supernatant was then centrifuged at 12,000×g for 30 min at 4° C. The pellet was resuspended in 20% glycerol, 20 mM Hepes, pH 7.2, 1 mM 1,10 phenanthroline, 10 μg/ml leupeptin, frozen in liquid nitrogen, and stored at −80° C. until needed. For reactions, the crude membrane fraction was diluted 10-fold in ice-cold wash buffer (50 mM Hepes, pH 7.4, 1 M NaCl, 10% glycerol, 10 μg/ml leupeptin, 1 mM 1,10 phenanthroline) and then collected by centrifugation at 16,500×g for 20 min at 4° C. Membranes were washed again and then resuspended in reaction buffer (50 mM Hepes, pH 7.4, 10% glycerol) so that the protein concentration was 1.5 mg/ml. Reactions containing 30 μL of washed membranes were then incubated with 5 μl diluted compound in 10% DMSO for 90 min at 37° C. After this incubation, 120 μl ice-cold PBS, 1% BSA was added to the reaction, vortexed, and then centrifuged at 6000×g for 45 min at 4° C. 100 μl of this supernatant was then removed to measure product formation. Aβ was detected using time-resolved fluorescence of the homogenous sample (Shearman, D et al. 2000). In this method, one antibody recognizes an epitope that is present in Aβ but not present in the precursor fragments; preferably the antibody binds the carboxyl terminus of Aβ generated by γ-secretase cleavage. The second antibody binds to another epitope present on Aβ. For example, antibodies that bind the N-terminal region, such as 26D6-B2-B3, or the C-terminal end, such as 9S3.2, of the Aβ peptide are known (Roberts, et al., WO 01/75435). The antibodies were labeled with a pair of fluorescent adducts that transfer fluorescent energy when the adducts are brought in close proximity as a result of binding to the N-and C-terminal ends or regions of Aβ. In particular, 26D6-B2-B3 was coupled with cross-linked allophycocyanin (XL665® Packard Biosciences) and 9S3.2 was coupled with europium cryptate using standard coupling chemistry (Harlow and Lane 1988). To measure Aβ levels, 60 μl of conjugated 26D6-B2-B3 at 0.8 μg/ml, 60 μl of conjugated 9S3.2 at 0.3 μg/ml, and 20 μl of reaction supernatant containing an unknown amount of Aβ, were incubated for 18 to 24 hrs at room temperature. The ratio of the fluorescence signals at 665 nm and 620 nm were then measured with a Discovery HTRF microplate analyzer (Packard Instrument Company, Meriden, Conn.). By comparison of the ratio of the fluorescence signals to control fluids that contained known amounts of Aβ, the amount of Aβ and hence the extent of Aβ inhibition was determined. Compounds were judged to be γ-secretase inhibitors if they inhibited Aβ production by 50% or more at 50 μM. Compounds of the present invention have been demonstrated to have an $IC_{50}$ value less than 50 μM in the above assay. Detection of Aβ and other cleavage products can also be monitored by other methods, such as immunoprecipitation of radiolabeled proteins (Shearman, D et al. 2000; Dovey, John et al. 2001), immunoprecipitation followed by mass spectroscopy (Shearman, D et al. 2000; Zhang, Song et al. 2001), western blotting (Zhang, Song et al. 2001), and enzyme-linked immunosorbent assay (Seiffert, Bradley et al. 2000; Dovey, John et al. 2001; Zhang, Song et al. 2001).

In Vitro Assays to Identify γ-Secretase Inhibitor Based on the Inhibition of Aβ Formation in Cultured Cells.

Cultured human cell lines, such as HEK293 and H4 cells, which express APP and γ-secretase activity or transfected derivative cell lines that overexpress wild-type APP, mutant APP, or APP fusion proteins will secrete Aβ peptides into the culture media that can be quantified as previously outlined (Dovey, John et al. 2001). The incubation of these cultured cells with γ-secretase inhibitors decreases the production of Aβ peptides. For instance, H4 cells stably transfected to overexpress the HPLAP-APP fusion protein described above were grown as above, detached, and adjusted to $2 \times 10^5$ cells/ml. 100 μl of the resulting suspension was then added to each well of a 96-well plate. After 4 hrs, the media was removed and replaced with 100 μl serum-free media containing various dilutions of the test compound. Plates were then incubated for 18 hrs at 37° C. and a 100 μl aliquot of the tissue culture supernatant was removed for determination of Aβ levels using time-resolved fluorescence of the homogenous sample as outlined above. Alternately, the other methods described above for Aβ determination could be used. The extent of Aβ inhibition was used to calculate the $IC_{50}$ value for the test compound.

Compounds of the present invention are considered active when tested in the above assay if the $IC_{50}$ value for the test compound is less than 50 μM. A preferred $IC_{50}$ value is less than 1 μM. A more preferred $IC_{50}$ value is less than 0.1 μM. Compounds of the present invention have been demonstrated to have an $IC_{50}$ value less than 50 μm in the above assay.

In addition to cleaving APP, γ-secretase cleaves other substrates, including: the Notch family of transmembrane receptors (reviewed in (Selkoe 2001; Wolfe 2001)); LDL receptor-related protein (May 2002); ErbB-4 (Ni 2001); E-cadherin (Marambaud 2002); and CD44 (Okamoto 2001).

If inhibition of cleavage of non-APP substrates causes undesirable effects in humans, then desired γ-secretase inhibitors would preferentially inhibit APP cleavage relative to unwanted substrates. Notch cleavage can be monitored directly by measuring the amount of cleavage product or indirectly by measuring the effect of the cleavage product on transcription (Mizutani, Taniguchi et al. 2001).

In Vivo Assays for the Determination of Aβ Reduction by γ-Secretase Inhibitors.

In vivo assays are available to demonstrate the inhibition of γ-secretase activity. In these assays, animals, such as mice, that express normal levels of APP and γ-secretase or are engineered to express higher levels of APP and hence Aβ can be used to demonstrate the utility of γ-secretase inhibitors (Dovey, John et al. 2001). In these assays, γ-secretase inhibitors were administered to animals and Aβ levels in multiple compartments, such as plasma, cerebral spinal fluid, and brain extracts, were monitored for Aβ levels using methods previously outlined. For instance, Tg2576 mice, which overexpress human APP, was administered γ-secretase inhibitors by oral gavage at doses that will cause measurable Aβ lowering, typically less than 100 mg/kg. Three hours after dosing plasma, brain, and CSF were collected, frozen in liquid nitrogen, and stored at −80° C. until analysis. For Aβ detection, plasma was diluted 15-fold in PBS with 0.1% Chaps while CSF was diluted 15-fold in 1% Chaps with protease inhibitors (5 µg/ml leupeptin, 30 µg/ml aprotinin, 1 mM phenylmethylsulfonylfluoride, 1 µM pepstatin). Brains were homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate were measured using time-resolved fluorescence of the homogenous sample or one of the other methods previously described.

A γ-secretase inhibitor is considered active in one of the above in vivo assays if it reduces Aβ by at least 50% at a dosage of 100 mg/kg.

All references cited herein are hereby incorporated in their entirety herein by reference.

References

Chapman, P., G. White, et al. (1999). "Impaired synaptic plasticity and learning in aged amyloid precursor protein transgenic mice." *Nature Neurosci.* 2: 271–276.

Dahlgren, K., A. Manelli, et al. (2002). "Oligomeric and fibrillar species of amyloid-β peptides differentially affect neuronal viability." *J. Biol. Chem.* PMID: 12058030; hardcopy in press.

Dovey, H., V. John, et al. (2001). "Functional gamma-secretase inhibitors reduce beta-amyloid peotide levels in brain." *J. Neurochem.* 76: 173–181.

Felsenstein, K., L. Hunihan, et al. (1994). "Altered cleavage and secretion of a recombinant β-APP bearing the Swedish familial Alzheimer's disease mutation." *Nature Genetics* 6: 251–256.

Gotz, J., F. Chen, et al. (2001). "Formation of neurofibrillary tangles in P302L tau transgenic mice induced by Aβ42 fibrils." *Science* 293: 1491–1495.

Harlow, E. and D. Lane (1988). *Antibodies, a laboratory manual.* Cold Spring Harbor, N.Y., Cold Spring Harbor Laboratory.

Lewis, J., D. Dickson, et al. (2001). "Enhanced neurofibrillary degeneration in transgenic mice expressing mutant tau and APP." *Science* 293: 1487–1491.

Marambaud, P., Shioi, J., Serban, G., Georgakopoulos, A., Sarner, S, Nagy, V, Baki, L., Wen, P., Efthimiopoulos, S., Shao, Z, Wisniewski, T., and Robakis, N. K. (2002) A presenilin-1/gamma secretase cleavage releases the E-cadherin intracellular domain and regulates disassembly of adherens junctions. EMBO J. 21:1948–1956.

May, P., Reddy, Y. K., Herz, J. (2002) Proteolytic processing of low density lipoprotein receptor-related protein mediates regulated release of its intracellular domain. J. Biol. Chem. 277: 18736–18743.

McLean, C., R. Cherny, et al. (1999). "Soluble pools of Aβ amyloid as a determinant of severity of neurodegeneration in Alzheimer's disease." *Ann. Neurol.* 46: 860–866.

Mizutani, T., Y. Taniguchi, et al. (2001). "Conservation of the biochemical mechanisms of signal transduction among mammalian Notch family members." *Proc. Natl. Acad. Sci. USA* 98: 9026–9031.

Ni, C. Y., Murphy, M. P., Golde, T. E., and Carpenter, G. (2001) gamma-secretase cleavage and nuclear localization of ErbB-4 receptor tyrosine kinase. Science 294: 2179–2181

Okamoto, I., Kawano, Y., Murakami, D., Sasayama, T., Araki, N., Miki, T., Wong, A. J., and Saya, A. (2001) Proteolytic release of CD44 intracellular domain and its role in the CD44 signaling pathway. J. Cell Biol. 155: 755–762

Seiffert, D., J. Bradley, et al. (2000). "Presenilin-1 and -2 are molecular targets for γ-secretase inhibitors." *J. Biol. Chem.* 275: 34086–34091.

Selkoe, D. (2001). "Alzheimer's Disease: genes, proteins, and therapy." *Physiol. Rev.* 81: 741–766.

Shearman, M., B. D, et al. (2000). "L-685,458, an aspartyl protease transition state mimic, is a potent inhibitor of amyloid β-protein precursor γ-secretase activity." *Biochem.* 39: 8698–8704.

Thal, D., E. Gherbremedhin, et al. (2002). "Two types of sporadic cerebral amyloid angiopathy." *J. Neuropath. Exp. Neuro.* 61: 282–293.

Walsh, D., I. Klyubin, et al. (2002). "Naturally secreted oligomers of amyloid β protein potently inhibit hippocampal long-term potentiation in vivo." *Nature* 416: 535–539.

Wolfe, M. (2001). "Secretase targets for Alzheimer's disease: identification and therapeutic potential." *J. Med. Chem.* 44: 2039–2060.

Zhang, L., L. Song, et al. (2001). "Biochemical characterization of the γ-secretase activity that produces β-amyloid peptides." *Biochem.* 40: 5049–5055.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I):

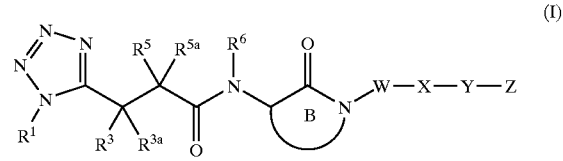

or a pharmaceutically acceptable salt or prodrug thereof, wherein:
$R^1$ is H,
$C_1$–$C_6$ alkyl optionally substituted with 0–2 $R^{2a}$;

$C_2$–$C_6$ alkenyl optionally substituted with 0–2 $R^{2a}$; or
$C_2$–$C_6$ alkynyl optionally substituted with 0–2 $R^{2a}$;

$R^{2a}$, at each occurrence, is independently selected from
H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_4$ alkoxy, $C_1$–$C_4$ haloalkyl, $C_1$–$C_4$ haloalkoxy, $C_1$–$C_4$ haloalkyl-S—;
phenyl substituted with 0–3 $R^{2b}$;
$C_3$–$C_6$ cycloalkyl substituted with 0–3 $R^{2b}$; and
5 to 7 membered heterocycle containing 1 to 4 heteroatoms selected from nitrogen, oxygen, and sulphur, wherein said 5 to 7 membered heterocycle is substituted with 0–3 $R^{2b}$;

$R^{2b}$, at each occurrence, is independently selected from
H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^3$ is H, $NH_2$, $NR^{25}R^{26}$,
$C_1$–$C_6$ alkyl substituted with 0–3 $R^4$;
$C_2$–$C_6$ alkenyl substituted with 0–3 $R^4$; or
$C_2$–$C_6$ alkynyl substituted with 0–3 $R^4$;

$R^{3a}$ is H, $C_1$–$C_6$ alkyl, or $C_2$–$C_6$ alkenyl;
alternatively, $R^3$ and $R^{3a}$ are combined to form a 3–6 membered carbocyclic group selected from cyclopropyl, cyclobutyl, cyclopentyl, cyclopentenyl, cyclohexyl, and cyclohexenyl;
wherein said 3–6 membered carbocyclic group is substituted with 0–2 $R^4$;
additionally, two $R^4$ substituents on adjacent atoms may be combined to form a benzo fused radical; wherein said benzo fused radical is substituted with 0–4 $R^{23}$;
additionally, two $R^4$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{23}$;
additionally, two $R^4$ substituents on the same or adjacent carbon atoms may be combined to form a $C_3$–$C_6$ carbocyclic group substituted with 0–3 $R^{23}$;

$R^4$, at each occurrence, is independently selected from H, OH, Cl, F, Br, I, CN, $NO_2$, $CF_3$, acetyl, $SCH_3$, $S(=O)CH_3$, $S(=O)_2CH_3$, $NR^{15}R^{16}$, $C_1$–$C_4$ alkyl, $C_2$–$C_4$ alkenyl, $C_2$–$C_4$ alkynyl, $C_1$–$C_4$ alkoxy, $C_1$–$C_4$ haloalkyl, $C_1$–$C_4$ haloalkoxy, and $C_1$–$C_4$ haloalkyl-S—, $C_3$–$C_6$ carbocycle, aryl, and a
5 to 6 membered heterocycle containing 1 to 4 heteroatoms selected from nitrogen, oxygen, and sulphur;

$R^5$ is H;
$C_1$–$C_6$ alkyl substituted with 0–2 $R^{5b}$;
$C_2$–$C_6$ alkenyl substituted with 0–2 $R^{5b}$;
$C_2$–$C_6$ alkynyl substituted with 0–2 $R^{5b}$;
$C_3$–$C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5a}$ is H, $C_1$–$C_4$ alkyl, or $C_2$–$C_4$ alkenyl;
alternatively, $R^5$ and $R^{5a}$ may be combined to form a 3–6 membered carbocyclic moiety selected from cyclopropyl, cyclobutyl, cyclopentyl, cyclopentenyl, cyclohexyl, and cyclohexenyl;

$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from
H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_3$ haloalkyl, $C_1$–$C_3$ haloalkoxy, and $C_1$–$C_3$ haloalkyl-S—;

$R^6$ is H or $C_1$–$C_6$ alkyl;
Ring B is a 7 membered lactam,
wherein the lactam is saturated, partially saturated or unsaturated;
wherein each additional lactam carbon is substituted with 0–2 $R^{11}$; and,
optionally, the lactam contains an additional heteroatom selected from —O—, —S—, —S(=O)—, —S(=O)$_2$—, —N=, —NH—, and —N($R^{10}$)—;
additionally, two $R^{11}$ substituents on adjacent atoms may be combined to form a benzo fused radical; wherein said benzo fused radical is substituted with 0–4 $R^{13}$;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;
additionally, two $R^{11}$ substituents on the same or adjacent carbon atoms may be combined to form a $C_3$–$C_6$ carbocyclic radical substituted with 0–3 $R^{13}$;

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
$C_1$–$C_6$ alkyl optionally substituted with 0–3 $R^{10a}$;
$C_6$–$C_{10}$ aryl substituted with 0–4 $R^{10b}$;
$C_3$–$C_{10}$ carbocycle substituted with 0–3 $R^{10b}$; or
5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from
H, $C_1$–$C_6$ alkyl, $OR^{14}$, Cl, F, Br, I, =O, CN, $NO_2$, $NR^{15}R^{16}$, $CF_3$,
phenyl substituted with 0–3 $R^{10b}$;
$C_3$–$C_7$ cycloalkyl substituted with 0–3 $R^{10b}$; and
5 to 7 membered heterocycle containing 1 to 4 heteroatoms selected from nitrogen, oxygen, and sulphur, wherein said 5 to 7 membered heterocycle is substituted with 0–3 $R^{10b}$;

$R^{10b}$, at each occurrence, is independently selected from
H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{11}$, at each occurrence, is independently selected from
H, $C_1$–$C_4$ alkoxy, Cl, F, Br, I, CN, $NO_2$, $NR^{18}R^{19}$, $C(=O)R^{17}$, $C(=O)OR^{17}$, $C(=O)NR^{18}R^{19}$, $S(=O)_2 NR^{18}R^{19}$, $CF_3$;
$C_1$–$C_6$ alkyl optionally substituted with 0–3 $R^{11a}$;
$C_6$–$C_{10}$ aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_7$ cycloalkyl substituted with 0–3 $R^{11b}$; and
5 to 7 membered heterocycle containing 1 to 4 heteroatoms selected from nitrogen, oxygen, and sulphur, wherein said 5 to 7 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond, —$CH_2$—, —$CH_2CH_2$—;
X is a bond, -phenyl-, -pyridyl-, -cyclohexyl-, or -piperidinyl-;
Y is a bond, —C(=O)—, —O—, —S—, —S(=O)—, —S(=O)$_2$—, —NH—, —N(CH$_3$)—, or —N(CH$_2$CH$_3$)—;
Z is H;
$C_1$–$C_8$ alkyl substituted with 0–3 $R^{12a}$;
$C_2$–$C_6$ alkenyl substituted with 0–3 $R^{12a}$;
$C_2$–$C_6$ alkynyl substituted with 0–3 $R^{12a}$;
$C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S—, $C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_3$–$C_6$ cycloalkyl, $C_1$–$C_6$ alkyl, $C_1$–$C_4$ alkoxy, $C_1$–$C_4$ haloalkyl, $C_1$–$C_4$ haloalkoxy, $C_1$–$C_4$ haloalkyl-S, and aryl substituted with 0–3 $R^{12c}$;

$R^{12c}$, at each occurrence, is independently selected from H, methyl, ethyl, propyl, methoxy, ethoxy, amino, hydroxy, Cl, F, Br, I, $CF_3$, $SCH_3$, $S(O)CH_3$, $SO_2CH_3$, —N(CH$_3$)$_2$, N(CH$_3$)H, CN, $NO_2$, $OCF_3$, C(=O)$CH_3$, $CO_2H$, $CO_2CH_3$, and $C_1$–$C_3$ haloalkyl;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{15}$, at each occurrence, is independently selected from H, and $C_1$–$C_6$ alkyl;

$R^{16}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —N(CH$_3$)$_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

additionally, $R^{18}$ and $R^{19}$, when substituents on the same atom, may be combined to form a 5 to 7 membered nitrogen containing heterocyclic ring;

$R^{23}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{25}$, at each occurrence, is independently selected from H, and $C_1$–$C_6$ alkyl; and $R^{26}$, at each occurrence, is independently selected from H, $C_1$–$C_6$ alkyl, $C_3$–$C_4$ alkenyl, $C_3$–$C_4$ alkynyl, ($C_1$–$C_6$ alkyl)-C(=O)—, ($C_1$–$C_6$ alkyl)-S(=O)$_2$—, aryl ($C_1$–$C_4$ alkyl)-, $C_3$–$C_6$ cycloalkyl, and $C_3$–$C_6$ cycloalkyl($C_1$–$C_4$ alkyl)-.

2. A compound, according to claim 1, of Formula (Ib):

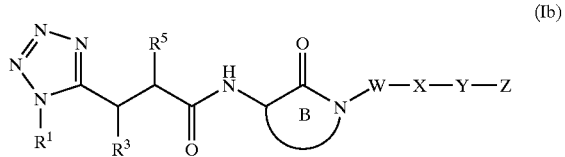

(Ib)

or a pharmaceutically acceptable salt or prodrug thereof, wherein:

$R^1$ is H,
$C_1$–$C_6$ alkyl optionally substituted with 0–1 $R^{2a}$;
$C_2$–$C_6$ alkenyl optionally substituted with 0–1 $R^{2a}$; or
$C_2$–$C_6$ alkynyl optionally substituted with 0–1 $R^{2a}$;

$R^{2a}$, at each occurrence, is independently selected from H, OH, Cl, F, Br, CN, $NO_2$, $CF_3$, acetyl, $SCH_3$, $S(=O)CH_3$, $S(=O)_2CH_3$, methyl, ethyl, methoxy, ethoxy, —$OCF_3$, —$SCF_3$;
phenyl substituted with 0–3 $R^{2b}$;
$C_3$–$C_6$ cycloalkyl substituted with 0–3 $R^{2b}$; and
5 to 7 membered heterocycle containing 1 to 4 heteroatoms selected from nitrogen, oxygen, and sulphur, wherein said 5 to 7 membered heterocycle is substituted with 0–3 $R^{2b}$;

$R^{2b}$, at each occurrence, is independently selected from H, OH, Cl, F, Br, CN, $NO_2$, $CF_3$, acetyl, $SCH_3$, $S(=O)CH_3$, $S(=O)_2CH_3$, methyl, ethyl, methoxy, ethoxy, —$OCF_3$, and —$SCF_3$;

$R^3$ is H, $NH_2$, $C_1$–$C_5$ alkyl, $C_2$–$C_5$ alkenyl, $C_2$–$C_5$ alkynyl, (aryl)$C_1$–$C_4$ alkyl-, or ($C_3$–$C_6$ cycloalkyl)$C_1$–$C_4$ alkyl-;

$R^5$ is H;
$C_1$–$C_4$ alkyl substituted with 0–1 $R^{5b}$;
$C_2$–$C_4$ alkenyl substituted with 0–1 $R^{5b}$; or
$C_2$–$C_4$ alkynyl substituted with 0–1 $R^{5b}$;

$R^{5b}$, at each occurrence, is independently selected from: H, methyl, ethyl, propyl, butyl, methoxy, ethoxy, propoxy, butoxy, $CF_3$, Cl, F, Br, I, =O;
$C_3$–$C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, methyl, ethyl, propyl, methoxy, ethoxy, and —$OCF_3$;

Ring B is selected from:

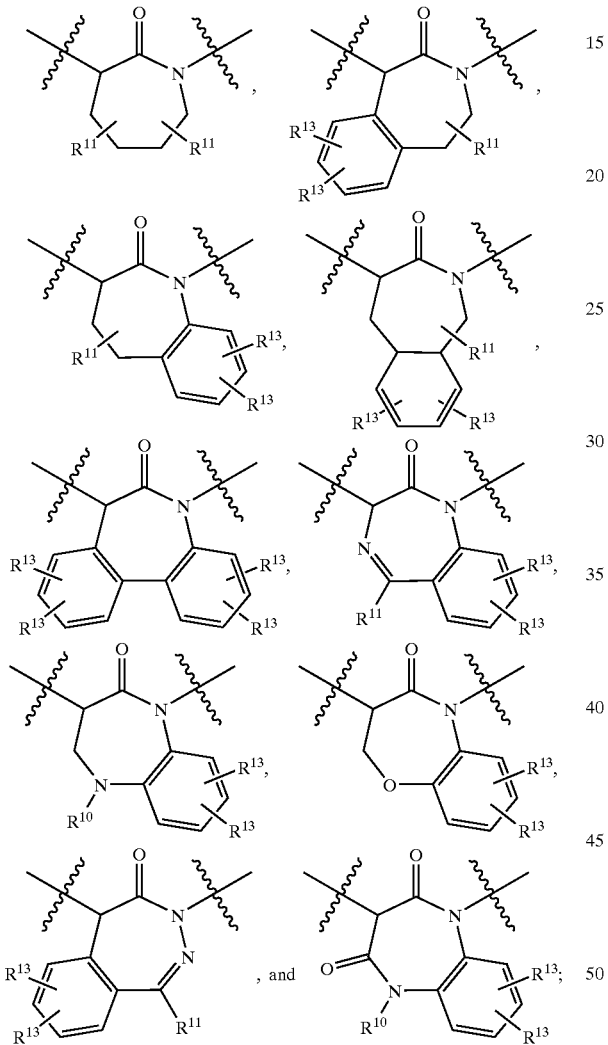

, and $R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;

$C_1$–$C_4$ alkyl optionally substituted with 0–1 $R^{10a}$;

phenyl substituted with 0–3 $R^{10b}$;

$C_3$–$C_7$ carbocycle substituted with 0–3 $R^{10b}$; and 5 to 7 membered heterocycle containing 1 to 4 heteroatoms selected from nitrogen, oxygen, and sulphur, wherein said 5 to 7 membered heterocycle is substituted with 0–3 $R^{10b}$;

$R^{10a}$, at each occurrence, is independently selected from H, $C_1$–$C_4$ alkyl, $OR^{14}$, Cl, F, Br, I, =O, CN, $NO_2$, $NR^{15}R^{16}$, $CF_3$, phenyl substituted with 0–3 $R^{10b}$;

$C_3$–$C_7$ cycloalkyl substituted with 0–3 $R^{10b}$; and 5 to 7 membered heterocycle containing 1 to 4 heteroatoms selected from nitrogen, oxygen, and sulphur, wherein said 5 to 7 membered heterocycle is substituted with 0–3 $R^{10b}$;

$R^{10b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

$R^{11}$, at each occurrence, is independently selected from H, =O, $NR^{18}R^{19}$, $CF_3$;

$C_1$–$C_4$ alkyl optionally substituted with 0–1 $R^{11a}$;

phenyl substituted with 0–3 $R^{11b}$;

$C_3$–$C_7$ carbocycle substituted with 0–3 $R^{11b}$; and 5 to 7 membered heterocycle containing 1 to 4 heteroatoms selected from nitrogen, oxygen, and sulphur, wherein said 5 to 7 membered heterocycle is substituted with 0–3 $R^{11b}$;

$R^{11a}$, at each occurrence, is independently selected from H, $C_1$–$C_4$ alkyl, $OR^{14}$, F, Cl, =O, $NR^{15}R^{16}$, $CF_3$, phenyl substituted with 0–3 $R^{11b}$;

$C_3$–$C_7$ cycloalkyl substituted with 0–3 $R^{11b}$; and 5 to 7 membered heterocycle containing 1 to 4 heteroatoms selected from nitrogen, oxygen, and sulphur, wherein said 5 to 7 membered heterocycle is substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

W is a bond;

X is a bond;

Y is a bond;

Z is H;

$C_1$–$C_6$ alkyl substituted with 0–1 $R^{12a}$;

$C_2$–$C_6$ alkenyl substituted with 0–1 $R^{12a}$; or $C_2$–$C_6$ alkynyl substituted with 0–1 $R^{12a}$;

$R^{12a}$, at each occurrence, is independently selected from H, OH, Cl, F, Br, CN, $NO_2$, $CF_3$, methoxy, ethoxy, —$OCF_3$;

phenyl substituted with 0–4 $R^{12b}$;

$C_3$–$C_6$ carbocycle substituted with 0–4 $R^{12b}$; or 5 to 6 membered heterocycle containing 1 to 4 heteroatoms selected from nitrogen, oxygen, and sulphur, wherein said 5 to 6 membered heterocycle is substituted with 0–3 $R^{12b}$;

$R^{12b}$, at each occurrence, is independently selected from H, OH, Cl, F, Br, CN, $NO_2$, $CF_3$, acetyl, $SCH_3$, $S(=O)CH_3$, $S(=O)_2CH_3$, $C_1$–$C_4$ alkyl, $C_1$–$C_3$ alkoxy, $C_2$–$C_4$ alkenyl, —$OCF_3$, and —$SCF_3$;

$R^{13}$, at each occurrence, is independently selected from H, OH, methyl, ethyl, propyl, methoxy, ethoxy, Cl, F, Br, CN, $NO_2$, $NR^{15}R^{16}$, and $CF_3$;

$R^{14}$ is H, phenyl, benzyl, methyl, ethyl, propyl, or butyl;

$R^{15}$, at each occurrence, is independently selected from H, and $C_1$–$C_4$ alkyl;

$R^{16}$, at each occurrence, is independently selected from H, $C_1$–$C_4$ alkyl, benzyl, phenethyl, ($C_1$–$C_4$ alkyl)-$C(=O)$—, and ($C_1$–$C_4$ alkyl)-$S(=O)_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

R$^{18}$, at each occurrence, is independently selected from
H, C$_1$–C$_6$ alkyl, phenyl, benzyl, phenethyl, (C$_1$–C$_6$ alkyl)-C(=O)—, and (C$_1$–C$_6$ alkyl)-S(=O)$_2$—;

R$^{19}$, at each occurrence, is independently selected from
H, OH, methyl, ethyl, propyl, butyl, phenyl, benzyl, phenethyl; and additionally, R$^{18}$ and R$^{19}$, when substituents on the same atom, may be combined to form a 5 to 7 membered nitrogen containing heterocyclic ring.

3. A compound, according to claim 2, of Formula (Ib):

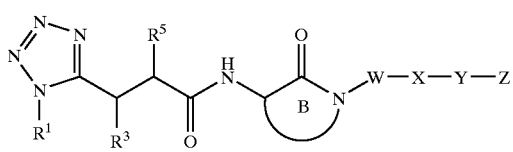

(Ib)

or a pharmaceutically acceptable salt or prodrug thereof, wherein:

R$^1$ is C$_1$–C$_6$ alkyl, C$_2$–C$_6$ alkenyl, or C$_2$–C$_6$ alkynyl;

R$^3$ is H, NH$_2$, C$_1$–C$_5$ alkyl, or C$_2$–C$_5$ alkenyl;

R$^5$ is H;
C$_1$–C$_4$ alkyl substituted with 0–1 R$^{5b}$;
C$_2$–C$_4$ alkenyl substituted with 0–1 R$^{5b}$; or
C$_2$–C$_4$ alkynyl substituted with 0–1 R$^{5b}$;

R$^{5b}$, at each occurrence, is independently selected from:
H, methyl, ethyl, propyl, methoxy, ethoxy, cyclopropyl, cyclobutyl, cyclopentyl, cyclopentenyl, cyclohexyl, cyclohexenyl, and phenyl;

Ring B is selected from:

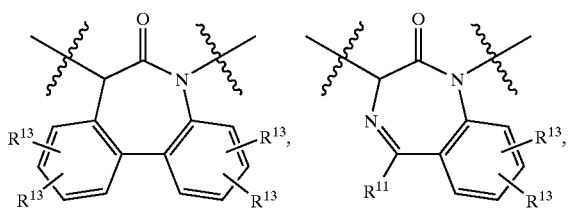

, and

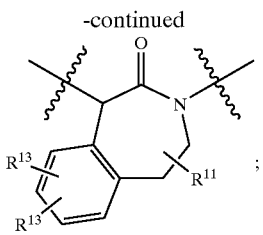

;

R$^{10}$ is H;
C$_1$–C$_4$ alkyl optionally substituted with 0–1 R$^{10a}$;
phenyl substituted with 0–3 R$^{10b}$;
C$_3$–C$_7$ carbocycle substituted with 0–3 R$^{10b}$; and
5 to 7 membered heterocycle containing 1 to 4 heteroatoms selected from nitrogen, oxygen, and sulphur, wherein said 5 to 7 membered heterocycle is substituted with 0–3 R$^{10b}$; wherein said 5 to 7 membered heterocycle is selected from pyridinyl, pyrimidinyl, triazinyl, furanyl, thienyl, thiazolyl, pyrrolyl, pyrrolidinyl, piperazinyl, piperidinyl, homopiperidinyl, pyrazolyl, imidazolyl, imidazolidinyl, oxazolyl, isoxazolyl, morpholinyl, and tetrazolyl;

R$^{10a}$, at each occurrence, is independently selected from
H, methyl, ethyl, methoxy, phenoxy, F, Cl, NR$^{15}$R$^{16}$, CF$_3$;
phenyl substituted with 0–3 R$^{10b}$;
C$_3$–C$_7$ cycloalkyl substituted with 0–3 R$^{10b}$; and
5 to 7 membered heterocycle containing 1 to 4 heteroatoms selected from nitrogen, oxygen, and sulphur, wherein said 5 to 7 membered heterocycle is substituted with 0–3 R$^{10b}$; wherein said 5 to 7 membered heterocycle is selected from pyridinyl, pyrimidinyl, triazinyl, furanyl, thienyl, thiazolyl, pyrrolyl, pyrrolidinyl, piperazinyl, piperidinyl, homopiperidinyl, pyrazolyl, imidazolyl, imidazolidinyl, oxazolyl, isoxazolyl, morpholinyl, and tetrazolyl;

R$^{10b}$, at each occurrence, is independently selected from
H, OH, Cl, F, CF$_3$, methyl, ethyl, methoxy, and —OCF$_3$;

R$^{11}$, at each occurrence, is independently selected from
H, NR$^{18}$R$^{19}$, CF$_3$;
C$_1$–C$_4$ alkyl optionally substituted with 0–1 R$^{11a}$;
phenyl substituted with 0–3 R$^{11b}$;
C$_3$–C$_7$ carbocycle substituted with 0–3 R$^{11b}$; and
5 to 7 membered heterocycle containing 1 to 4 heteroatoms selected from nitrogen, oxygen, and sulphur, wherein said 5 to 7 membered heterocycle is substituted with 0–3 R$^{11b}$; wherein said 5 to 7 membered heterocycle is selected from pyridinyl, pyrimidinyl, triazinyl, furanyl, thienyl, thiazolyl, pyrrolyl, pyrrolidinyl, piperazinyl, piperidinyl, homopiperidinyl, pyrazolyl, imidazolyl, imidazolidinyl, oxazolyl, isoxazolyl, morpholinyl, and tetrazolyl;

R$^{11a}$, at each occurrence, is independently selected from
H, methyl, ethyl, methoxy, phenoxy, F, Cl, CF$_3$;
phenyl substituted with 0–3 R$^{11b}$;
C$_3$–C$_7$ cycloalkyl substituted with 0–3 R$^{11b}$; and
5 to 7 membered heterocycle containing 1 to 4 heteroatoms selected from nitrogen, oxygen, and sulphur, wherein said 5 to 7 membered heterocycle is substituted with 0–3 R$^{11b}$; wherein said 5 to 7 membered heterocycle is selected from pyridinyl, pyrimidinyl, triazinyl, furanyl, thienyl, thiazolyl, pyrrolyl, pyrrolidinyl, piperazinyl, piperidinyl, homopiperidinyl, pyrazolyl, imidazolyl, imidazolidinyl, oxazolyl, isoxazolyl, morpholinyl, and tetrazolyl;

$R^{11b}$, at each occurrence, is independently selected from H, OH, Cl, F, $CF_3$, methyl, ethyl, methoxy, and —$OCF_3$;

W is a bond;

X is a bond;

Y is a bond;

Z is H;

$C_1$–$C_6$ alkyl substituted with 0–1 $R^{12a}$;

$C_2$–$C_6$ alkenyl substituted with 0–1 $R^{12a}$; or $C_2$–$C_6$ alkynyl substituted with 0–1 $R^{12a}$;

$R^{12a}$, at each occurrence, is independently selected from H, OH, Cl, F, $CF_3$, phenyl substituted with 0–2 $R^{12b}$;

$C_3$–$C_6$ carbocycle substituted with 0–2 $R^{12b}$; and 5 to 6 membered heterocycle containing 1 to 4 heteroatoms selected from nitrogen, oxygen, and sulphur, wherein said 5 to 6 membered heterocycle is substituted with 0–2 $R^{12b}$;

$R^{12b}$, at each occurrence, is independently selected from H, OH, Cl, F, Br, CN, $NO_2$, $CF_3$, acetyl, $SCH_3$, $S(=O)CH_3$, $S(=O)_2CH_3$, methyl, ethyl, methoxy, ethoxy, allyl, —$OCF_3$, and —$SCF_3$;

$R^{13}$, at each occurrence, is independently selected from H, OH, methyl, ethyl, methoxy, ethoxy, Cl, F, Br, CN, $NO_2$, $NR^{15}R^{16}$, and $CF_3$;

$R^{15}$, at each occurrence, is independently selected from H, methyl, ethyl, propyl, and butyl;

$R^{16}$, at each occurrence, is independently selected from H, methyl, ethyl, propyl, butyl, benzyl, and phenethyl;

$R^{18}$, at each occurrence, is independently selected from H, methyl, ethyl, propyl, butyl, phenyl, benzyl, and phenethyl; and $R^{19}$, at each occurrence, is independently selected from H, methyl, ethyl, propyl, and butyl.

4. A compound, according to claim 3, of Formula (Ib):

(Ib)

or a pharmaceutically acceptable salt or prodrug thereof, wherein:

$R^1$ is $C_1$–$C_5$ alkyl, $C_2$–$C_5$ alkenyl, or $C_2$–$C_5$ alkynyl;

$R^3$ is H, methyl, ethyl, propyl, butyl, pentyl, ethenyl, propenyl, or butenyl;

$R^5$ is H, $C_1$–$C_5$ alkyl; $C_2$–$C_5$ alkenyl; $C_2$–$C_5$ alkynyl; or ($C_3$–$C_6$ cycloalkyl)$C_1$–$C_4$ alkyl-;

Ring B is selected from:

[structures with $R^{13}$, $R^{11}$, $R^{10}$ substituents]

, and $R^{10}$ is H, $C_1$–$C_4$ alkyl optionally substituted with 0–1 $R^{10a}$;

phenyl substituted with 0–1 $R^{10b}$; or $C_3$–$C_7$ carbocycle substituted with 0–1 $R^{10b}$, wherein said $C_3$–$C_7$ carbocycle is selected from cyclopropyl, cyclobutyl, cyclopentyl, cyclopentenyl, cyclohexyl, cyclohexenyl, and cycloheptyl;

$R^{10a}$, at each occurrence, is independently selected from H, methyl, methoxy, F, Cl, $CF_3$, phenyl substituted with 0–1 $R^{10b}$; and $C_3$–$C_7$ cycloalkyl substituted with 0–1 $R^{10b}$, wherein said $C_3$–$C_7$ carbocycle is selected from cyclopropyl, cyclobutyl, cyclopentyl, cyclopentenyl, cyclohexyl, cyclohexenyl, and cycloheptyl;

$R^{10b}$, at each occurrence, is independently selected from H, OH, Cl, F, $CF_3$, methyl, and methoxy;

$R^{11}$, at each occurrence, is independently selected from H, $NR^{18}R^{19}$, $CF_3$;

$C_1$–$C_4$ alkyl optionally substituted with 0–1 $R^{11a}$;

phenyl substituted with 0–1 $R^{11b}$; and $C_3$–$C_7$ carbocycle substituted with 0–1 $R^{11b}$, wherein said $C_3$–$C_7$ carbocycle is selected from cyclopropyl, cyclobutyl, cyclopentyl, cyclopentenyl, cyclohexyl, cyclohexenyl, and cycloheptyl;

$R^{11a}$, at each occurrence, is independently selected from H, methyl, methoxy, F, Cl, $CF_3$, phenyl substituted with 0–1 $R^{11b}$; and $C_3$–$C_7$ cycloalkyl substituted with 0–1 $R^{11b}$, wherein said $C_3$–$C_7$ carbocycle is selected from cyclopropyl, cyclobutyl, cyclopentyl, cyclopentenyl, cyclohexyl, cyclohexenyl, and cycloheptyl;

$R^{11b}$, at each occurrence, is independently selected from H, OH, Cl, F, $CF_3$, methyl, and methoxy;

W is a bond;
X is a bond;
Y is a bond;
Z is H;
  $C_1$–$C_4$ alkyl substituted with 0–1 $R^{12a}$;
  $C_2$–$C_4$ alkenyl substituted with 0–1 $R^{12a}$; or
  $C_2$–$C_4$ alkynyl substituted with 0–1 $R^{12a}$;

$R^{12a}$, at each occurrence, is independently selected from
  phenyl, cyclopropyl, cyclobutyl, cyclopentyl, cyclopentenyl, cyclohexyl, cyclohexenyl, pyridinyl, pyrimidinyl, triazinyl, furanyl, thienyl, thiazolyl, pyrrolyl, pyrrolidinyl, piperazinyl, piperidinyl, pyrazolyl, imidazolyl, imidazolidinyl, oxazolyl, isoxazolyl, and tetrazolyl;

$R^{13}$, at each occurrence, is independently selected from H, OH, methyl, ethyl, methoxy, ethoxy, Cl, F, Br, CN, $NR^{15}R^{16}$, and $CF_3$;

$R^{15}$ is H, methyl, or ethyl;
$R^{16}$ is H, methyl, or ethyl;
$R^{18}$, at each occurrence, is independently selected from H, methyl, ethyl, propyl, butyl, phenyl, benzyl, and phenethyl; and
$R^{19}$, at each occurrence, is independently selected from H, methyl, ethyl, propyl, and butyl.

5. A compound of Formula (Ib) according to claim 4 wherein:

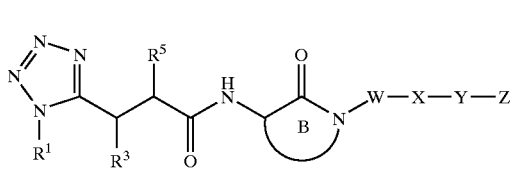
(Ib)

$R^1$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, or —$CH_2C(CH_3)_3$;

$R^3$ is H, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH=CH_2$, cis-$CH_2CH=CH(CH_3)$, trans-$CH_2CH=CH(CH_3)$, or —$CH_2CH_2CH=CH_2$;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, cyclopropyl-$CH_2$—, or cyclobutyl-$CH_2$—;

Ring B is selected from:

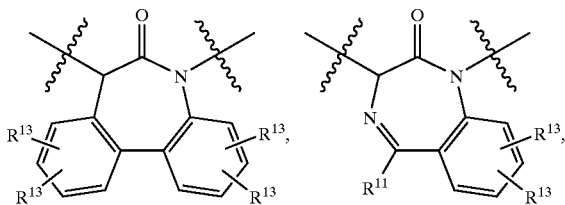

-continued

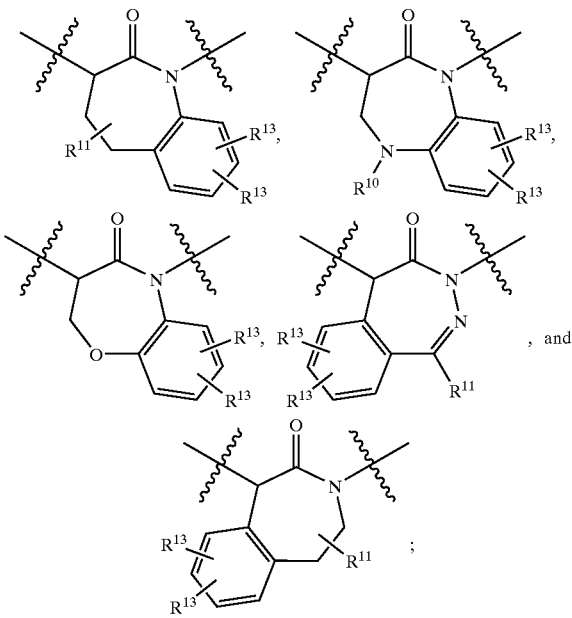

W is a bond;
X is a bond;
Y is a bond;
Z is methyl, ethyl, i-propyl, n-propyl, n-butyl, i-butyl, s-butyl, t-butyl, allyl, cyclopropyl-, cyclobutyl-, cyclopentyl-, cyclopropyl-$CH_2$—, cyclobutyl-$CH_2$—, or cyclopentyl-$CH_2$—;

$R^{10}$, at each occurrence, is independently selected from H, methyl, ethyl, i-propyl, n-propyl, n-butyl, i-butyl, s-butyl, t-butyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)$CH_2$—, (3-Cl-phenyl)$CH_2CH_2$—, 4-$CH_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3-$CH_3$-phenyl)$CH_2CH_2$—, 4-$CF_3$-phenyl, (4-$CF_3$-phenyl)$CH_2$—, (4-$CF_3$-phenyl)$CH_2CH_2$—, cyclopropyl, (cyclopropyl)$CH_2$—, (cyclopropyl)$CH_2CH_2$—, cyclobutyl, (cyclobutyl)$CH_2$—, (cyclobutyl)$CH_2CH_2$—, cyclopentyl, (cyclopentyl)$CH_2$—, (cyclopentyl)$CH_2CH_2$—, cyclohexyl, (cyclohexyl)$CH_2$—, (cyclohexyl)$CH_2CH_2$—, $R^{11}$, at each occurrence, is independently selected from H, methyl, ethyl, i-propyl, n-propyl, n-butyl, i-butyl, s-butyl, t-butyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)$CH_2$—, (3-Cl-phenyl)$CH_2CH_2$—, 4-$CH_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3–$CH_3$-phenyl)$CH_2CH_2$—, 4-$CF_3$-phenyl, (4-$CF_3$-phenyl)$CH_2$—, (4-$CF_3$-phenyl)$CH_2CH_2$—, cyclopropyl, (cyclopropyl)$CH_2$—, (cyclopropyl)$CH_2CH_2$—, cyclobutyl, (cyclobutyl)$CH_2$—, (cyclobutyl)$CH_2CH_2$—, cyclopentyl, (cyclopentyl)$CH_2$—, (cyclopentyl)$CH_2CH_2$—, cyclohexyl, (cyclohexyl)CH$_2$—, (cyclohexyl)CH$_2$CH$_2$—, pyrid-2-yl, pyrid-3-yl, pyrid-4-yl, piperidinyl, or homopiperidinyl; and R$^{13}$, at each occurrence, is independently selected from H, F, Cl, OH, —CH$_3$, —CH$_2$CH$_3$, —OCH$_3$, or —CF$_3$.

6. A compound according to one of claims 1–5 of Formula (Ic):

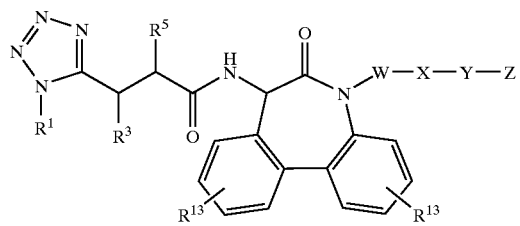

(Ic)

or a pharmaceutically acceptable salt or prodrug thereof.

7. A compound according to one of claims 1–5 of Formula (Id):

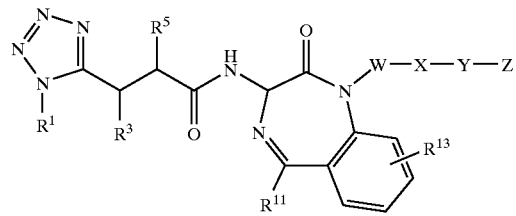

(Id)

or a pharmaceutically acceptable salt or prodrug thereof.

8. A compound according to one of claims 1–5 of Formula (Ie):

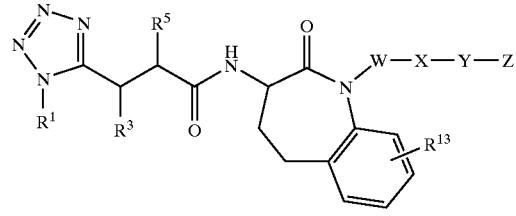

(Ie)

or a pharmaceutically acceptable salt or prodrug thereof.

9. A compound according to one of claims 1–5 of Formula (If):

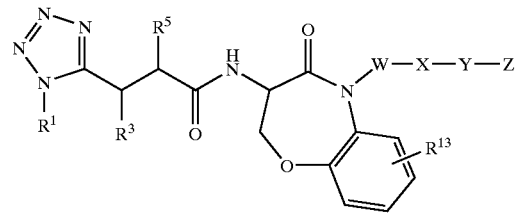

(If)

or a pharmaceutically acceptable salt or prodrug thereof.

10. A compound according to one of claims 1–5 of Formula (Ig):

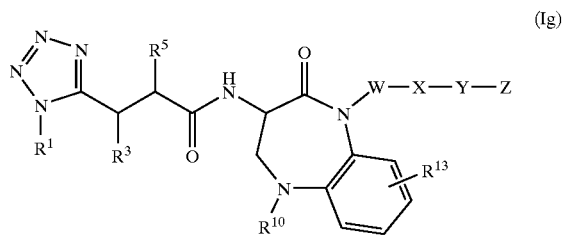

(Ig)

or a pharmaceutically acceptable salt or prodrug thereof.

11. A compound according to one of claims 1–5 of Formula (Ih):

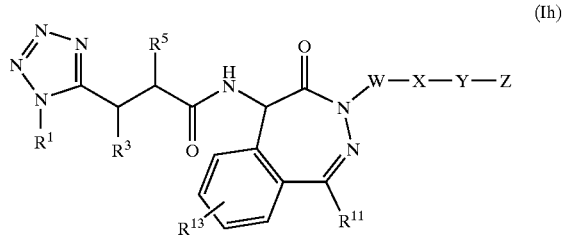

(Ih)

or a pharmaceutically acceptable salt or prodrug thereof.

12. A compound according to claim 1 selected from:

4-Methyl-2-(1-propyl-1H-tetrazol-5-ylmethyl)-pentanoic acid [1-methyl-2-oxo-5-(4-trifluoromethyl-phenyl)-2,3-dihydro-1H-benzo[e][1,4]diazepin-3-yl]-amide;

4-Methyl-2-[1-(1-propyl-1H-tetrazol-5-yl)-ethyl]-pentanoic acid (5-methyl-6-oxo-6,7-dihydro-5H-dibenzo[b,d]azepin-7-yl)-amide;

4-Methyl-2-[1-(1-propyl-1H-tetrazol-5-yl)-ethyl]-pentanoic acid [1-methyl-2-oxo-5-(4-trifluoromethyl-phenyl)-2,3-dihydro-1H-benzo[e][1,4]diazepin-3-yl]-amide;

4-Methyl-2-(1-propyl-1H-tetrazol-5-ylmethyl)-pentanoic acid (1,5-bis-cyclopropylmethyl-2-oxo-2,3,4,5-tetrahydro-1H-benzo[b][1,5]diazepin-3-yl)-amide;

4-Methyl-2-(1-propyl-1H-tetrazol-5-ylmethyl)-pentanoic acid (1-cyclopropylmethyl-2-oxo-2,3,4,5-tetrahydro-1H-benzo[b][1,5]diazepin-3-yl)-amide;

4-Methyl-2-(1-propyl-1H-tetrazol-5-ylmethyl)-pentanoic acid (1-cyclopropylmethyl-5-methyl-2-oxo-2,3,4,5-tetrahydro-1H-benzo[b][1,5]diazepin-3-yl)-amide;

4-Methyl-2-[1-(1-propyl-1H-tetrazol-5-yl)-ethyl]-pentanoic acid (1,5-bis-cyclopropylmethyl-2-oxo-2,3,4,5-tetrahydro-1H-benzo[b][1,4]diazepin-3-yl)-amide;

2-[Amino-(1-propyl-1H-tetrazol-5-yl)-methyl]-4-methyl-pentanoic acid [1-methyl-2-oxo-5-(4-trifluoromethyl-phenyl)-2,3-dihydro-1H-benzo[e][1,4]diazepin-3-yl]-amide;

2-Isobutyl-3-(1-methyl-1H-tetrazol-5-yl)-hex-5-enoic acid (5-cyclopropylmethyl-1-methyl-2-oxo-2,3,4,5-tetrahydro-1H-benzo[b][1,4]diazepin-3-yl)-amide;

2-Isobutyl-4-methyl-3-(1-methyl-1H-tetrazol-5-yl)-pentanoic acid (5-cyclopropylmethyl-1-methyl-2-oxo-2,3,4,5-tetrahydro-1H-benzo[b][1,4]diazepin-3-yl)-amide;

or a pharmaceutically acceptable salt or prodrug thereof.

13. A pharmaceutical composition comprising a compound according to claim 1 and a pharmaceutically acceptable carrier.

14. A method for the treatment of neurological disorders associated with β-amyloid production wherein said disorder is Alzheimer's Disease comprising administering to a host in need of such treatment a therapeutically effective amount of a compound of claim 1.

15. A method for the treatment of Alzheimer's Disease associated with β-amyloid production comprising administering to a host in need of such treatment a therapeutically effective amount of a compound of claim 1.

* * * * *